(12) United States Patent
Jalagam et al.

(10) Patent No.: US 12,286,424 B2
(45) Date of Patent: Apr. 29, 2025

(54) SMALL MOLECULE INHIBITORS OF GALECTIN-3

(71) Applicant: BRISTOL-MYERS SQUIBB COMPANY, Princeton, NJ (US)

(72) Inventors: Prasada Rao Jalagam, Bangalore (IN); Susheel Jethanand Nara, Mumbai (IN); Manoranjan Panda, Yelahanka New Town (IN); Murugesan Natesan, Princeton Junction, NJ (US); Pratik Devasthale, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 253 days.

(21) Appl. No.: 17/998,261

(22) PCT Filed: May 10, 2021

(86) PCT No.: PCT/US2021/031479
§ 371 (c)(1),
(2) Date: Nov. 9, 2022

(87) PCT Pub. No.: WO2021/231243
PCT Pub. Date: Nov. 18, 2021

(65) Prior Publication Data
US 2023/0212158 A1     Jul. 6, 2023

Related U.S. Application Data

(60) Provisional application No. 63/022,627, filed on May 11, 2020.

(51) Int. Cl.
    *C07H 19/12*     (2006.01)
    *C07D 405/04*     (2006.01)
    *C07D 405/14*     (2006.01)
    *C07D 487/08*     (2006.01)

(52) U.S. Cl.
    CPC ......... *C07D 405/14* (2013.01); *C07D 405/04* (2013.01); *C07D 487/08* (2013.01)

(58) Field of Classification Search
    None
    See application file for complete search history.

(56) References Cited

FOREIGN PATENT DOCUMENTS

WO    2018209255 A1    11/2018
WO    WO-2018209276 A1 *    11/2018    ......... A61K 31/4439

* cited by examiner

*Primary Examiner* — Traviss C McIntosh, III
(74) *Attorney, Agent, or Firm* — Jing G. Sun

(57) ABSTRACT

The present disclosure relates to compounds of Formula (I), which inhibit Gal-3, and include pharmaceutically acceptable salts, compositions comprising such compounds, and methods using and making such compounds and compositions. (Formula (I))

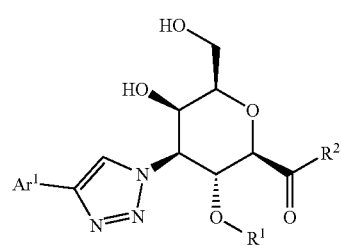

(I)

19 Claims, No Drawings

SMALL MOLECULE INHIBITORS OF GALECTIN-3

CROSS-REFERENCE TO RELATED APPLICATIONS

This application is a 371 of International Application No. PCT/US2021/031479 filed on May 10, 2021, which claims the priority benefit of U.S. Provisional Application No. 63/022,627, filed May 11, 2020; the content of which is herein incorporated by reference in its entirety.

BACKGROUND OF THE INVENTION

Galectin-3 (Gal-3) is a β-galactoside binding lectin of about 30 KDa (Cell 76: 597-598), that is involved in the regulation of inflammatory and fibrotic processes. (Immunological Reviews 230: 160-171). Under uncontrolled inflammation and pro-fibrotic condition, Gal-3 promotes fibroblast proliferation and transformation and mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involvement of Gal-3 in the development of fibrotic process in multiple organs such as lung (Am J. Respir. Crit. Care Med. 185: 537-546), liver (PNAS 103: 5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, WO2014067986, WO2017080973, WO2016120403, US20140099319 and WO2018209255.

DESCRIPTION OF THE INVENTION

The present disclosure relates to compounds of the present invention, which inhibit Gal-3, and include pharmaceutically acceptable salts, compositions comprising such compounds, and methods using and making such compounds and compositions.

In a 1st aspect, the present invention provides, inter alia, a compound of Formula (I):

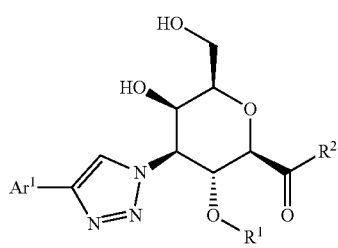

or a pharmaceutically acceptable salt thereof, wherein:

$Ar^1$ is independently phenyl or naphthyl; and wherein each ring moiety is substituted with 1 to 5 substituents selected from cyano, halogen, $C_{1-4}$ alkyl, $C_{1-4}$ alkoxy, $C_{1-4}$ haloalkyl, and $C_{1-4}$ haloalkoxy;

$R^1$ is independently selected from H, $C_{1-4}$ alkyl, and $C_{1-4}$ haloalkyl;

$R^2$ is independently selected from:

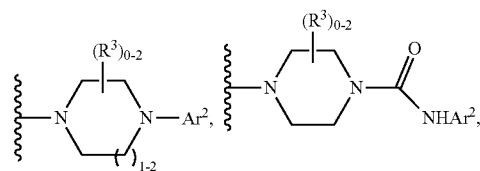

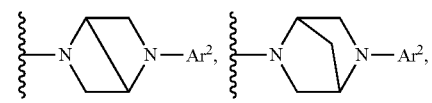

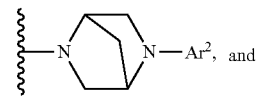

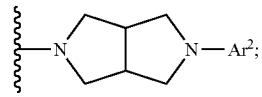

$R^3$ is independently selected from: —$CH_2OH$, halogen, $C_{1-4}$ alkyl, $C_{1-4}$ alkoxy, $C_{1-4}$ haloalkyl, and $C_{1-4}$ haloalkoxy;

$Ar^2$ is independently selected from phenyl,

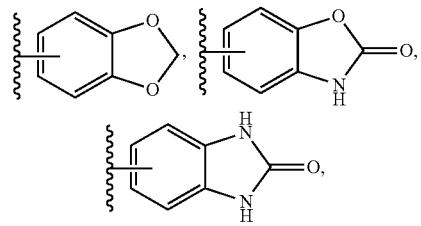

and heteroaryl including from 5 to 10 ring atoms, wherein from 1 to 4 ring atoms are each independently selected from N, N($R^4$), O, and S; and wherein each ring moiety is substituted with 0 to 4 substituents selected from OH, cyano, halogen, $C_{1-4}$ alkyl, $C_{1-4}$ haloalkyl, $C_{1-4}$ alkoxy, $C_{1-4}$ haloalkoxy, N($C_{1-4}$ alkyl)$_2$, —$SO_2$($C_{1-4}$ alkyl), —$NHCO_2$($C_{1-4}$ alkyl), —$NHSO_2$($C_{1-4}$ alkyl), —OPh, —OBn, $C_{3-6}$ cycloalkyl, and phenyl substituted with 0 to 1 substituent selected from cyano, halogen, $C_{1-4}$ alkyl, $C_{1-4}$ haloalkyl, $C_{1-4}$ alkoxy, $C_{1-4}$ haloalkoxy, —$NH_2$, —NH($C_{1-4}$ alkyl), and —N($C_{1-4}$ alkyl)$_2$; and $R^4$ is independently H or $C_{1-4}$ alkyl.

In a 2nd aspect, within the scope of the 1st aspect, wherein the compound is of Formula (Ia):

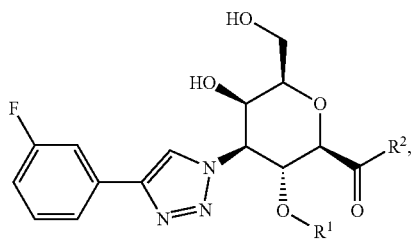

(Ia)

or a pharmaceutically acceptable salt thereof.

In a 3rd aspect, within the scope of the 1st or 2nd aspect, wherein the compound is of Formula (I) or (Ia), or a pharmaceutically acceptable salt thereof, wherein:

$R^1$ is independently H or $C_{1-4}$ alkyl;

$R^2$ is independently selected from:

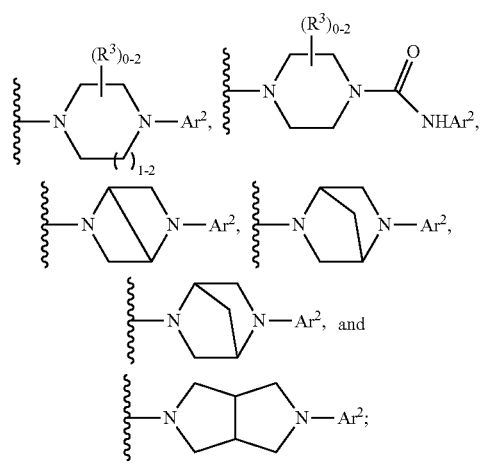

$R^3$ is independently —$CH_2OH$ or $C_{1-4}$ alkyl;

$Ar^2$ is independently selected from phenyl,

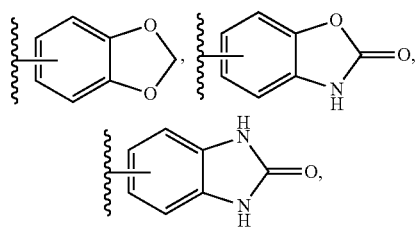

and heteroaryl including from 5 to 10 ring atoms, wherein from 1 to 4 ring atoms are each independently selected from N, N($R^4$), O, and S; and wherein each ring moiety is substituted with 0 to 4 substituents selected from OH, cyano, halogen, $C_{1-4}$ alkyl, $C_{1-4}$ haloalkyl, $C_{1-4}$ alkoxy, $C_{1-4}$ haloalkoxy, N($C_{1-4}$ alkyl)$_2$, —$SO_2$($C_{1-4}$ alkyl), —$NHCO_2$ ($C_{1-4}$ alkyl), and —$NHSO_2$($C_{1-4}$ alkyl); and $R^4$ is independently H or $C_{1-4}$ alkyl.

In a 4th aspect, within the scope of the 1st to 3rd aspects, wherein:

$R^2$ is independently selected from:

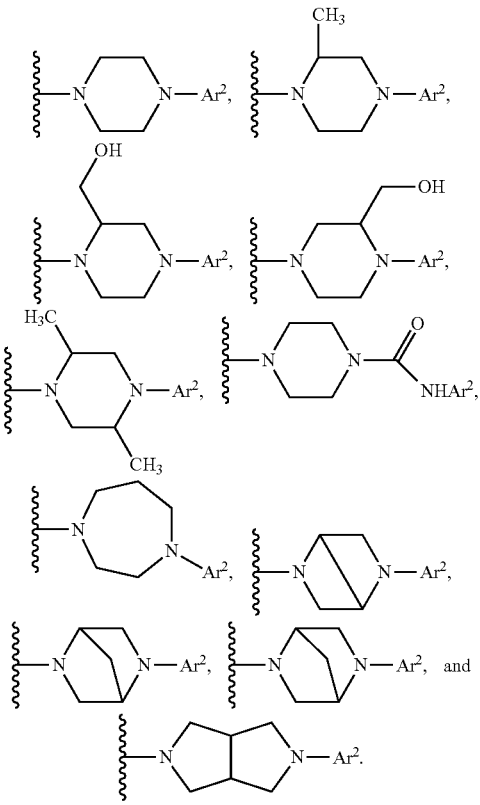

In a 5th aspect, within the scope of the 1st to 4th aspects, wherein:

$Ar^2$ is independently selected from:

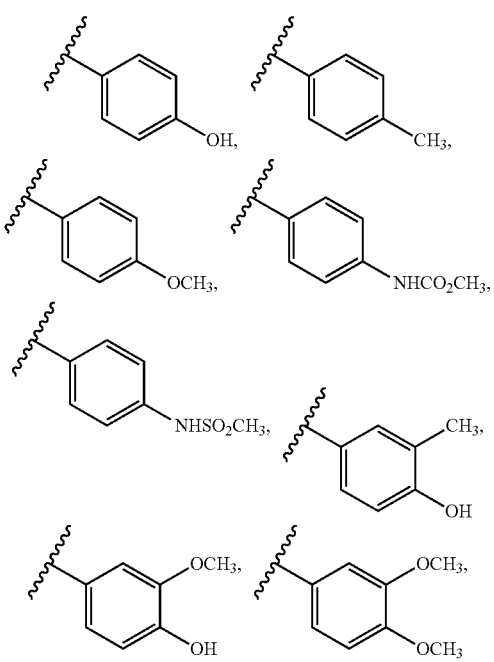

-continued

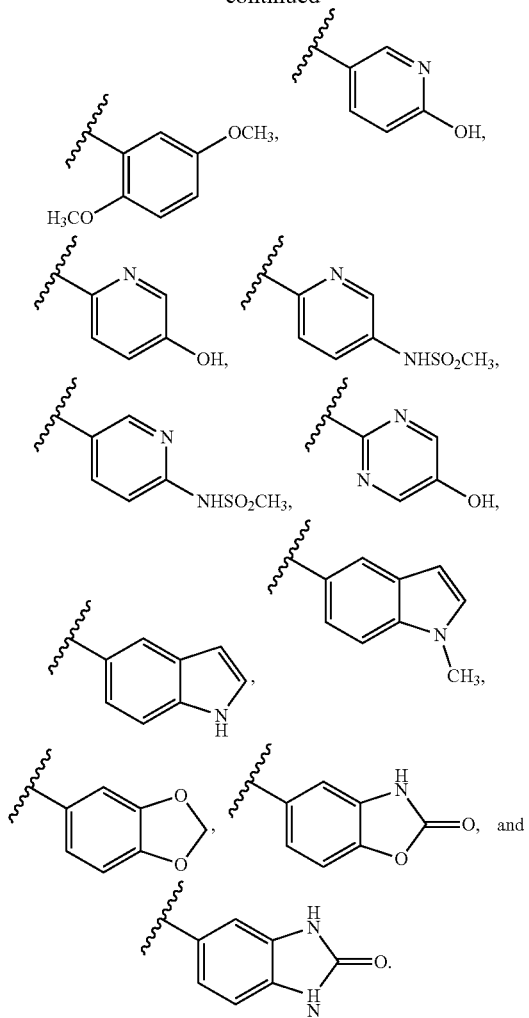

In a 6th aspect, within the scope of the 1st to 5th aspect, wherein $R^1$ is independently H or $CH_3$.

In another aspect, within the scope of any of the 1st to 6th aspects, wherein $R^1$ is H.

In another aspect, within the scope of any of the 1st to 6th aspects, wherein $R^1$ is $CH_3$.

In another aspect, the invention provides a compound selected from the exemplified examples or a pharmaceutically acceptable salt thereof.

In another aspect, the invention provides a compound selected from the Examples 1 to 42 or a pharmaceutically acceptable salt thereof.

Unless specified otherwise, these terms have the following meanings. "Alkyl" means a straight or branched alkyl group composed of 1 to 6 carbons. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo. "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Gal-3 ELISA Assay
Materials:
1. Coating Buffer: Phosphate Buffered Saline (1×)—PBS
The Solution was prepared by dissolving the PBS packets procured from Sigma Aldrich (Catalogue No.: P3813-5×10 Pak)—1 Pack in 1 Liter of Milli-Q water.
2. Asialofetuin from fetal Calf Serum, Type-II. Sigma Aldrich (Catalogue No.: A1908-50MG).
3. Fetal Bovine Serum. Invitrogen (Catalogue No.: 26400-044-500 mL).
4. Tween-20. Sigma Aldrich (Catalogue No.: P1379-250 mL).

5. BD OptEIA Enzyme Reagent Streptavidin-HRP (Catalogue No.: 554066).
6. Sulphuric Acid. Sigma Aldrich (Catalogue No.: 25,810-5).
7. Paraformaldehyde. Sigma Aldrich (Catalogue No.: P6148-500G).
8. TMB Substrate. BD Biosciences (Catalogue No.: 555214).
9. Biotin-tagged hGalectin-3—A 0.82 mg/mL stock solution (28.6 kDa, 28.6713 uM) of biotin tagged hGal-3 in-house synthesized by the proteomic group was used for the titration.
10. TD-139 (EXT-001109-01-001): A small molecule synthesized in-house, used as an internal standard for the small molecule screening in hGalectin-3 neutralization binding assay.

A. Protocol
   a. Coating of Plate: The ASF at concentration 15 nM was prepared in 1×PBS and was plated in the 96 well flat-bottom nunc plates (Nunc immuno plate, Maxisorp, Catalogue No.: 439454) according to the plate-map and was incubated overnight at 4° C. after sealing the plates with a top-seal.
   b. Fixing and Blocking of Plate: On the assay day, the coating solution was drained and the plates were fixed by addition of 100 μL of 2% Paraformaldehyde solution and incubating at 37° C. for 30 min. and washed with 300 μL of wash buffer (PBS with 0.05% Tween-20) for 3 times, spin dried and taken for blocking.

The plates were later blocked with 10% FBS and incubated for 1 h at room temperature. Later the plate was washed with 300 μL of wash buffer (PBS with 0.05% Tween-20) for 3 times.

B. Incubation: After spin drying the plates from previous washing, 100 μL of test compounds, at various concentrations as specified in the plate-map (pre-incubated with the hGalectin-3 or mGalectin-3 at concentration 15 nM for 1 h at Room Temperature-RT) were added onto the plate as per the plate map. The plates were run in duplicates for data duplication and reproducibility.

These plates were incubated at RT for 1 h and were washed for 5 times with wash buffer, spin dried and 100 μL of Streptavidin HRP (1:1000 dilutions) was added and incubated for 1 h at room temperature and washed for 7 times with wash buffer.

C. Detection: After spin drying the plate from previous washing, 100 μL of TMB Substrate was added to each well and incubated for 15 min. at room temperature. Later the reaction was stopped with 2N sulphuric acid and the plate was read in spectramax at 450 nm Results: The read out (OD) obtained were plotted against the control wells after normalization with averaged controls and analyzed for the Log of Inhibitory concentration 50 (Log $IC_{50}$) values for program compounds.

Summary: The $IC_{50}$ values of the program compounds were as presented in the report (attached in excel format from Curve master compilation). The Plate control TD-139 had an $IC_{50}$ value of 10.3 nM and 108.12 nM for human and mouse Galectin-3 respectively. The same was plotted on the semi-log graph.

Pharmaceutical Composition and Methods of Use

The compounds of this invention inhibit Gal-3. Accordingly, another aspect of the invention is a pharmaceutical composition comprising a therapeutically effective amount of a compound of the present invention, or a pharmaceutically acceptable salt thereof, and a pharmaceutically acceptable carrier.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (IBS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related macular degeneration (AMD), diabetic retinopathy, proliferative vitreoretinopathy (PVR), cicatricial pemphigoid, and glaucoma filtration surgery scarring) with a compound of the present invention.

Another aspect of the invention is a method of treating renal fibrosis, pulmonary fibrosis, hepatic fibrosis, arterial fibrosis and systemic sclerosis comprising administering to a compound of the present invention to a patient.

Another aspect of the invention is a method for treating fibrosis of organs (including liver, kidney, lung, heart and skin) comprising administering to a compound of the present invention to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder) comprising administering to a compound of the present invention to a patient.

Another aspect of the invention is a method for treating cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of the present invention to a patient.

Another aspect of the invention is a method for treating inflammatory diseases and conditions (including psoriasis, nephropathy, and pneumonia) comprising administering to a compound of the present invention to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of the present invention to a patient.

Another aspect of the invention is a method for treating renal diseases and conditions comprising administering to a compound of the present invention to a patient.

Another aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of the present invention to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of the present invention to a patient.

Another aspect of the invention is a method for treating pancreatic diseases and conditions comprising administering to a compound of the present invention to a patient.

Another aspect of the invention is a method for treating abnormal angiogenesis-associated diseases and conditions (including arterial obstruction) comprising administering to a compound of the present invention to a patient.

Another aspect of the invention is a method for treating brain-associated diseases and conditions (including cerebral infarction and cerebral hemorrhage) comprising administering to a compound of the present invention to a patient.

Another aspect of the invention is a method for treating neuropathic pain and peripheral neuropathy comprising administering to a compound of the present invention to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of the present invention to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of the present invention or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, PA (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

Section A

LCMS analyses were performed on Waters Acquity UPLC system coupled with Waters TUV and SQ mass detector (Column: BEH C18 2.1×50 mm; Mobile Phase A: water with 0.05% TFA; Mobile Phase B: acetonitrile with 0.05% TFA; Gradient: 2-98% B over 1.6 minutes; Flow: 0.8 mL/min); HPLC analyses were performed on Shimadzu LC10-AT HPLC system coupled with SPD-10AV UV detector (Column YMC S5 Combiscreen ODS 4.6×50 mm; Mobile Phase A: 5:95 acetonitrile:water with 0.1% TFA; Mobile Phase B: 95:5 acetonitrile:water with 0.1% TFA; Gradient: 0-100% B over 40 minutes, then a 1-minute hold at 100% B; Flow: 1 mL/min); Preparative HPLC purifications were conducted on Shimadzu LC-8 preparative HPLC system coupled with SPD 20 UV detector. Detailed conditions are described in experimental procedures.

Methods of Preparation

Analytical LC-MS/HPLC retention time reported for each example and intermediate uses one of the following general analytical LC-MS/HPLC conditions:
LCMS Conditions:
Method A: Column: Ascentis Express C18 (50×2.1 mm), 2.7 µm; Mobile Phase A: 5:95 acetonitrile:water with 10 mM NH₄OAc; Mobile Phase B: 95:5 acetonitrile:water with 10 mM NH₄OAc; Temperature: 50° C.; Gradient: 0-100% B over 3 minutes.

Method B: Column: Ascentis Express C18(50×2.1 mm), 2.7 µm; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes; Flow: 1.1 ml/min.

Method C: Column-KINETEX-XB—C18 (75×3 mm-2.6 µm); Mobile Phase A: 10 mM NH₄COOH in water:ACN (98:02); Mobile Phase B: 10 mM NH₄COOH in water:ACN (02:98); Gradient=20-100% B over 4 minutes; Flow rate: 1.1 mL/min; Detection: UV at 254 nm.

Method D: Column: Waters Acquity UPLC BEH C18 (2.1× 50 mm), 1.7µ; Mobile phase A: 0.1% TFA in water; Mobile phase B: 0.1% TFA in Acetonitrile; Gradient=20-90% B over 1.1 minute, then a 0.6 minute hold at 90% B; Temperature: 50° C.; Flow rate: 0.7 mL/min; Detection: UV at 220 nm.

Method E: Column: Waters Acquity UPLC BEH C18 (2.1× 50 mm) 1.7µ, Mobile phase A: 5 mM NH₄OAc, Acetonitrile (95:5); Mobile phase B: 5 mM NH₄OAc: Acetonitrile (5:95), Gradient=20-90% B over 1.1 minute, then a 0.6 minute hold at 90% B;
Temperature: 50° C.; Flow rate: 0.7 mL/min; Detection: UV at 220 nm Method F: Column-ZORBAX SB—C18 (50×4.6 mm-5.0 µm); Mobile phase A: 10 mM NH₄COOH in water:ACN (98:02); Mobile phase B: 10 mM NH₄COOH IN WATER: ACN (02:98); Gradient=30-100% B over 4 minutes; Flow rate: 1.5 mL/min; Detection: UV at 254 nm.

Method G: Column-Gemini nx-C18 (50×4.6 mm-5 µm); Mobile Phase A: 10 mM NH₄COOH in water:ACN (98:02); Mobile Phase B: 10 mM NH₄COOH in water:ACN (02:98); Gradient=30-100% B over 4 minutes; Flow rate: 1.5 mL/min; Detection: UV at 254 nm.

Prep-HPLC Conditions:

Method A: Column: Waters XBridge C18, 19×150 mm, 5-µm particles; Mobile Phase A: 10-mM ammonium acetate; Mobile Phase B: acetonitrile; Gradient: 15-50% B over 20 minutes, then a 5-minute hold at 100% B; Flow: 15 mL/min.

Method B: Column: X-Bridge Phenyl, 250×19 mm ID, 5µ; Mobile Phase A: 10 mM NH₄OAc in water; Mobile Phase B: Acetonitrile; Gradient: 0-100% B over 18 minutes, then a 5 minute hold at 100% B; Flow: 17 mL/min.

Method C: Column: Sunfire C18, 150×19 mm ID, 5µ; Mobile Phase A: 10 mM NH₄OAc in water; Mobile Phase B: Acetonitrile; Gradient: 0-100% B over 18 minutes, then a 5 minute hold at 100% B; Flow: 17 mL/min.

Method D: Waters XBridge C18, 19×150 mm, 5-µm particles; Mobile Phase A: 0.1% trifluoroacetic acid; Mobile Phase B: acetonitrile; Gradient: 8-32% B over 25 minutes, then a 5-minute hold at 100% B; Flow: 15 mL/min.

Method E: Column: Inertsil ODS, 150×4.6 mm, 5µ; Mobile Phase A: 10 mM NH₄OAc in water; Mobile Phase B: Acetonitrile; Gradient: 0-100% B over 18 minutes, then a 5 minute hold at 100% B; Flow: 17 mL/min.

Method F: Column: Kinetex C18 (250*21.2 ID) 5 micron; Mobile Phase A: 10 mM NH₄OAc in water; Mobile Phase B: Acetonitrile; Gradient: 0-100% B over 13 minutes, then a 5 minute hold at 100% B; Flow: 17 mL/min.

Synthesis of Carboxylic Acid Intermediate

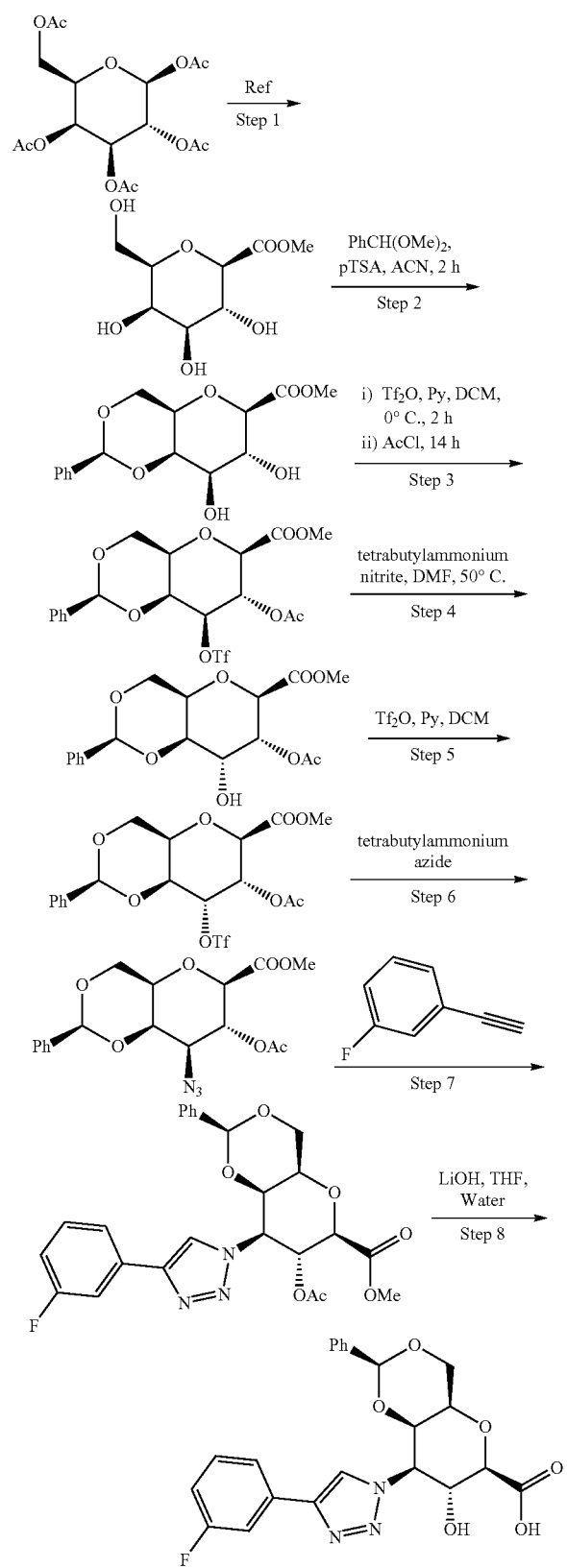

Step 1. Synthesis of (2R,3R,4S,5R,6R)-methyl 3,4,5-trihydroxy-6-(hydroxymethyl)tetrahydro-2H-pyran-2-carboxylate: Synthesized from β-D-galactose pentaacetate by following literature procedure (Ref: Synthesis, 2007, 6, 845-852 and references cited therein).

Step 2. Synthesis of (2S,4aR,6R,7R,8R,8aR)-methyl 7,8-dihydroxy-2-phenylhexahydropyrano[3,2-d][1,3]dioxine-6-carboxylate: p-Toluenesulfonic acid monohydrate (1.199 g, 6.30 mmol) was added to a stirred suspension of (2R,3R,4S,5R,6R)-methyl 3,4,5-trihydroxy-6-(hydroxymethyl)tetrahydro-2H-pyran-2-carboxylate (29 g, 90 mmol) and benzaldehyde dimethyl acetal (33.8 mL, 225 mmol) in acetonitrile (563 mL) at rt under Ar atmosphere. The mixture was degassed with Ar three times and sonicated for 2 min. Then, the reaction mixture was stirred at rt for 4 h, quenched with TEA (5.77 mL, 41.4 mmol) and stirred for 10 min. The mixture was filtered and the filtrate was concentrated under reduced pressure to get the crude product which was purified via chromatography in silica gel (50-100% EtOAc in n-hexane) to yield the title compound (16.3 g, 52.5 mmol, 58%) as a white solid. $^1$H NMR (400 MHz, CHLOROFORM-d): δ ppm 7.53-7.49 (m, 2H), 7.40-7.36 (m, 3H), 5.57 (s, 1H), 4.39 (dd, J=12.5, 1.5 Hz, 1H), 4.28 (dd, J=4.0, 1.0 Hz, 1H), 4.15-4.05 (m, 2H), 3.87-3.84 (m, 4H), 3.73 (td, J=9.0, 4.0 Hz, 1H), 3.56 (q, J=1.5 Hz, 1H), 3.24 (d, J=2.5 Hz, 1H), 2.63 (d, J=8.5 Hz, 1H).

Step 3. Synthesis of (2S,4aR,6R,7S,8S,8aS)-methyl-7-acetoxy-2-phenyl-8-(((trifluoromethyl)sulfonyl)oxy)hexahydropyrano[3,2-d][1,3]dioxine-6-carboxylate: To a solution of (2S,4aR,6R,7R,8R,8aR)-methyl 7,8-dihydroxy-2-phenylhexahydropyrano[3,2-d][1,3]dioxine-6-carboxylate (17.3 g, 55.8 mmol) in DCM (180 mL), pyridine (18.04 mL, 223 mmol) was added at −15° C. and the mixture was stirred for 10 min. Triflic anhydride (8.48 mL, 50.2 mmol) was added drop-wise over a period of 15 min under argon and the mixture was stirred for 1 h at −15° C. The reaction mixture was allowed to reach rt over a period of 2 h. Acetyl chloride (4.76 mL, 66.9 mmol) was added at 0° C., and the mixture was allowed to warm to rt and stirred for 10 h. DCM (300 mL) was added, and the solution was washed with 0.7 N HCl (150 mL), saturated sodium bicarbonate (2×100 mL) and brine solution. The organic layer was separated and dried over sodium sulfate. The solvent was removed under reduced pressure and purified via chromatography in silica gel (30-80% EtOAc in n-hexane) to yield the title compound (14 g, 28.9 mmol, 52%) as a white solid. $^1$H NMR (400 MHz, CHLOROFORM-d): δ ppm 7.53 (dd, J=7.4, 2.1 Hz, 2H), 7.44-7.36 (m, 3H), 5.64 (d, J=9.9 Hz, 1H), 5.60 (s, 1H), 5.00 (dd, J=9.9, 3.6 Hz, 1H), 4.53 (d, J=3.6 Hz, 1H), 4.42 (dd, J=12.8, 1.5 Hz, 1H), 4.08 (dd, J=12.8, 1.5 Hz, 1H), 4.03 (d, J=9.9 Hz, 1H), 3.77 (s, 3H), 3.59 (d, J=1.0 Hz, 1H), 2.10 (s, 3H).

Step 4. Synthesis of (2S,4aR,6R,7R,8R,8aR)-methyl-7-acetoxy-8-hydroxy-2-phenylhexahydropyrano[3,2-d][1,3]dioxine-6-carboxylate: To a solution of (2S,4aR,6R,7S,8S,8aS)-methyl-7-acetoxy-2-phenyl-8-(((trifluoromethyl)sulfonyl)oxy) hexahydropyrano[3,2-d][1,3]dioxine-6-carboxylate (32 g, 66.1 mmol) in DMF (320 mL), tetrabutylammonium nitrate (50.3 g, 165 mmol) was added and degasified twice with argon and the mixture was heated at 50° C. for 6 h. Then the reaction mixture was diluted with EtOAc (500 mL), washed with water (4×200 mL), dried over sodium sulfate and concentrated under reduced pressure. The residue was purified via chromatography in silica gel (60-100% EtOAc in n-hexane) to yield the title compound (15 g, 42.6 mmol, 64%) as a yellow solid. $^1$H NMR (400 MHz, CHLOROFORM-d): δ ppm 7.55-7.51 (m, 2H), 7.42-7.36 (m, 3H), 5.55 (s, 1H), 5.39 (dd, J=10.3, 2.8 Hz, 1H), 4.45 (d, J=10.3 Hz, 1H), 4.37 (dd, J=12.8, 1.5 Hz, 1H), 4.23 (t, J=3.1 Hz, 1H), 4.16-4.13 (m, 1H), 4.05 (dd, J=12.8, 2.0 Hz, 1H), 3.79 (d, J=1.5 Hz, 1H), 3.75 (s, 3H), 2.10 (s, 3H).

Step 5. Synthesis of (2S,4aR,6R,7S,8R,8aS)-methyl-7-acetoxy-2-phenyl-8-(((trifluoromethyl)sulfonyl)oxy)hexahydropyrano[3,2-d][1,3]dioxine-6-carboxylate: To a solution of (2S,4aR,6R,7R,8R,8aR)-methyl 7-acetoxy-8-hydroxy-2-phenyl hexahydropyrano[3,2-d][1,3]dioxine-6-carboxylate (2.3 g, 6.53 mmol) in DCM (20 mL), pyridine (2.112 mL, 26.1 mmol) was added and the mixture was cooled to −15° C. followed by drop wise addition of triflic anhydride (1.654 mL, 9.79 mmol) under argon and stirred for 1 h at −15° C. The reaction mixture was allowed to warm to rt and stirred for 2 h. Then, the reaction mixture was diluted with DCM (200 mL), washed with aq. 0.7 N HCl (50 mL), aq.NaHCO$_3$ (2×50 mL), brine solution and dried over sodium sulphate. The solvent was removed under reduced pressure and the residue was purified via chromatography in silica gel (30-80% EtOAc in n-hexane) to yield the title compound (1.2 g, 2.477 mmol, 38%) as a solid. $^1$H NMR (400 MHz, CHLOROFORM-d): δ ppm 7.54-7.49 (m, 2H), 7.43-7.38 (m, 3H), 5.60 (s, 1H), 5.54 (dd, J=10.5, 3.0 Hz, 1H), 5.28 (t, J=3.3 Hz, 1H), 4.43-4.37 (m, 2H), 4.30 (dd, J=3.5, 1.0 Hz, 1H), 4.11 (dd, J=12.8, 1.5 Hz, 1H), 3.80 (s, 3H), 3.78 (d, J=1.5 Hz, 1H), 2.10 (s, 3H).

Step 6. Synthesis of (2S,4aR,6R,7R,8S,8aR)-methyl-7-acetoxy-8-azido-2-phenylhexahydropyrano[3,2-d][1,3]dioxine-6-carboxylate: To a solution of (2S,4aR,6R,7S,8R,8aS)-methyl-7-acetoxy-2-phenyl-8-(((trifluoromethyl)sulfonyl)oxy) hexahydropyrano[3,2-d][1,3]dioxine-6-carboxylate (1.8 g, 41.3 mmol) in DMF (18 mL), tetrabutyl ammonium azide (3.17 g, 11.15 mmol) was added in a single portion. The mixture was degasified with Ar and heated at 50° C. for 5 h. The reaction mixture was diluted with EtOAc (200 mL), washed with water (3×100 mL), dried over sodium sulfate and concentrated. The residue was purified via chromatography in silica gel (50-90% EtOAc in n-hexane) to yield the title compound (1.2 g, 3.18 mmol, 86%) as a off-white solid. LC-MS, [M+18]$^+$=395.2, (Method C: $t_R$=2.37 min). $^1$H NMR (300 MHz, CHLOROFORM-d): δ ppm 7.53 (dd, J=7.2, 2.3 Hz, 2H), 7.42-7.33 (m, 3H), 5.60 (s, 1H), 5.58-5.51 (m, 1H), 4.40-4.33 (m, 2H), 4.06 (dd, J=12.7, 1.7 Hz, 1H), 3.99 (d, J=9.8 Hz, 1H), 3.76 (s, 3H), 3.50 (s, 1H), 3.41 (dd, J=10.4, 3.2 Hz, 1H), 2.11 (s, 3H).

Step 7. Synthesis of (4aR,6R,7R,8S,8aR)-methyl 7-acetoxy-8-(4-(3-fluorophenyl)-1H-1,2,3-triazol-1-yl)-2-phenylhexahydropyrano[3,2-d][1,3]dioxine-6-carboxylate: To a solution of (4aR,6R,7R,8S,8aR)-methyl 7-acetoxy-8-azido-2-phenyl hexahydropyrano[3,2-d][1,3]dioxine-6-carboxylate (1.2 g, 3.18 mmol) in DMF (50 mL) and water (10.00 mL). 1-ethynyl-3-fluorobenzene (1.146 g, 9.54 mmol), Sodium ascorbate (0.693 g, 3.50 mmol) and copper(II) sulfate pentahydrate (0.715 g, 2.86 mmol) were added sequentially. Reaction mixture was degassed with nitrogen for 10 min and heated to 80° C. for 1 h. The reaction mixture was cooled to RT and diluted with water (60 ml) and DCM (50 ml) and stir for 1 h. Reaction mixture was filtered through celite pad, washed with DCM (100 ml), filtrate taken for further workup. The organic layer separated out and aqueous layer was re-extracted with DCM (2×100 ml), combined organic layer was washed with water (400 ml), brine (100 ml), dried the organic layer over sodium sulfate and concentrated under reduced pressure. To the crude residue, diethyl ether was added and solid was filtered through Buchner funnel and dried for 1 h to the title compound (1.1 g, 2.211 mmol, 69.5% yield) as a white solid. LC-MS, [M+H]$^+$=498.2, (Method C: $t_R$=2.71 min). $^1$H NMR (400 MHz, CDCl$_3$): δ ppm 8.07 (s, 1H), 7.54-7.50 (m, 2H), 7.48-7.35 (m, 6H), 7.05-6.99 (m, 1H), 5.90 (dd, J=11.1, 9.6 Hz, 1H), 5.52 (s, 1H), 5.21 (dd, J=11.1, 3.4 Hz, 1H), 4.51-4.47 (m, 2H), 4.23 (d, J=9.5 Hz, 1H), 4.12 (dd, J=12.8, 1.8 Hz, 1H), 3.81 (s, 3H), 3.80-3.78 (m, 1H), 1.87 (s, 3H).

Step-8. Synthesis of (4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carboxylic acid: To a stirred solution of (4aR,6R,7R,8S,8aR)-methyl 7-acetoxy-8-(4-(3-fluorophenyl)-1H-1,2,3-triazol-1-yl)-2-phenylhexahydropyrano[3,2-d][1,3]dioxine-6-carboxylate (2 g, 4.02 mmol) in Tetrahydrofuran (20 mL) and Water (10 mL) was added lithium hydroxide (0.48 g, 20.10 mmol) and stirred the mixture at rt for 2 h. After confirmation of completion of reaction with LCMS, tetrahydrofuran was removed under reduced pressure. The residue was diluted with water (100 mL) and pH adjusted to approx 2-3 using 1.5N HCl solution. The precipitated solid was filtered and washed with water and dried under reduced pressure to yield the title compound (1.8 g, quantitative). LC-MS, [M+H]$^+$=442.2, (Method C: $t_R$=3.31 min). $^1$H NMR (400 MHz, MEOH-d$_4$) δ ppm 8.46 (s, 1H), 7.56 (dt, J=10.2, 2.2 Hz, 2H), 7.49-7.40 (m, 3H), 7.37-7.30 (m, 3H), 7.09 (td, J=8.4, 2.3 Hz, 1H), 5.56 (s, 1H), 5.12 (dd, J=10.5, 3.5 Hz, 1H), 4.62 (t, J=10.0 Hz, 1H), 4.54 (d, J=3.5 Hz, 1H), 4.37 (d, J=12.5 Hz, 1H), 4.18 (dd, J=12.5, 1.5 Hz, 1H), 4.06 (d, J=9.5 Hz, 1H), 3.89 (s, 1H).

Synthesis of C2-Methoxy carboxylic acid Intermediate

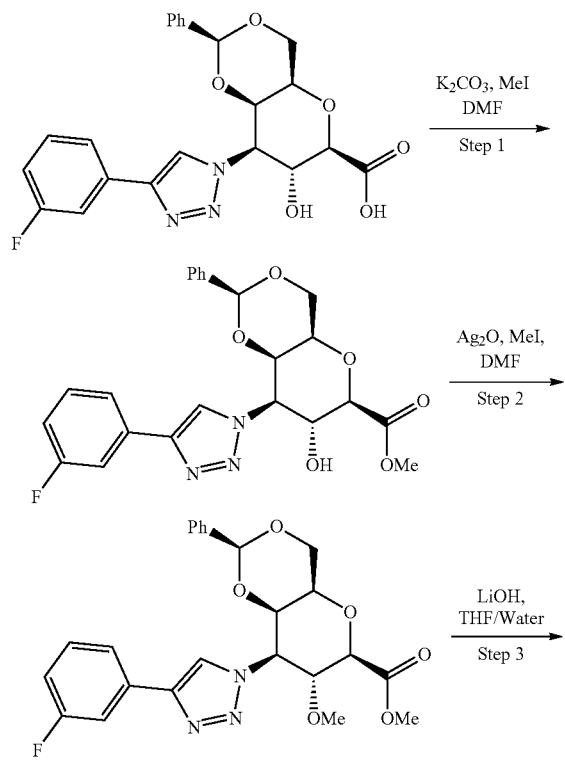

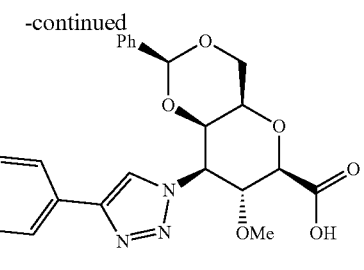

Step-1. Synthesis of (4aR,6R,7R,8R,8aR)-methyl 8-(4-(3-fluorophenyl)-TH-1,2,3-triazol-1-yl)-7-hydroxy-2-phenylhexahydropyrano[3,2-d][1,3]dioxine-6-carboxylate: To a stirred solution of (4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carboxylic acid (1.55 g, 3.51 mmol) in DMF (10 mL), was added K$_2$CO$_3$ (4.85 g, 35.1 mmol) followed by MeI (1.976 mL, 31.6 mmol) and stirred at rt for 16 h. After confirmation of completion of reaction by LCMS, the reaction mass was quenched into ice water (100 mL) and stirred for 10 minutes. The solid was filtered and washed with water and dried under reduced pressure to yield the title compound as an off white solid (1.45 g, 91%). LC-MS, [M+H]$^+$=456.2, (Method F: $t_R$=1.95 min). $^1$H NMR (400 MHz, MEOH-d$_4$) δ ppm 8.41 (s, 1H), 7.58 (d, J=8.0 Hz, 1H), 7.55-7.50 (m, 1H), 7.47-7.40 (m, 3H), 7.37-7.32 (m, 3H), 7.07 (td, J=8.3, 2.5 Hz, 1H), 5.56 (s, 1H), 5.11 (dd, J=11.0, 3.5 Hz, 1H), 4.68-4.61 (m, 1H), 4.53 (d, J=2.5 Hz, 1H), 4.32-4.26 (m, 1H), 4.20-4.13 (m, 2H), 3.89 (s, 1H), 3.82 (s, 3H).

Step-2. Synthesis of (4aR,6R,7R,8R,8aR)-methyl 8-(4-(3-fluorophenyl)-TH-1,2,3-triazol-1-yl)-7-methoxy-2-phenylhexahydropyrano[3,2-d][1,3]dioxine-6-carboxylate: To a stirred solution of (4aR,6R,7R,8R,8aR)-methyl 8-(4-(3-fluorophenyl)-1H-1,2,3-triazol-1-yl)-7-hydroxy-2-phenylhexahydropyrano[3,2-d][1,3]dioxine-6-carboxylate (1.45 g, 3.18 mmol) in DMF (20 mL), was added 4 A MS (1 g) and stirred for 10 minutes at rt.

Then, silver oxide (3.69 g, 15.92 mmol) and MeI (0.1 mL, 15.92 mmol) were added sequentially and stirred at rt for 16 h. Reaction mass was filtered through a celite pad, washed with excess DCM (20 mL) and filtrate was concentrated under reduced pressure to afford (4aR,6R,7R,8R,8aR)-methyl 8-(4-(3-fluorophenyl)-1H-1,2,3-triazol-1-yl)-7-methoxy-2-phenylhexahydropyrano[3,2-d][1,3]dioxine-6-carboxylate as an off white solid (1.3 g, 87%) which was as such taken for next step without further purification. LC-MS, [M+H]$^+$=470.2, (Method F: $t_R$=2.15 min). $^1$H NMR (400 MHz, MEOH-d$_4$) δ ppm 8.59 (s, 1H), 7.62-7.58 (m, 1H), 7.55 (dt, J=10.0, 2.0 Hz, 1H), 7.50-7.42 (m, 3H), 7.40-7.35 (m, 3H), 7.08 (td, J=8.4, 2.3 Hz, 1H), 5.58 (s, 1H), 5.19 (dd, J=10.5, 3.5 Hz, 1H), 4.50 (d, J=2.5 Hz, 1H), 4.47-4.43 (m, 1H), 4.29 (dd, J=12.8, 1.8 Hz, 1H), 4.19-4.13 (m, 2H), 3.87 (s, 1H), 3.84 (s, 3H), 3.12 (s, 3H).

Step-3. Synthesis of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid: To a stirred solution of (4aR,6R,7R,8R,8aR)-methyl 8-(4-(3-fluorophenyl)-1H-1,2,3-triazol-1-yl)-7-methoxy-2-phenylhexahydropyrano[3,2-d][1,3]dioxine-6-carboxylate (1.3 g, 2.8 mmol) in Tetrahydrofuran (50 mL) and Water (50 mL) was added lithium hydroxide (0.33 g, 13.85 mmol) and stirred at rt for 1 h. After confirmation of completion of reaction with LCMS, solvent was removed under reduced pressure. Then the residue was diluted with water (100 mL) and pH adjusted to approx 2-3 using aq.1.5N HCl solution. The precipitated solid was filtered, washed with water and dried under reduced pressure to yield the title compound as an off white solid (1.1 g, 85%). LC-MS, [M+H]$^+$=456.2, (Method F: $t_R$=0.64 min). 1H NMR (400 MHz, MEOH-d$_4$) δ ppm 8.58 (s, 1H), 7.61 (d, J=6.5 Hz, 1H), 7.55 (dd, J=10.0, 2.5 Hz, 1H), 7.50-7.41 (m, 3H), 7.36 (d, J=3.5 Hz, 3H), 7.11-7.04 (m, 1H), 5.58 (s, 1H), 5.16 (dd, J=11.0, 3.5 Hz, 1H), 4.50 (d, J=3.0 Hz, 1H), 4.42-4.35 (m, 1H), 4.34-4.29 (m, 1H), 4.16 (dd, J=12.8, 1.8 Hz, 1H), 4.06 (d, J=9.0 Hz, 1H), 3.84 (s, 1H), 3.18 (s, 3H).

Synthesis of homologated carboxylic acid: 2-((4aR, 6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)acetic acid

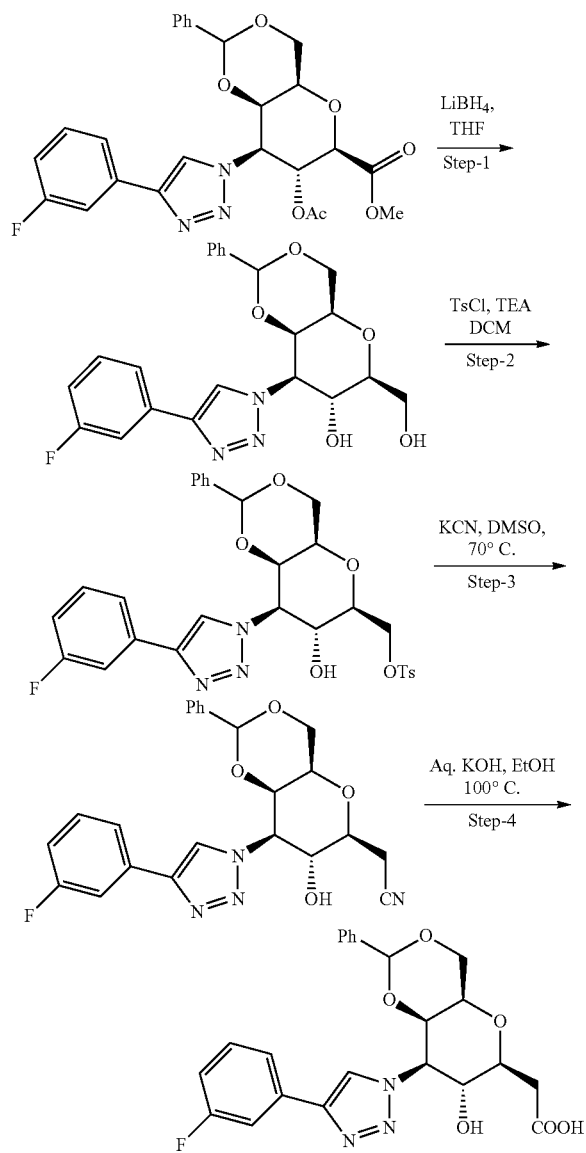

Step-1. Synthesis of (4aR,6S,7R,8R,8aR)-8-(4-(3-fluorophenyl)-1H-1,2,3-triazol-1-yl)-6-(hydroxymethyl)-2-phenylhexahydropyrano[3,2-d][1,3]dioxin-7-ol: To stirred suspension of (4aR,6R,7R,8S,8aR)-methyl 7-acetoxy-8-(4-(3-fluorophenyl)-1H-1,2,3-triazol-1-yl)-2-phenylhexahydropyrano[3,2-d][1,3]dioxine-6-carboxylate (2 g, 4.02 mmol) in tetrahydrofuran (100 mL), LiBH$_4$ (6.03 mL, 12.06 mmol, 2M in THF) was added drop wise under Ar at 0° C. The reaction mixture was allowed to warm to room temperature and stirred for overnight. Reaction mixture was cooled to 0° C., quenched with sat.NH$_4$Cl (50 mL) and extracted with EtOAc (3×200 mL). The combined organic extracts were washed with water (100 mL), brine (100 mL) and dried over sodium sulphate and solvent was removed under reduced pressure to give the crude product which was purified by flash chromatography (10-20% MeOH in CHCl$_3$) to afford (4aR,6S,7R,8R,8aR)-8-(4-(3-fluorophenyl)-1H-1,2,3-triazol-1-yl)-6-(hydroxymethyl)-2-phenylhexahydropyrano[3,2-d][1,3]dioxin-7-ol (1.5 g, 3.51 mmol, 87% yield) as an off-white solid. LC/MS [M+H]$^+$=428.2, (Method C: $t_R$=2.665 min).

Step-2. Synthesis of ((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)methyl 4-methylbenzenesulfonate: To stirred solution of (4aR,6S,7R,8R,8aR)-8-(4-(3-fluorophenyl)-1H-1,2,3-triazol-1-yl)-6-(hydroxymethyl)-2-phenylhexahydropyrano[3,2-d][1,3] dioxin-7-ol (1.0 g, 2.340 mmol) in DCM (25 mL), TEA (1.0 mL, 7.02 mmol), tosyl-Cl (0.491 g, 2.57 mmol) and catalytic amount of DMAP (~15 mg) were added sequentially at 0° C. under N$_2$. The reaction mixture was warm to room temperature and stirred for overnight. Then reaction mixture was extracted with DCM (3×100 mL), washed with water (100 mL), brine (100 mL), dried over sodium sulphate. Solvent was removed under reduced pressure to give the crude product which was purified by flash chromatography (40-65% EtOAc/Hexane) to afford ((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)methyl 4-methylbenzenesulfonate (1.05 g, 1.805 mmol, 77% yield) as off-white solid. LC/MS [M+H]$^+$=582.1, (Method C: $t_R$=3.35 min). $^1$H NMR (300 MHz, CHLOROFORM-d) δ ppm 8.02 (s, 1H), 7.85 (d, J=8.7 Hz, 2H), 7.54-7.30 (m, 10H), 7.07-6.97 (m, 1H), 5.50 (s, 1H), 5.00 (dd, J=10.6, 3.4 Hz, 1H), 4.54-4.39 (m, 3H), 4.32 (dd, J=12.7, 1.3 Hz, 1H), 4.09-4.01 (m, 1H), 3.80-3.72 (m, 1H), 3.69 (d, J=1.1 Hz, 1H), 3.32 (d, J=5.3 Hz, 1H), 2.44 (s, 3H).

Step-3. 2-((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)acetonitrile: To a stirred solution of ((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)methyl 4-methylbenzenesulfonate (0.9 g, 1.547 mmol) in DMSO (20 mL), KCN (1.00 g, 15.47 mmol) was added and heated at 70° C. overnight. Reaction mixture was cooled to rt, extracted with EtOAc (3×150 mL), washed with water (100 mL), brine (100 mL) and dried over sodium sulphate. Solvent was removed under reduced pressure to give the crude product, which was purified by flash chromatography (60-80% EtOAc in hexane) to afford 2-((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)acetonitrile (0.49 g, 1.123 mmol, 73% yield) as an off-white solid. LC/MS [M+H]$^+$=437.1, (Method C: $t_R$=2.675 min). $^1$H NMR (300 MHz, CHLOROFORM-d) δ ppm 8.02 (s, 1H), 7.52-7.31 (m, 8H), 7.09-6.97 (m, 1H), 5.53 (s, 1H), 5.01 (dd, J=10.2, 3.0 Hz, 1H), 4.50-4.42 (m, 2H), 4.38-4.29 (m, 1H), 4.12 (dd, J=12.5, 1.5 Hz, 1H), 3.93 (d, J=4.9 Hz, 1H), 3.90-3.78 (m, 2H), 3.09 (dd, J=17.0, 3.4 Hz, 1H), 2.88 (dd, J=17.0, 7.6 Hz, 1H).

Step-4. Synthesis of 2-((4aR,6S,7R,8R,8aR)-8-(4-(3-fluorophenyl)-1H-1,2,3-triazol-1-yl)-7-hydroxy-2-phenyl-hexahydropyrano[3,2-d][1,3]dioxin-6-yl)acetic acid: 10 mL sealed tube was charged with 2-((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)acetonitrile (0.24 g, 0.550 mmol), EtOH (4 mL), 6N KOH (Aq) (2.75 mL, 16.50 mmol) and vial was sealed. Then reaction mixture was heated at 100° C. for overnight. Reaction mixture was cooled to rt, solvent was removed under reduced pressure to give the crude residue. The crude residue was neutralized with aq.1.5 N HCl (5 mL) and extracted with EtOAc (3×75 mL). The combined organic extracts were washed with water, brine, dried over sodium sulphate and solvent was removed under reduced pressure to give 2-((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl) acetic acid (0.21 g, 0.461 mmol, 84% yield) as pale yellow solid which was as such taken for next step without further purification. LC/MS [M+H]$^+$=456.3, (Method D: $t_R$=1.05 min). $^1$H NMR (400 MHz, MEOH-$d_4$) δ ppm 8.41 (s, 1H), 7.71-7.41 (m, 3H), 7.39-7.32 (m, 5H), 7.18-7.00 (m, 1H), 5.56 (s, 1H), 5.06 (dd, J=10.5, 3.5 Hz, 1H), 4.52 (d, J=3.0 Hz, 1H), 4.32-4.12 (m, 3H), 4.00 (td, J=9.2, 2.8 Hz, 1H), 3.82 (d, J=1.5 Hz, 1H), 3.00 (dd, J=15.8, 2.8 Hz, 1H), 2.61 (dd, J=16.1, 9.0 Hz, 1H).

Example 1. Synthesis of ((2R, 3R, 4S, 5R, 6R)-4-(4-(3-fluorophenyl)-1H-1,2,3-triazol-1-yl)-3,5-dihydroxy-6-(hydroxymethyl)tetrahydro-2H-pyran-2-yl)(4-(4-hydroxyphenyl) piperazin-1-yl) methanone

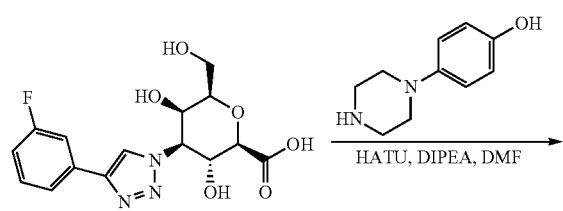

-continued

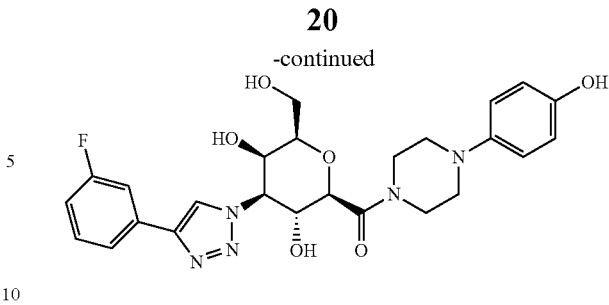

To a stirred solution of (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (50 mg, 0.142 mmol) in DMF (2 mL), 4-(piperazin-1-yl)phenol (63.1 mg, 0.354 mmol), DIPEA (0.25 mL, 1.42 mmol) and HATU (81 mg, 2.12 mol) were added sequentially at room temperature and stirred for overnight. The reaction mixture was concentrated under reduced pressure to give crude residue. The crude product was purified by preparative HPLC [Method B] to yield Example 1 as an off-white solid (5 mg, 0.068 mmol, 48.2% yield). LC-MS, [M+H]$^+$=514.2, [$t_R$=1.054 min, Method B] and & [$t_R$=1.688 min, Method B]. $^1$H NMR (400 MHz, MEOH-$d_4$) δ ppm 8.54 (s, 1H), 7.73-7.67 (m, 1H), 7.63 (ddd, J=10.0, 2.5, 1.5 Hz, 1H), 7.48-7.46 (m, 1H), 7.14-7.05 (m, 1H), 6.96-6.86 (m, 2H), 6.79-6.70 (m, 2H), 4.94 (dd, J=11.0, 3.0 Hz, 1H), 4.73 (dd, J=10.8, 9.3 Hz, 1H), 4.43 (d, J=9.0 Hz, 1H), 4.16 (d, J=3.0 Hz, 1H), 3.95-3.86 (m, 3H), 3.84-3.70 (m, 4H), 3.18-3.05 (m, 4H). hGal3 IC$_{50}$=0.35 μM.

The Examples in Table 1 were prepared in an analogous fashion to Examples 1a and 1b, substituting 4-(piperazin-1-yl)phenol with the appropriate acetylenes in the synthetic sequence.

TABLE 1

| EX # | Structure (LCMS Method A) | LCMS/$t_R$ (min); $^1$H NMR (400 MHz, methanol-$d_4$) | hGal-3 IC$_{50}$ (μM) |
|---|---|---|---|
| 2 | (structure) | (M + H)$^+$ = 515.2/1.13; δ ppm 8.54 (s, 1H), 7.78 (d, J = 3.0 Hz, 1H), 7.72-7.68 (m, 1H), 7.63 (dt, J = 10.0, 2.0 Hz, 1H), 7.48 (td, J = 8.0, 6.0 Hz, 1H), 7.18 (dd, J = 9.0, 3.0 Hz, 1H), 7.10 (td, J = 8.7, 2.3 Hz, 1H), 6.82 (d, J = 9.0 Hz, 1H), 4.93 (dd, J = 10.8, 2.8 Hz, 1H), 4.73 (dd, J = 10.5, 9.0 Hz, 1H), 4.43 (d, J = 9.0 Hz, 1H), 4.16 (d, J = 2.0 Hz, 1H), 3.95-3.70 (m, 7H), 3.54-3.37 (m, 4H). | 0.395 |
| 3 | (structure) | (M + H)$^+$ = 537.2/1.38 δ ppm 8.56 (s, 1H), 7.77 (d, J = 1.7 Hz, 1H), 7.72-7.60 (m, 2H), 7.56 (d, J = 8.8 Hz, 1H), 7.51-7.38 (m, 2H), 7.30 (dd, J = 8.8, 2.4 Hz, 2H), 7.15-7.03 (m, 1H), 4.95 (dd, J = 10.9, 2.8 Hz, 1H), 4.78 (dd, J = 10.8, 9.0 Hz, 1H), 4.44 (d, J = 9.0 Hz, 1H), 4.20-3.90 (m, 6H), 3.84-3.63 (m, 6H). | 0.48 |

TABLE 1-continued

| EX # | Structure (LCMS Method A) | LCMS/$t_R$ (min); $^1$H NMR (400 MHz, methanol-$d_4$) | hGal-3 IC$_{50}$ (μM) |
|---|---|---|---|
| 4 | | (M + H)$^+$ = 516.3/0.90; δ ppm 8.56 (s, 1H), 8.05 (s, 2H), 7.70 (d, J = 8.3 Hz, 1H), 7.64 (d, J = 9.5 Hz, 1H), 7.48-7.43 (m, 1H), 7.10-7.05 (m, 1H), 4.93 (dd, J = 10.8, 2.8 Hz, 1H), 4.75 (dd, J = 10.8, 9.3 Hz, 1H), 4.44 (d, J = 9.3 Hz, 1H), 4.16 (d, J = 2.4 Hz, 1H), 3.92 (t, J = 5.6 Hz, 1H), 3.80-3.70 (m, 10H). | 0.85 |
| 5 | | (M + H)$^+$ = 544.2/1.26; δ ppm 8.53 (s, 1H), 7.70-7.66 (m, 1H), 7.65-7.59 (m, 1H), 7.48-7.43 (m, 1H), 7.10-7.08 (m, 1H), 6.73-6.66 (m, 2H), 6.47 (dd, J = 8.5, 2.5 Hz, 1H), 4.96-4.91 (m, 1H), 4.71 (dd, J = 11.0, 9.0 Hz, 1H), 4.42 (d, J = 9.0 Hz, 1H), 4.14 (d, J = 3.0 Hz, 1H), 3.92-3.85 (m, 3H), 3.85-3.80 (m, 3H), 3.78-3.67 (m, 4H), 3.15-3.04 (m, 4H). | 0.36 |
| 6 | | (M + H)$^+$ = 551.2/1.61; δ ppm 8.57 (s, 1H), 7.76-7.61 (m, 2H), 7.54-7.42 (m, 1H), 7.41-7.29 (m, 1H), 7.24-7.20 (m, 1H), 7.16-7.03 (m, 3H), 6.40-6.35 (m, 1H), 4.97 (dd, J = 2.8, 10.8 Hz, 1H), 4.76 (dd, J = 9.0, 10.5 Hz, 1H), 4.47 (d, J = 9.0 Hz, 1H), 4.20-4.18 (m, 1H), 3.98-3.88 (m, 5H), 3.86-3.74 (m, 5H), 3.26-3.20 (m, 2H), 3.19-3.15 (m, 2H). | 0.42 |

Example-7. Synthesis of ((2R, 3R, 4S, 5R, 6R)-4-(4-(3-fluorophenyl)-1H-1,2,3-triazol-1-yl)-3,5-dihydroxy-6-(hydroxymethyl)tetrahydro-2H-pyran-2-yl)(4-(4-hydroxy-3-methylphenyl)piperazin-1-yl)methanone

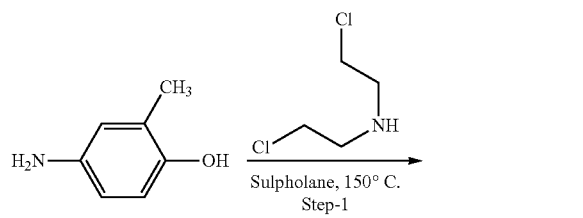

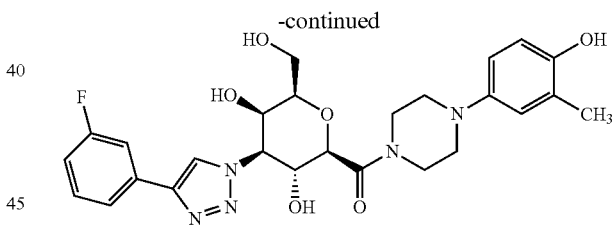

Step-1. Synthesis of 2-methyl-4-(piperazin-1-yl) phenol: To a stirred solution of 4-amino-2-methylphenol (0.5 g, 4.06 mmol) in Sulfolane (5 mL), bis(2-chloroethyl)amine (0.634 g, 4.47 mmol) was added and heated at 150° C. for 16 h. Then the reaction mixture was cooled to rt, diluted with acetone (35 mL) and stirred for 1 h. Reaction mixture was filtered and residue was dried under vacuum to afford 2-methyl-4-(piperazin-1-yl) phenol (500 mg, 64.1%) as a Black solid. LC-MS, [M+H]$^+$=193.2, [Method C, $t_R$=0.546 min].

Step-2. Synthesis of ((2R, 3R, 4S, 5R, 6R)-4-(4-(3-fluorophenyl)-1H-1,2,3-triazol-1-yl)-3,5-dihydroxy-6-(hydroxymethyl)tetrahydro-2H-pyran-2-yl)(4-(4-hydroxy-3-methylphenyl)piperazin-1-yl)methanone: Prepared in a similar fashion as described in Example 1 by using 2-methyl-4-(piperazin-1-yl) phenol (10.88 mg, 0.057 mmol) and (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.02 g, 0.057 mmol). The crude material was purified by prep HPLC (Method B) to afford Example 2 (6.6 mg, 0.013 mmol, 22.10% yield). LC-MS, [M+H]+=528.3, [Method C, $t_R$=1.085 min]. $^1$H NMR (400 MHz, MEOH-d$_4$) δ ppm 8.55 (s, 1H), 7.73-7.60 (m, 2H), 7.48-7.42 (m, 1H), 7.15-7.05 (m, 1H), 6.82 (s, 1H), 6.75-6.66 (m, 2H), 4.92 (dd, J=10.8, 2.8 Hz, 1H), 4.72 (dd, J=10.8, 9.2 Hz, 1H, 1H), 4.43 (d, J=9.2 Hz, 1H), 4.16 (d, J=2.8 Hz, 1H), 3.96-3.71 (m, 7H), 3.08-3.00 (m, 4H), 2.19 (s, 3H). hGal3 IC$_{50}$=0.27 µM.

Example-8. Synthesis of N-(6-(4-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)piperazin-1-yl)pyridin-3-yl)methanesulfonamide

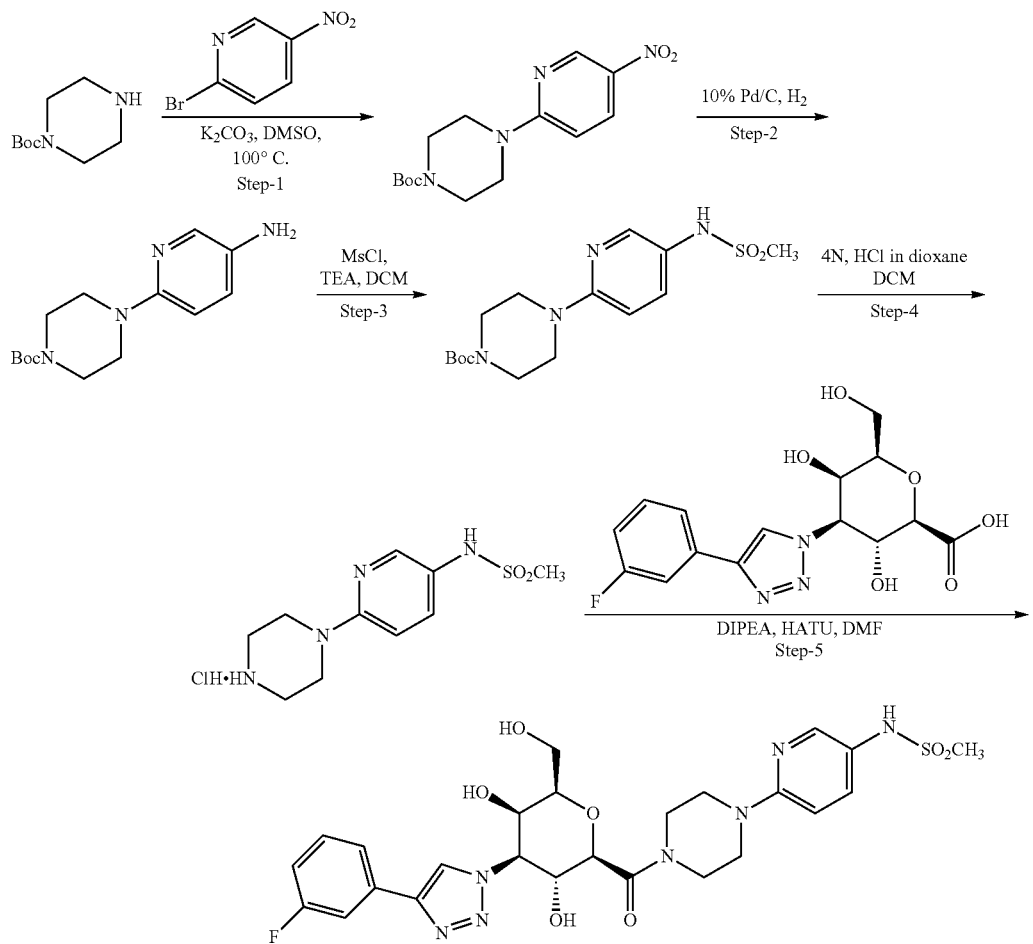

Step-1. Synthesis of tert-butyl 4-(5-nitropyridin-2-yl) piperazine-1-carboxylate: To a stirred solution 2-bromo-5-nitropyridine (1.0 g, 4.93 mmol) in DMSO (10 mL), potassium carbonate (1.362 g, 9.85 mmol), tert-butyl piperazine-1-carboxylate (1.376 g, 7.39 mmol) and TBAI (0.182 g, 0.493 mmol) were added sequentially at rt. Then the reaction mixture was heated at 70° C. for 12 h. The reaction mixture was cooled to room temperature, filtered through Celite pad and washed with EtOAc (30 mL). Then the filtrate was washed with water, brine solution, dried over Na$_2$SO$_4$ and concentrated under reduced pressure to give crude compound. The crude residue was purified by flash chromatography (0-50% EtOAc in pet ether) to afford tert-butyl 4-(5-nitropyridin-2-yl) piperazine-1-carboxylate (1.2 g, 3.89 mmol, 79% yield) as an off white solid. LC/MS [M+H]+=309.1, $t_R$=2.66 min (Method C).

Step-2. Synthesis of tert-butyl 4-(5-aminopyridin-2-yl) piperazine-1-carboxylate: To a degassed stirred solution tert-butyl 4-(5-nitropyridin-2-yl) piperazine-1-carboxylate (0.5 g, 1.622 mmol) in MeOH/EtOAc (8 mL, 1:1) was added Pd/C (0.863 g, 0.811 mmol) under N$_2$. Then the reaction mixture was stirred under H$_2$ atm at ambient temperature for 5 h. The reaction mixture was filtered through Celite pad, washed with MeOH (20 mL) and filtrate was evaporated under reduced pressure to afford tert-butyl 4-(5-aminopyridin-2-yl) piperazine-1-carboxylate (0.4 g, 1.437 mmol, 89% yield) as a color less liquid which was as such taken for next step without further purification. LC/MS [M+H]+=279.2, (Method C: $t_R$=1.66 min).

Step-3. Synthesis of tert-butyl 4-(5-(methylsulfonamido) pyridin-2-yl)piperazine-1-carboxylate: To an ice cooled stirred solution of tert-butyl 4-(5-aminopyridin-2-yl) piperazine-1-carboxylate (0.2 g, 0.719 mmol) in DCM (5 mL), were added DIPEA (0.251 mL, 1.437 mmol) and mesyl-Cl (0.056 mL, 0.719 mmol) were added sequentially under Nitrogen. The reaction mixture was allowed to warm to rt and stirred for 2 h. The reaction mixture was extracted with DCM (2×30 mL), washed with water, brine, dried over Na$_2$SO$_4$ and solvent was removed under reduced pressure to give tert-butyl 4-(5-(methylsulfonamido) pyridin-2-yl)piperazine-1-carboxylate (0.2 g, 0.561 mmol, 78% yield) as an color less liquid which was as such taken for next step without further purification. LC/MS [M+H]⁺=357.4, (Method E: $t_R$=1.05 min).

Step-4. Synthesis of N-(6-(piperazin-1-yl) pyridin-3-yl) methane sulfonamide: To a stirred solution of tert-butyl 4-(5-(methylsulfonamido) pyridin-2-yl)piperazine-1-carboxylate (0.15 g, 0.421 mmol) in DCM (4 mL), was added 4N HCl in dioxane (0.526 mL, 2.104 mmol) at 0° C. The reaction mixture was allowed to reach room temperature and stirred for 2 h. Then the solvent as removed under reduced pressure, triturated with pentane to give N-(6-(piperazin-1-yl) pyridin-3-yl)methane sulfonamide (80 mg, 0.312 mmol, 74.2% yield) as an off-white solid which was as such taken for next step without further purification. LC/MS [M+H]⁺= 257.3, (Method E: $t_R$=0.45 min).

Step-5. Synthesis of N-(6-(4-(((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)piperazin-1-yl)pyridin-3-yl)methanesulfonamide: Prepared in a similar fashion as described in Example 1 by using N-(6-(piperazin-1-yl)pyridin-3-yl)methane sulfonamide (29.0 mg, 0.113 mmol) and (2R,3R,4S,5R,6R)-4-(4-(3-fluorophenyl)-1H-1, 2,3-triazol-1-yl)-3,5-dihydroxy-6-(hydroxymethyl)tetrahydro-2H-pyran-2-carboxylic acid (20 mg, 0.057 mmol). The crude product was purified by preparative HPLC [Method B] to yield Example 8 (0.6 mg, 1.014 µmol, 1.8% yield). LC-MS, [M+H]⁺=592.0, [Method A, $t_R$=1.19 min]. ¹H NMR (400 MHz, MEOH-d₄) d=8.53 (s, 1H), 8.08 (d, J=2.8 Hz, 1H), 7.72-7.65 (m, 1H), 7.64-7.59 (m, 1H), 7.58-7.51 (m, 1H), 7.50-7.41 (m, 1H), 7.11-7.03 (m, 1H), 6.91-6.84 (m, 1H), 4.96 (dd, J=10.8, 2.8 Hz, 1H), 4.76-4.74 (m, 1H), 4.45 (d, J=9.2 Hz, 1H), 4.17 (d, J=2.8 Hz, 1H), 3.93-3.61 (m, 11H), 2.93 (s, 3H). hGal3 IC₅₀=0.76 µM.

Example 9. Synthesis of 5-(4-(((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)piperazin-1-yl)-1H-benzo[d]imidazol-2 (3H)-one

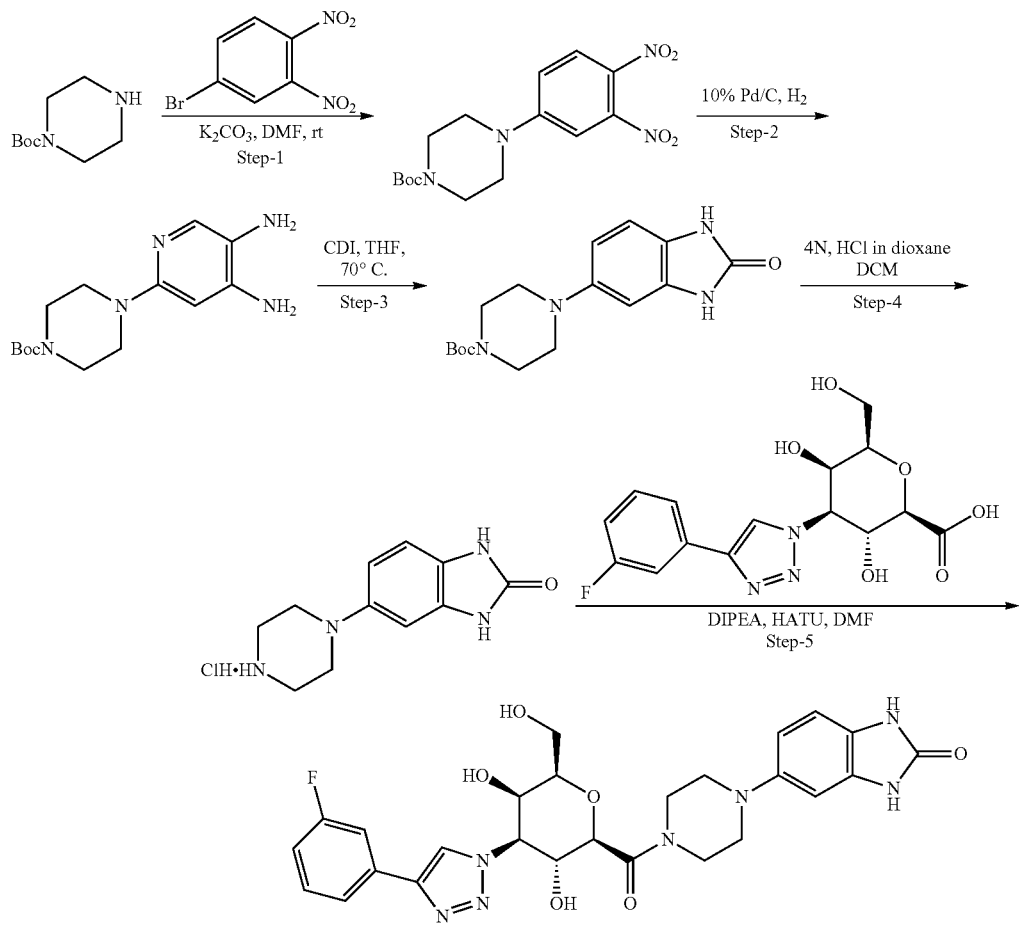

Step-1. Synthesis of tert-butyl 4-(3,4-dinitrophenyl)piperazine-1-carboxylate: To a solution of 4-fluoro-1, 2-dinitrobenzene (1 g, 5.37 mmol) and tert-butyl piperazine-1-carboxylate (1.0 g, 5.37 mmol) in DMF (5 mL) was added K₂CO₃ (0.89 g, 6.45 mmol) and reaction mixture was stirred at rt for 30 minutes. The reaction mixture was poured into ice cold water and stirred for 15 min. The precipitated solid was filtered, washed with excess water and dried under reduced pressure to afford tert-butyl 4-(3,4-dinitrophenyl) piperazine-1-carboxylate as a yellow solid (1.85 g, 93% yield). LC/MS [M+18]⁺=369.9, (Method C: $t_R$=3.54 min). ¹H NMR (400 MHz, CHLOROFORM-d) δ ppm 8.03 (d, J=9.0 Hz, 1H), 6.92 (d, J=3.0 Hz, 1H), 6.88 (dd, J=9.5, 3.0 Hz, 1H), 3.66-3.60 (m, 4H), 3.50-3.44 (m, 4H), 1.49 (s, 9H).

Step-2. Synthesis of tert-butyl 4-(3,4-diaminophenyl)piperazine-1-carboxylate: The solution of tert-butyl 4-(3,4- dinitrophenyl)piperazine-1-carboxylate (0.85 g, 2.41 mmol) in MeOH (100 mL) was charged to a sealable hydrogen flask. The solution was sequentially evacuated and purged with nitrogen gas. To this 10% Pd on carbon (1.3 g, 1.206 mmol) was added under nitrogen atmosphere. The reaction mixture was stirred under hydrogen atmosphere at ambient atmospheric pressure for 16 h. The reaction mixture was filtered through a celite pad and the residue on the pad was thoroughly rinsed with MeOH (3×30 mL). The combined filtrate was concentrated under reduced pressure to afford tert-butyl 4-(3,4-diaminophenyl)piperazine-1-carboxylate (471 mg, 61%) which was as such used for the next step without further purification. LC/MS [M+H]$^+$=292.5, (Method C: $t_R$=2.022 min). $^1$H NMR (400 MHz, DMSO-d$_6$) δ ppm 6.40 (d, J=8.0 Hz, 1H), 6.23 (d, J=2.5 Hz, 1H), 6.04 (dd, J=8.0, 2.5 Hz, 1H), 4.39 (s, 2H), 4.04 (s, 2H), 3.44-3.38 (m, 4H), 2.83-2.78 (m, 4H), 1.42 (s, 9H).

Step-3. Synthesis of tert-butyl 4-(2-oxo-2,3-dihydro-1H-benzo[d]imidazol-5-yl)piperazine-1-carboxylate: To a solution of tert-butyl 4-(3,4-diaminophenyl) piperazine-1-carboxylate (100 mg, 0.34 mmol) in Tetrahydrofuran (5 mL), CDI (58.2 mg, 0.36 mmol) was added and the reaction mixture was heated at 60° C. for 16 h. The reaction mixture was cooled to room temperature, solvent was removed under reduced pressure and triturated with diethyl ether to yield tert-butyl 4-(2-oxo-2,3-dihydro-1H-benzo[d]imidazol-5-yl) piperazine-1-carboxylate as a dark brown solid (45 mg, 40% yield), which was as such taken for next step without further purification. LC/MS [M+H]$^+$=319.2, (Method C: $t_R$=2.13 min). $^1$H NMR (400 MHz, DMSO-d$_6$) δ ppm 10.43 (s, 1H), 10.30 (s, 1H), 6.78 (d, J=8.5 Hz, 1H), 6.59-6.52 (m, 2H), 3.48-3.39 (m, 4H), 2.83-2.78 (m, 4H), 1.42 (s, 9H).

Step-4. Synthesis of 5-(piperazin-1-yl)-1H-benzo[d]imidazol-2(3H)-one hydrochloride: Prepared in a similar fashion as described in Example 8, Step-4 using tert-butyl 4-(2-oxo-2,3-dihydro-1H-benzo[d]imidazol-5-yl)piperazine-1-carboxylate (30 mg, 0.09 mmol). Recrystallization of the residue with pentane gave 5-(piperazin-1-yl)-1H-benzo[d]imidazol-2(3H)-one hydrochloride (24 mg, 70%) as an off white solid. LC/MS [M+H]$^+$=219.1, (Method C: $t_R$=0.40 min).

Step-5. Synthesis of 5-(4-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)piperazin-1-yl)-1H-benzo[d]imidazol-2(3H)-one: Prepared in a similar fashion as described in Example 1 using 5-(piperazin-1-yl)-1H-benzo[d]imidazol-2(3H)-one hydrochloride (28 mg, 0.11 mmol) and (2R,3R,4S,5R,6R)-4-(4-(3-fluorophenyl)-1H-1,2,3-triazol-1-yl)-3,5-dihydroxy-6-(hydroxymethyl) tetrahydro-2H-pyran-2-carboxylic acid (20 mg, 0.06 mmol). The crude product was purified by preparative HPLC [Method A] to afford Example 9 as a brown solid (11.5 mg, 36% yield). LC-MS, [M+H]$^+$=554.2. LCMS Conditions—Method A, $t_R$=1.085 min. $^1$H NMR (400 MHz, MEOH-d$_4$) δ ppm 8.54 (s, 1H), 7.70 (d, J=7.8 Hz, 1H), 7.63 (d, J=9.8 Hz, 1H), 7.51-7.44 (m, 1H), 7.12-7.07 (m, 1H), 6.99-6.93 (m, 1H), 6.82-6.76 (m, 2H), 4.95 (dd, J=10.8, 2.9 Hz, 1H), 4.77-4.70 (m, 1H), 4.44 (d, J=9.0 Hz, 1H), 4.17 (d, J=2.8 Hz, 1H), 3.94-3.88 (m, 3H), 3.87-3.82 (m, 2H), 3.81-3.71 (m, 2H), 3.18-3.09 (m, 4H). hGal3 IC$_{50}$=0.39 μM.

Example 10. Synthesis of 6-(4-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)piperazin-1-yl)benzo[d]oxazol-2(3H)-one

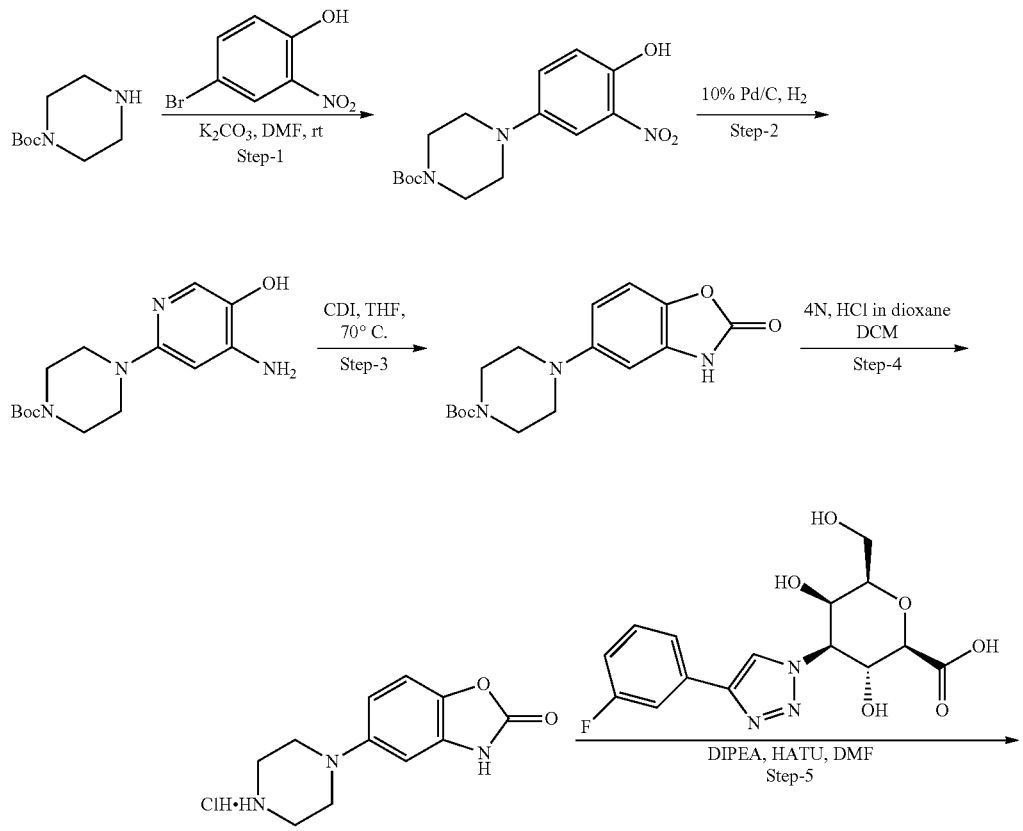

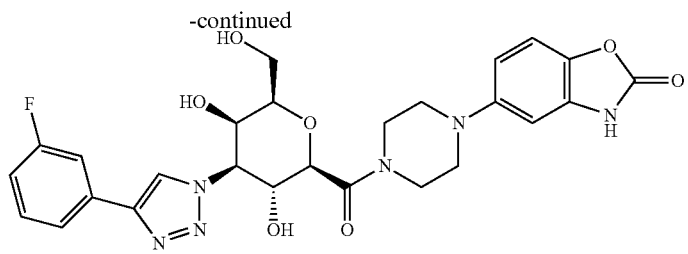

Step-1. Synthesis of tert-butyl 4-(3-hydroxy-4-nitrophenyl)piperazine-1-carboxylate: To a solution of 5-fluoro-2-nitrophenol (0.5 g, 3.18 mmol) in DMF (5 mL), tert-butyl piperazine-1-carboxylate (1.186 g, 6.37 mmol) and $K_2CO_3$ (0.880 g, 6.37 mmol) were added sequentially at room temperature and the reaction mixture was heated at 80° C. for overnight. The reaction mixture was cooled to room temperature, quenched with ice cold water and extracted with EtOAc (3×50 mL). The combined organic extracts were washed with water, brine, dried over sodium sulphate and concentrated under reduced pressure to give crude residue. The crude residue was purified by flash chromatography (24 g, silicagel) and eluted with 60-80% EtOAc in n-hexane to afford tert-butyl 4-(3-hydroxy-4-nitrophenyl)piperazine-1-carboxylate (0.8 g, 2.474 mmol, 78% yield) as yellow solid. LC/MS [M+18]$^+$=346.4, (Method E: $t_R$=1.39 min).

Step-2. Synthesis of tert-butyl 4-(4-amino-3-hydroxyphenyl)piperazine-1-carboxylate: To a degassed stirred solution tert-butyl 4-(3-hydroxy-4-nitrophenyl) piperazine-1-carboxylate (200 mg, 0.62 mmol) in EtOAc (20 mL) was added 10% Pd/C (132 mg, 0.12 mmol) under Nitrogen. Then the reaction mixture was stirred under $H_2$ atm at ambient temperature for 2 h. The reaction mixture was filtered through Celite pad, washed with EtOAc (40 mL) and filtrate was evaporated under reduced pressure to afford tert-butyl 4-(4-amino-3-hydroxyphenyl)piperazine-1-carboxylate as a wine red solid (170 mg, 94%) which was as such taken for next step without further purification. $^1$H NMR (300 MHz, DMSO-d$_6$) δ ppm 6.49 (d, J=8.3 Hz, 1H), 6.35 (d, J=2.6 Hz, 1H), 6.21 (dd, J=8.3, 2.6 Hz, 1H), 3.39 (d, J=4.5 Hz, 4H), 2.83-2.75 (m, 4H), 1.41-1.35 (s, 9H).

Step-3. Synthesis of tert-butyl 4-(2-oxo-2,3-dihydrobenzo[d]oxazol-6-yl)piperazine-1-carboxylate: Prepared in a similar fashion as described in Example 9, Step-3 using tert-butyl 4-(4-amino-3-hydroxyphenyl)piperazine-1-carboxylate (80 mg, 0.27 mmol) and the crude product was purified by flash chromatography (0-60% EtOAc in n-hexane) to afford tert-butyl 4-(2-oxo-2,3-dihydrobenzo[d]oxazol-6-yl)piperazine-1-carboxylate (60 mg, 42% yield). LC/MS [M+H]$^+$=320.2, (Method C: $t_R$=2.113 min). $^1$H NMR (400 MHz, DMSO-d$_6$) δ ppm 11.34 (s, 1H), 6.99 (s, 1H), 6.94 (d, J=8.3 Hz, 1H), 6.74 (dd, J=8.5, 2.1 Hz, 1H), 3.49-3.40 (m, 4H), 3.06-2.96 (m, 4H), 1.41 (s, 9H).

Step-4. Synthesis of 6-(piperazin-1-yl)benzo[d]oxazol-2(3H)-one TFA salt: To a solution of tert-butyl 4-(2-oxo-2,3-dihydrobenzo[d]oxazol-6-yl)piperazine-1-carboxylate (20 mg, 0.06 mmol) in DCM (1 mL) was added trifluoroacetic acid (1 mL, 12.98 mmol) and stirred at room temperature for 1 h. Then the solvent was removed under reduced pressure and triturated with pentane to give 6-(piperazin-1-yl)benzo[d]oxazol-2(3H)-one TFA salt (18 mg, 86% yield) as a wine red solid. LC/MS [M+H]$^+$=220, (Method F: $t_R$=2.020 min, ELSD detector).

Step-5. Synthesis of 6-(4-(((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)piperazin-1-yl)benzo[d]oxazol-2(3H)-one: Prepared in a similar fashion as described in Example 1 using 6-(piperazin-1-yl)benzo[d]oxazol-2(3H)-one TFA salt (16.9 mg, 0.05 mmol) and (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (15 mg, 0.04 mmol). The crude product was purified by preparative HPLC (Method F) to yielded Example 10 as an off white solid (1.5 mg, 6% yield). LC-MS, [M+H]±=555.2. LCMS Conditions—Method F, $t_R$=0.892 min. $^1$H NMR (400 MHz, MEOH-d$_4$) δ ppm 8.54 (s, 1H), 7.72-7.67 (m, 1H), 7.66-7.61 (m, 1H), 7.48 (m, 1H), 7.13-7.06 (m, 1H), 7.02-6.98 (m, 2H), 6.87 (dd, J=8.5, 2.0 Hz, 1H), 4.95 (dd, J=11.0, 3.0 Hz, 1H), 4.73 (dd, J=10.8, 9.3 Hz, 1H), 4.43 (d, J=9.0 Hz, 1H), 4.17 (d, J=3.0 Hz, 1H), 3.94-3.88 (m, 3H), 3.87-3.82 (m, 2H), 3.81-3.71 (m, 2H), 3.24-3.12 (m, 4H). hGal3 IC$_{50}$=0.49 μM.

Example 11. Synthesis of ((2R, 3R, 4S, 5R, 6R)-4-(4-(3-fluorophenyl)-1H-1,2,3-triazol-1-yl)-5-hydroxy-6-(hydroxymethyl)-3-methoxytetrahydro-2H-pyran-2-yl)(4-(4-methoxyphenyl) piperazin-1-yl) methanone

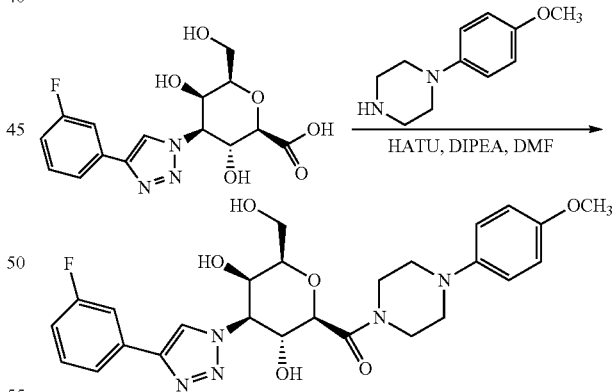

To a stirred solution of (2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-carboxylic acid (20 mg, 0.054 mmol) in DMF (2 mL), DIPEA (0.1 mL, 0.544 mmol), HATU (51.8 mg, 0.136 mmol) and 1-(4-methoxyphenyl)piperazine (10.47 mg, 0.054 mmol) were added sequentially at room temperature and stirred for overnight. The solvent was removed under reduced pressure and crude was purified by prep-HPLC [Method A] to give ((2R,3R,4S,5R,6R)-4-(4-(3-fluorophenyl)-1H-1,2,3-triazol-1-yl)-5-hydroxy-6-(hydroxymethyl)-3-methoxytetrahydro- 2H-pyran-2-yl)(4-(4-methoxyphenyl)piperazin-1-yl)methanone (8.3 mg, 0.015 mmol, 28.1% yield). LC-MS, [M+H]+= 542.1, [$t_R$=1.710 min, Method A]. $^1$H NMR (400 MHz, MEOH-$d_4$) δ ppm 8.70 (s, 1H), 7.69 (d, J=7.6 Hz, 1H), 7.63 (d, J=10.3 Hz, 1H), 7.46 (d, J=6.1 Hz, 1H), 7.08 (d, J=2.4 Hz, 1H), 7.02-6.94 (m, 2H), 6.88-6.82 (m, 2H), 4.96 (dd, J=10.4, 2.4 Hz, 1H), 4.47-4.35 (m, 2H), 4.10 (d, J=2.7 Hz, 1H), 3.93-3.82 (m, 4H), 3.80-3.66 (m, 6H), 3.17-3.06 (m, 7H). hGal3 IC$_{50}$=0.30 µM.

Example 12. Synthesis of ((2R, 3R, 4S, 5R, 6R)-4-(4-(3-fluorophenyl)-1H-1,2,3-triazol-1-yl)-5-hydroxy-6-(hydroxymethyl)-3-methoxytetrahydro-2H-pyran-2-yl)(4-(5-hydroxypyridin-2-yl) piperazin-1-yl) methanone

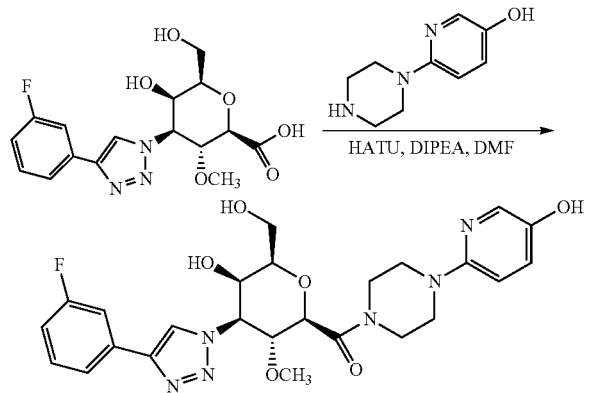

Prepared in a similar fashion as described in Example 11 by using 6-(piperazin-1-yl)pyridin-3-ol (9.76 mg, 0.054 mmol) and (2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-carboxylic acid (20 mg, 0.054 mmol). The crude product was purified by preparative HPLC [Method-B] to give Example 12 (14.5 mg, 0.027 mmol, 50.4% yield) as an off white solid). LC-MS, [M+H]+= 529.1, [$t_R$=1.326 min, Method A]. $^1$H NMR (400 MHz, MEOH-$d_4$) δ ppm 8.71 (s, 1H), 7.79 (d, J=2.8 Hz, 1H), 7.70 (d, J=7.6 Hz, 1H), 7.64 (d, J=10.3 Hz, 1H), 7.51-7.45 (m, 1H), 7.20-7.09 (m, 2H), 6.82 (d, J=8.8 Hz, 1H), 5.00-4.94 (m, 1H, obscured with moisture peak), 4.47-4.38 (m, 2H), 4.11 (d, J=2.7 Hz, 1H), 3.93-3.67 (m, 7H), 3.50-3.30 (m, 4H), 3.12 (s, 3H). hGal3 IC$_{50}$=0.47 µM.

Example 13. Synthesis of ((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)(4-(4-hydroxyphenyl)piperazin-1-yl)methanone

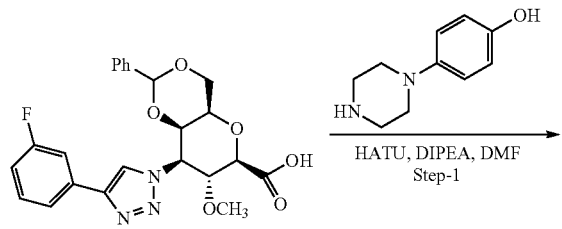

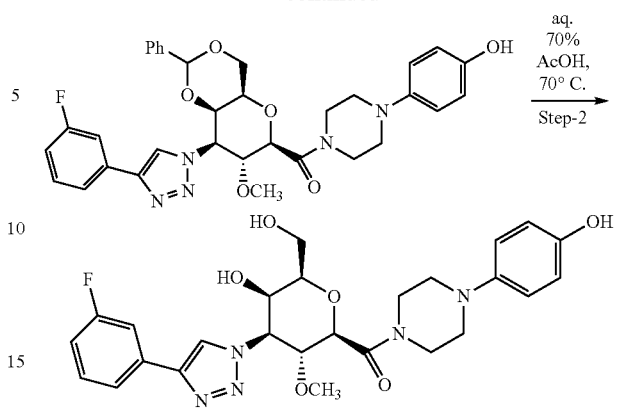

Step-1. Synthesis of ((4aR,6R,7R,8R,8aR)-8-(4-(3-fluorophenyl)-1H-1,2,3-triazol-1-yl)-7-methoxy-2-phenylhexahydropyrano[3,2-d][1,3]dioxin-6-yl)(4-(4-hydroxyphenyl)piperazin-1-yl)methanone: To a solution of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (60 mg, 0.132 mmol) in DMF (1.5 mL) was added DIPEA (0.069 mL, 0.395 mmol) and HATU (75 mg, 0.198 mmol) and stirred for 5 min. Then 4-(piperazin-1-yl)phenol (23.48 mg, 0.132 mmol) was added and stirred for 2 h at room temperature. The reaction mixture was quenched with ice cold water (20 mL) and stirred for 15 min. The obtained solid was filtered, residue was washed with excess water and dried to afford ((4aR,6R,7R,8R,8aR)-8-(4-(3-fluorophenyl)-1H-1,2,3-triazol-1-yl)-7-methoxy-2-phenylhexahydropyrano[3,2-d][1,3]dioxin-6-yl)(4-(4-hydroxyphenyl)piperazin-1-yl)methanone (73 mg, 0.11 mmol, 80% yield) as off white solid. LC-MS, [M+H]+=616.2, [$t_R$=1.970 min, Method F].

Step-2. (2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)(4-(4-hydroxyphenyl)piperazin-1-yl)methanone: ((4aR,6R,7R,8R,8aR)-8-(4-(3-fluorophenyl)-1H-1,2,3-triazol-1-yl)-7-methoxy-2-phenylhexahydropyrano[3,2-d][1,3]dioxin-6-yl)(4-(4-hydroxyphenyl)piperazin-1-yl)methanone (73 mg, 0.119 mmol) was suspended in acetic acid (70% solution in water) (5 mL) and heated at 70° C. for 16 h. The reaction mixture was cooled to room temperature, solvent was removed under reduced pressure to give crude residue. The crude residue was purified by Prep-HPLC [Method B] to afford ((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)(4-(4-hydroxyphenyl)piperazin-1-yl)methanone (26 mg, 0.049 mmol, 41% yield). LC-MS, [M+H]+=528.2, [$t_R$=1.092 min, Method F]. $^1$H NMR (400 MHz, MEOH-$d_4$) δ ppm 8.73 (s, 1H), 7.75-7.70 (m, 1H), 7.69-7.63 (m, 1H), 7.48 (td, J=8.2, 5.8 Hz, 1H), 7.14-7.07 (m, 1H), 6.95-6.89 (m, 2H), 6.78-6.72 (m, 2H), 5.03-4.94 (m, 1H), 4.49-4.40 (m, 2H), 4.12 (d, J=2.0 Hz, 1H), 3.94-3.84 (m, 4H), 3.83-3.69 (m, 3H), 3.17-3.09 (m, 5H), 3.08-3.03 (m, 2H). hGal3 IC$_{50}$=0.15 µM.

The Examples in Table 2 were prepared in an analogous fashion to Examples 13, substituting 4-(piperazin-1-yl)phenol with the appropriate piperazine fragments in the synthetic sequence.

US 12,286,424 B2

33 34

TABLE 2

| EX # | Structure (Synthetic Method A) | LCMS/$t_R$ (min); $^1$H NMR (400 MHz, methanol-$d_4$) | hGal-3 IC$_{50}$ (μM) |
|---|---|---|---|
| 14 | | (M + H)$^+$ = 565.3/1.79; δ ppm 8.73 (s, 1H), 7.75-7.70 (m, 1H), 7.69-7.64 (m, 1H), 7.52-7.44 (m, 1H), 7.40-7.34 (m, 1H), 7.32-7.28 (m, 1H), 7.18-7.06 (m, 3H), 5.04-4.97 (m, 1H), 4.51-4.43 (m, 2H), 4.13 (d, J = 2.7 Hz, 1H), 4.03-3.92 (m, 3H), 3.91-3.71 (m, 7H), 3.29-3.21 (m, 3H), 3.15 (s, 3H), [1H might be obscured with moisture peak] | 0.41 |
| 15 | | (M + H)$^+$ = 568.2/1.71; δ ppm 8.78-8.58 (m, 1H), 7.77-7.61 (m, 2H), 7.54-7.42 (m, 1H), 7.19-7.05 (m, 1H), 6.76-6.65 (m, 1H), 6.39-6.27 (m, 1H), 6.13-6.03 (m, 1H), 5.86-5.80 (m, 2H), 5.09-4.92 (m, 2H), 4.60-4.28 (m, 3H), 4.14-4.06 (m, 1H), 3.95-3.88 (m, 1H), 3.84-3.72 (m, 2H), 3.70-3.63 (m, 1H), 3.62-3.49 (m, 2H), 3.22-2.97 (m, 6H), 2.23-1.95 (m, 2H). | 0.20 |
| 16 | | (M + H)$^+$ = 554.2/1.684; δ ppm 8.71-8.60 (m, 1H), 7.72-7.56 (m, 2H), 7.51-7.41 (m, 1H), 7.12-7.04 (m, 1H), 6.86-6.76 (m, 2H), 6.67-6.52 (m, 2H), 5.01-4.92 (m, 1H), 4.41-4.30 (m, 1H), 4.21-4.08 (m, 2H), 4.03 (d, J = 2.9 Hz, 1H), 4.00-3.83 (m, 3H), 3.82-3.62 (m, 6H), 3.61-3.46 (m, 2H), 3.11-2.57 (m, 1H), 2.13 (d, J = 8.8 Hz, 1H), 2.01 (br. s., 1H), 1.40-1.27 (m, 2H). | 0.530 |
| 17 | | (M + H)$^+$ = 568.2/1.679; δ ppm 8.70-8.62 (m, 1H), 7.72-7.58 (m, 2H), 7.51-7.43 (m, 1H), 7.08 (d, J = 8.6 Hz, 1H), 6.66 (dd, J = 19.7, 8.4 Hz, 1H), 6.35-6.27 (m, 1H), 6.10-6.00 (m, 1H), 5.84-5.75 (m, 1H), 5.02-4.90 (m, 1H), 4.48 (d, J = 7.1 Hz, 1H), 4.42-4.32 (m, 2H), 4.25-4.12 (m, 1H), 4.07 (dd, J = 19.6, 2.4 Hz, 1H), 3.98-3.85 (m, 1H), 3.84-3.61 (m, 4H), 3.58 (d, J = 11.0 Hz, 1H), 3.53-3.48 (m, 1H), 3.16-2.66 (s, 3H), 2.17-1.96 (m, 2H). | 0.311 |

Example 18. Synthesis of 4-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)-N-(4-hydroxyphenyl)piperazine-1-carboxamide

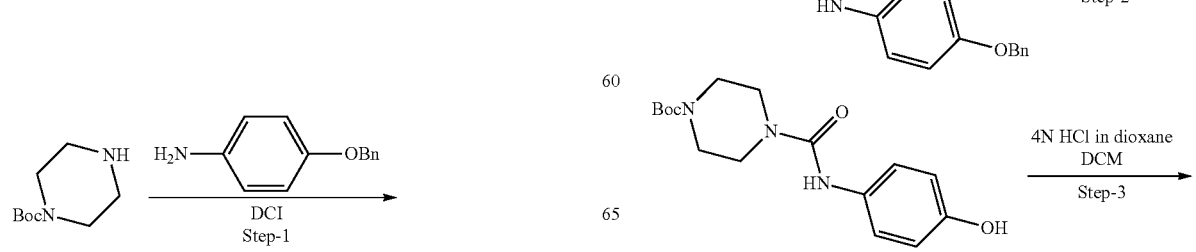

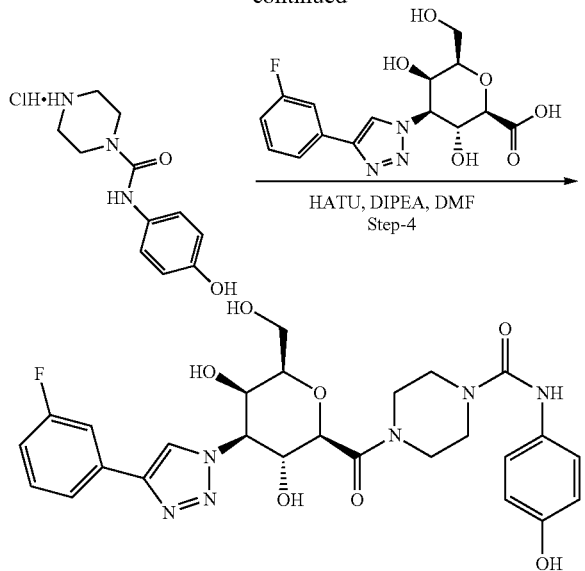

Step-1. Synthesis of tert-butyl 4-((4-(benzyloxy)phenyl) carbamoyl)piperazine-1-carboxylate: To a stirred solution of 4-(benzyloxy)aniline (0.8 g, 4.02 mmol) in DCM (10 mL). 1,1'-carbonyldiimidazole (1.107 g, 6.83 mmol) was added and stirred for 14 h at room temperature. Then tert-butyl piperazine-1-carboxylate (1.271 g, 6.83 mmol) was added and stirred for another 14 h. Reaction mixture was diluted with DCM (20 mL), filtered through Celite pad and washed with excess of DCM. Filtrate was washed with water (2×50 mL), brine, dried over sodium sulphate and solvent was removed under reduced pressure to give the crude product. The crude product was purified by flash chromatography (20-60% EtOAc and hexane) to afford tert-butyl 4-((4-(benzyloxy)phenyl)carbamoyl)piperazine-1-carboxylate (0.24 g, 0.560 mmol, 14% yield) as a pale brown solid. LC/MS [M+H]$^+$=412.2, (Method C: $t_R$=2.88 min). $^1$H NMR (400 MHz, CDCl$_3$): δ ppm 7.45-7.30 (m, 5H), 7.27-7.21 (m, 2H), 6.95-6.89 (m, 2H), 6.21 (s, 1H), 5.04 (s, 2H), 3.53-3.44 (m, 8H), 1.48 (s, 9H).

Step-2. Synthesis of tert-butyl 4-((4-hydroxyphenyl)carbamoyl)piperazine-1-carboxylate: To a stirred solution of tert-butyl 4-((4-(benzyloxy)phenyl)carbamoyl) piperazine-1-carboxylate (0.15 g, 0.365 mmol) in MeOH (5 mL). Pd/C (10% on carbon) (0.039 g, 0.036 mmol) was added and stirred under hydrogen atm (~1 atm) for 2 h. Reaction mass filtered through Celite pad, washed with excess of MeOH and filtrate was concentrated under reduced pressure to afford tert-butyl 4-((4-hydroxyphenyl)carbamoyl) piperazine-1-carboxylate (0.07 g, 0.213 mmol, 58.6% yield) as a white solid which was as such taken for next step without further purification. LC/MS [M+H]$^+$=322.2, (Method C: $t_R$=1.99 min).

Step-3. Synthesis of N-(4-hydroxyphenyl) piperazine-1-carboxamide, HCl: To an ice cooled stirred solution of tert-butyl 4-((4-hydroxyphenyl)carbamoyl)piperazine-1-carboxylate (0.07 g, 0.218 mmol) in DCM (1 mL), 4N HCl in dioxane (0.5 mL, 2.000 mmol) was added and stirred for 2 h. Solvent was removed under reduced pressure and dried to afford N-(4-hydroxyphenyl) piperazine-1-carboxamide, HCl (0.04 g, 0.155 mmol, 71.3% yield) as a pale yellow solid which was as such taken for next step without further purification. LC/MS [M+H]$^+$=222.2, (Method C: $t_R$=0.38 min).

Step-4: Synthesis of 4-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)-N-(4-hydroxyphenyl)piperazine-1-carboxamide: To a stirred solution of Then (2R,3R,4S,5R,6R)-4-(4-(3-fluorophenyl)-1H-1,2,3-triazol-1-yl)-3,5-dihydroxy-6-(hydroxymethyl) tetrahydro-2H-pyran-2-carboxylic acid (0.02 g, 0.057 mmol) in DMF (2 mL), DIPEA (0.5 mL, 2.86 mmol), HATU (0.054 g, 0.142 mmol) and of N-(4-hydroxyphenyl)piperazine-1-carboxamide, HCl (0.029 g, 0.113 mmol) were added sequentially at room temperature and stirred overnight. The solvent was removed under reduced pressure and crude was purified by prep-HPLC [Method B] to give Example 18 (8.3 mg, 0.015 mmol, 28.1% yield). LC-MS, [M+H]$^+$=557.0, [$t_R$=1.12 min, Method A]. $^1$H NMR (400 MHz, MEOH-d$_4$) δ ppm 8.54 (s, 1H), 7.70-7.62 (m, 2H), 7.50-7.45 (m, 1H), 7.16-7.08 (m, 3H), 6.72 (d, J=8.8 Hz, 2H), 4.93 (dd, J=10.8, 2.7 Hz, 1H), 4.72 (dd, J=10.4, 9.6 Hz, 1H), 4.39 (d, J=9.2 Hz, 1H), 4.14 (d, J=2.9 Hz, 1H), 3.92-3.87 (m, 1H), 3.83-3.69 (m, 6H), 3.62-3.51 (m, 4H). hGal3 IC$_{50}$=0.25 µM.

Example 19. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl) ((1S,4S)-5-(4-methoxyphenyl)-2,5-diazabicyclo [2.2.1]heptan-2-yl)methanone

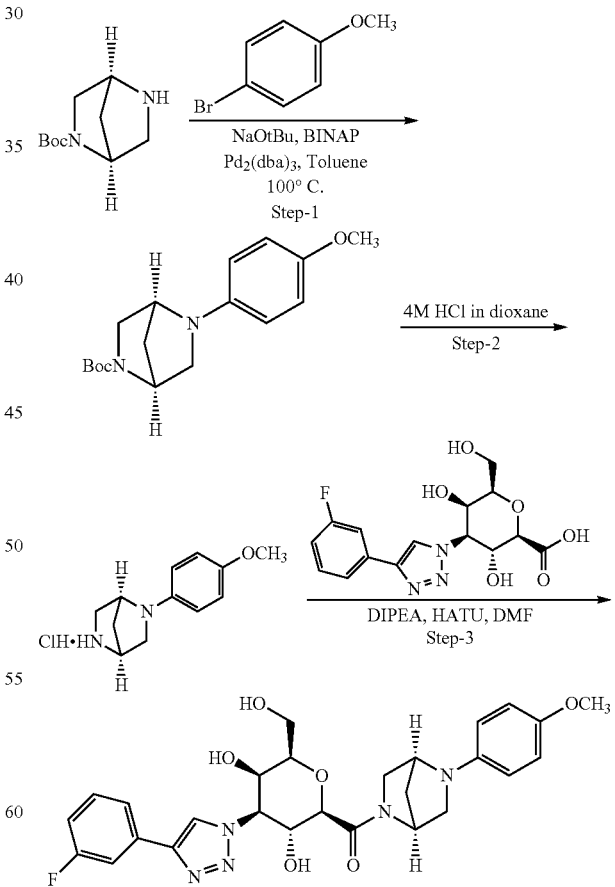

Step-1. Synthesis of (1S,4S)-tert-butyl 5-(4-methoxyphenyl)-2,5-diazabicyclo[2.2.1]heptane-2-carboxylate: Dried vial was charged with (1S,4S)-tert-butyl 2,5-diazabicyclo

[2.2.1]heptane-2-carboxylate (0.2 g, 1.009 mmol), 1-bromo-4-methoxybenzene (0.283 g, 1.513 mmol), sodium tert-butoxide (0.291 g, 3.03 mmol), BINAP (0.126 g, 0.202 mmol), Toluene (5 mL) and reaction mixture was degassed nitrogen for 10 min. Then $Pd_2(dba)_3$ (0.092 g, 0.101 mmol) was added, vial was sealed and heated at 100° C. for overnight. The reaction mixture was cooled to room temperature, filtered through Celite pad, washed with excess and filtrate was concentrated under reduced pressure to give crude residue. The crude residue was purified by flash chromatography (45-65% EtOAc in n-hexane) to afford (1S,4S)-tert-butyl 5-(4-methoxyphenyl)-2,5-diazabicyclo[2.2.1]heptane-2-carboxylate (0.12 g, 0.394 mmol, 39.1% yield). LC/MS $[M+H]^+$=305.1, $t_R$=0.97 min (Method D).

Step-2. Synthesis of (1S,4S)-2-(4-methoxyphenyl)-2,5-diazabicyclo[2.2.1]heptane, HCl: To an ice cooled stirred solution of (1S,4S)-tert-butyl 5-(4-methoxyphenyl)-2,5-diazabicyclo[2.2.1]heptane-2-carboxylate (0.11 g, 0.361 mmol) in DCM (2 mL), 4M HCl in dioxane (0.903 mL, 3.61 mmol) was added. The reaction mixture was allowed to reach room temperature and stirred for 2 h. Solvent was removed under reduced pressure, washed with 10 mL diethylether+1 mL of MeOH and dried to afford (1S,4S)-2-(4-methoxyphenyl)-2,5-diazabicyclo[2.2.1]heptane, HCl (0.075 g, 0.312 mmol, 86% yield) as a brown gummy solid. LC/MS $[M+H]^+$=205.5, $t_R$=0.64 min (Method E).

Step-3. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((1S,4S)-5-(4-methoxyphenyl)-2,5-diazabicyclo[2.2.1]heptan-2-yl)methanone: To a stirred solution of (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.015 g, 0.042 mmol) in DMF (1.0 mL), (1S,4S)-2-(4-methoxyphenyl)-2,5-diazabicyclo[2.2.1]heptane hydrochloride (0.020 g, 0.085 mmol), DIPEA (0.074 mL, 0.425 mmol) and HATU (0.040 g, 0.106 mmol) were added sequentially at room temperature and stirred overnight. The solvent was removed under reduced pressure and crude residue was purified by prep-HPLC [Method A] to afford Example 19 (0.075 g, 0.312 mmol, 86% yield). LC/MS $[M+H]^+$=540.2, $t_R$=1.81 min (Method C). $^1$H NMR (400 MHz, MEOH-$d_4$) δ ppm 8.65-8.31 (m, 1H), 7.72-7.54 (m, 2H), 7.51-7.41 (m, 1H), 7.13-7.01 (m, 1H), 6.88-6.76 (m, 2H), 6.68-6.53 (m, 2H), 5.10-4.87 (m, 2H), 4.66-4.45 (m, 2H), 4.32-4.03 (m, 2H), 3.93-3.46 (m, 9H), 3.19-3.07 (m, 1H), 2.21-1.89 (m, 2H). hGal3 $IC_{50}$=0.25 µM.

The Examples in Table 3 were prepared in an analogous fashion to Examples 19, substituting 1-bromo-4-methoxybenzene with the appropriate aryl bromide in the synthetic sequence.

TABLE 3

| EX # | Structure (Synthetic Method) | LCMS/$t_R$ (min); $^1$H NMR (400 MHz, methanol-$d_4$) | hGal-3 $IC_{50}$ (µM) |
|---|---|---|---|
| 20 | 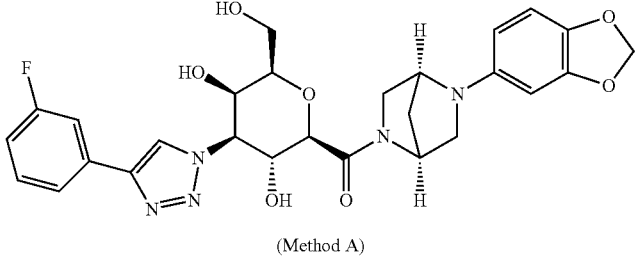 [SMILES: O=C([C@@H]1O[C@H](CO)[C@H](O)[C@H](n2cc(-c3cccc(F)c3)nn2)[C@H]1O)N1C[C@@H]2C[C@H]1CN2c1ccc2c(c1)OCO2] (Method A) | $(M + H)^+$ = 554.3/1.23; δ ppm (d, J = 13.05 Hz, 1 H) 7.65-7.72 (m, 1 H) 7.62 (d, J = 10.04 Hz, 1 H) 7.47 (tdd, J = 8.03, 8.03, 6.02, 2.01 Hz, 1 H) 7.09 (t, J = 8.53 Hz, 1 H) 6.69 (dd, J = 19.07, 8.53 Hz, 1 H) 6.32 (dd, J = 10.79, 2.26 Hz, 1 H) 6.06 (td, J = 8.41, 2.26 Hz, 1 H) 5.84 (s, 1 H) 5.76-5.82 (m, 1 H) 4.91-4.95 (m, 2 H) 4.44-4.68 (m, 3 H) 4.32 (d, J = 9.54 Hz, 1 H) 4.04-4.18 (m, 2 H) 3.87-3.97 (m, 1 H) 3.70-3.83 (m, 2 H) 3.51-3.70 (m, 5 H) 2.12-2.20 (m, 1 H) 2.01-2.12 (m, 1 H). | 0.249 |
| 21 | 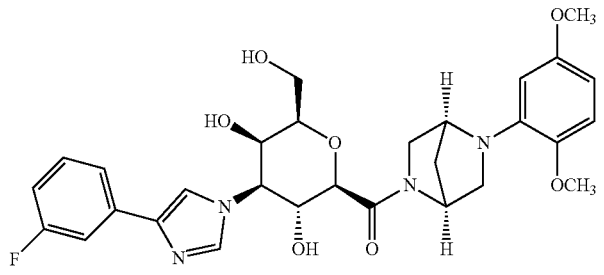 (Method B) | $(M + H)^+$ = 570.3/1.225; δ ppm 8.49 (d, J = 14.05 Hz, 1 H) 7.68 (d, J = 8.53 Hz, 1 H) 7.62 (dt, J = 10.04, 2.01 Hz, 1 H) 7.39-7.52 (m, 1 H) 7.03-7.16 (m, 1 H) 6.83 (dd, J = 16.56, 8.53 Hz, 1 H) 6.25-6.42 (m, 2 H) 5.03 (s, 1 H) 4.89-4.95 (m, 2 H) 4.56-4.68 (m, 3 H) 4.33 (d, J = 9.54 Hz, 1 H) 4.07-4.19 (m, 1 H) 3.88-3.96 (m, 1 H) 3.60-3.84 (m, 11 H) 3.23 (d, J = 10.54 Hz, 1 H) 2.07-2.15 (m, 1 H) 2.04 (br. s., 1 H). | 0.962 |

TABLE 3-continued

| EX # | Structure (Synthetic Method) | LCMS/$t_R$ (min); $^1$H NMR (400 MHz, methanol-$d_4$) | hGal-3 IC$_{50}$ (μM) |
|---|---|---|---|
| 22 | 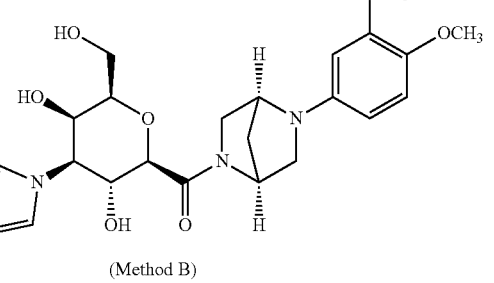 (Method B) | (M + H)$^+$ = 570.1/1.348; δ ppm 8.44-8.54 (m, 1 H) 7.65-7.72 (m, 1 H) 7.62 (dt, J = 9.79, 2.13 Hz, 1 H) 7.47 (tdd, J = 8.16, 8.16, 5.77, 3.01 Hz, 1 H) 7.03-7.14 (m, 1 H) 6.79-6.92 (m, 1 H) 6.31 (dd, J = 12.55, 2.51 Hz, 1 H) 6.18 (td, J = 8.66, 2.76 Hz, 1 H) 5.09 (s, 1 H) 4.96 (s, 1 H) 4.87-4.94 (m, 1 H) 4.58-4.67 (m, 1 H) 4.51-4.58 (m, 1 H) 4.34 (d, J = 9.04 Hz, 1 H) 4.16 (d, J = 2.01 Hz, 1 H) 3.89-3.96 (m, 1 H) 3.86 (s, 1 H) 3.79-3.84 (m, 3H) 3.72- 3.79 (m, 4 H) 3.64-3.70 (m, 1H) 3.56- 3.62 (m, 2 H) 3.48-3.55 (m, 1H) 3.13- 3.17 (m, 1 H) 2.15-2.22 (m, 1H) 2.10 (t, J = 8.78 Hz, 1 H) 1.91-2.00 (m, 1 H). | 0.522 |

Example 23. Synthesis of methyl (4-((1S,4S)-5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)-2,5-diazabicyclo[2.2.1]heptan-2-yl)phenyl)carbamate

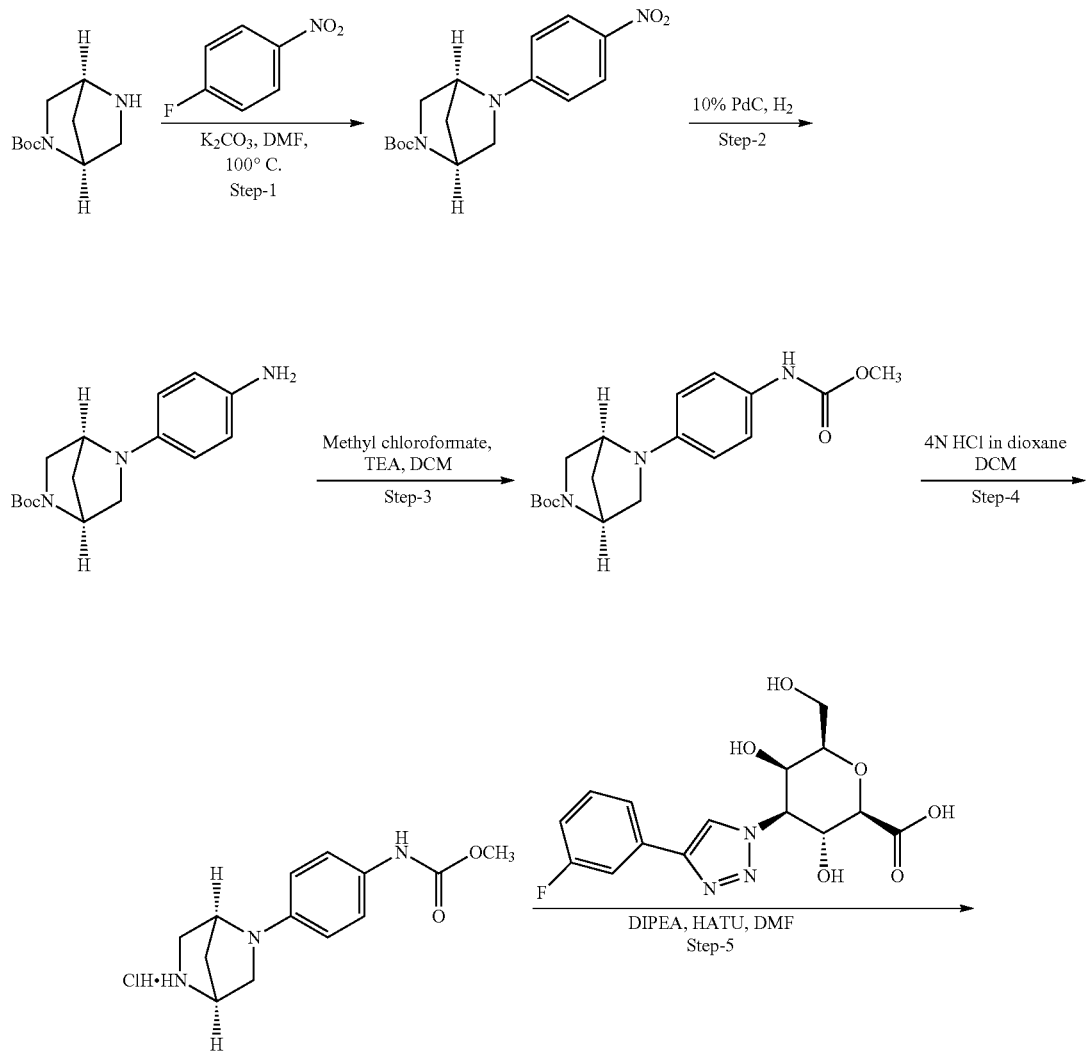

-continued

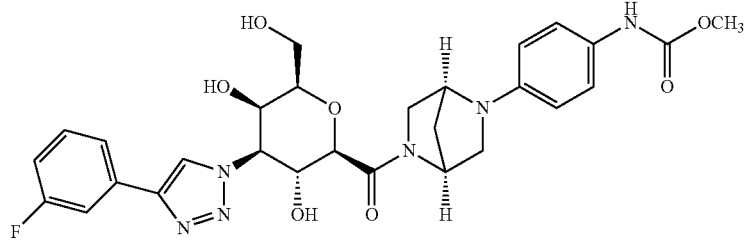

Step-1. Synthesis of (1S,4S)-tert-butyl 5-(4-nitrophenyl)-2,5-diazabicyclo[2.2.1]heptane-2-carboxylate: To a stirred solution of (1S,4S)-tert-butyl 2,5-diazabicyclo[2.2.1]heptane-2-carboxylate (1.405 g, 7.09 mmol) in DMF (5 mL), $K_2CO_3$ (0.98 g, 7.09 mmol) and 1-fluoro-4-nitrobenzene (0.5 g, 3.54 mmol) were added sequentially at room temperature. Then the reaction mixture was heated at 80° C. for overnight. The reaction mixture was cooled to room temperature, extracted with EtOAc (3×50 mL), washed with water, brine, dried over sodium sulphate and concentrated under reduced pressure to give crude residue. The crude residue was purified by flash chromatography (45-65% EtOAc in n-hexane) to afford (1S,4S)-tert-butyl 5-(4-nitrophenyl)-2,5-diazabicyclo[2.2.1]heptane-2-carboxylate (0.8 g, 2.505 mmol, 70.7% yield) as a yellow solid. LC/MS [M+H]$^+$=320.1, $t_R$=1.28 min (Method E). $^1$H NMR (300 MHz, CHLOROFORM-d) δ ppm 8.15 (d, J=9.1 Hz, 2H), 6.51 (d, J=9.1 Hz, 2H), 4.50-4.80 (m, 2H), 3.61 (br d, J=9.1 Hz, 1H), 3.27-3.54 (m, 3H), 2.03 (br s, 2H), 1.46, 1.48*(s, 9H) (*rotameric mixture).

Step-2. Synthesis of (1S,4S)-tert-butyl 5-(4-aminophenyl)-2,5-diazabicyclo[2.2.1]heptane-2-carboxylate: To a degassed solution (1S,4S)-tert-butyl 5-(4-nitrophenyl)-2,5-diazabicyclo[2.2.1]heptane-2-carboxylate (0.5 g, 1.566 mmol) in THF/EtOH (1:1, 20 mL), was added palladium on carbon (10% w/w, 50% wet) (0.17 g, 0.157 mmol) and stirred the mixture at rt under hydrogen pressure (~1 atm) for 12 h. The reaction mixture was filtered through Celite pad, washed with excess EtOAc/MeOH (1:1, 30 mL) and filtrate was concentrated under reduced pressure to give the (1S,4S)-tert-butyl 5-(4-aminophenyl)-2,5-diazabicyclo[2.2.1]heptane-2-carboxylate (0.4 g, 1.382 mmol, 88% yield) as an off-white solid. LC/MS [M+H]$^+$=290.1, (Method E: $t_R$=1.04 min).

Step-3. Synthesis of (1S,4S)-tert-butyl 5-(4-((methoxycarbonyl)amino)phenyl)-2,5-diazabicyclo[2.2.1]heptane-2-carboxylate: To an ice cooled stirred solution of (1S,4S)-tert-butyl 5-(4-aminophenyl)-2,5-diazabicyclo[2.2.1]heptane-2-carboxylate (0.1 g, 0.346 mmol) in DCM (3 mL), DIPEA (0.181 mL, 1.037 mmol) and methyl chloroformate (0.028 mL, 0.363 mmol) were added sequentially under nitrogen. Reaction mixture was allowed to reach room temperature and stirred for 2 h. Then the reaction mixture was extracted with DCM (3×30 mL), washed with water (30 mL), brine (30 mL). The combined organic extracts were dried over sodium sulphate and solvent was removed under reduced pressure to give the crude residue. The crude residue was purified by flash chromatography (45-65% EtOAc in n-hexane) to afford (1S,4S)-tert-butyl 5-(4-((methoxycarbonyl)amino)phenyl)-2,5-diazabicyclo[2.2.1]heptane-2-carboxylate (0.08 g, 0.230 mmol, 66.6% yield) as an off-white solid. LC/MS [M+H]$^+$=348.2, (Method C: $t_R$=2.465 min).

Step-4. Synthesis of methyl (4-((1S,4S)-2,5-diazabicyclo[2.2.1]heptan-2-yl)phenyl)carbamate hydrochloride: To an ice cooled stirred solution of (1S,4S)-tert-butyl 5-(4-((methoxycarbonyl)amino)phenyl)-2,5-diazabicyclo[2.2.1]heptane-2-carboxylate (0.05 g, 0.144 mmol) in DCM (2 mL), 4M HCl in dioxane (0.36 mL, 1.44 mmol) was added. The reaction mixture was allowed to reach room temperature and stirred for 2 h. Solvent was removed under reduced pressure and dried to afford methyl (4-((1S,4S)-2,5-diazabicyclo[2.2.1]heptan-2-yl)phenyl)carbamate hydrochloride (0.035 g, 0.123 mmol, 86% yield) as an off-white solid. LC/MS [M+H]$^+$=248.1, (Method E: $t_R$=0.46 min). $^1$H NMR (400 MHz, DMSO-$d_6$) δ ppm 9.18-9.55 (m, 2H), 8.68-9.00 (m, 1H), 7.24-7.33 (m, 2H), 6.58-6.62 (m, 2H), 4.54 (s, 1H), 4.38-4.42 (m, 1H), 3.62 (s, 3H), 3.56-3.58 (m, 1H), 3.21 (br d, J=10.5 Hz, 2H), 3.08-3.16 (m, 1H), 2.11 (br d, J=10.0 Hz, 1H), 1.92 (br d, J=11.0 Hz, 1H).

Step-5. Synthesis of methyl (4-((1S,4S)-5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)-2,5-diazabicyclo[2.2.1]heptan-2-yl)phenyl)carbamate: To a stirred solution of (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.02 g, 0.057 mmol) in DMF (1.0 mL), methyl (4-((1S,4S)-2,5-diazabicyclo[2.2.1]heptan-2-yl)phenyl)carbamate hydrochloride (0.032 g, 0.113 mmol DIPEA (0.099 mL, 0.566 mmol) and HATU (0.054 g, 0.142 mmol) were added sequentially at room temperature and stirred for overnight. The solvent was removed under reduced pressure and crude residue was purified by prep-HPLC [Method A] to afford Example 23 (0.012 g, 0.02 mmol, 36% yield). LC/MS [M+H]$^+$=583.4, $t_R$=1.14 min (Method A). 1H NMR (400 MHz, MEOH-$d_4$) δ ppm 8.59-8.44 (m, 1H), 7.78-7.58 (m, 2H), 7.55-7.41 (m, 1H), 7.35-7.06 (m, 3H), 6.75-6.54 (m, 2H), 4.78-4.49 (m, 3H), 4.42-4.04 (m, 3H), 4.01-3.44 (m, 10H), 2.26-1.95 (m, 2H) (Mixture of Rotamers). hGal3 $IC_{50}$=0.59 μM.

Example 24. Synthesis of N-(4-((1S,4S)-5-((2R,3R, 4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)-2,5-diazabicyclo[2.2.1]heptan-2-yl)phenyl)methanesulfonamide 4S)-2, 5-diazabicyclo [2.2.1] heptan-2-yl) phenyl) methane sulfonamide hydrochloride (53.5 mg, quantitative) as an off white solid which was as such taken for next step without purification. LC/MS [M+H]$^+$=268.2, (Method C: $t_R$=0.396 min). $^1$H NMR (400 MHz, DMSO-d$_6$) δ ppm 9.14 (s, 1H),

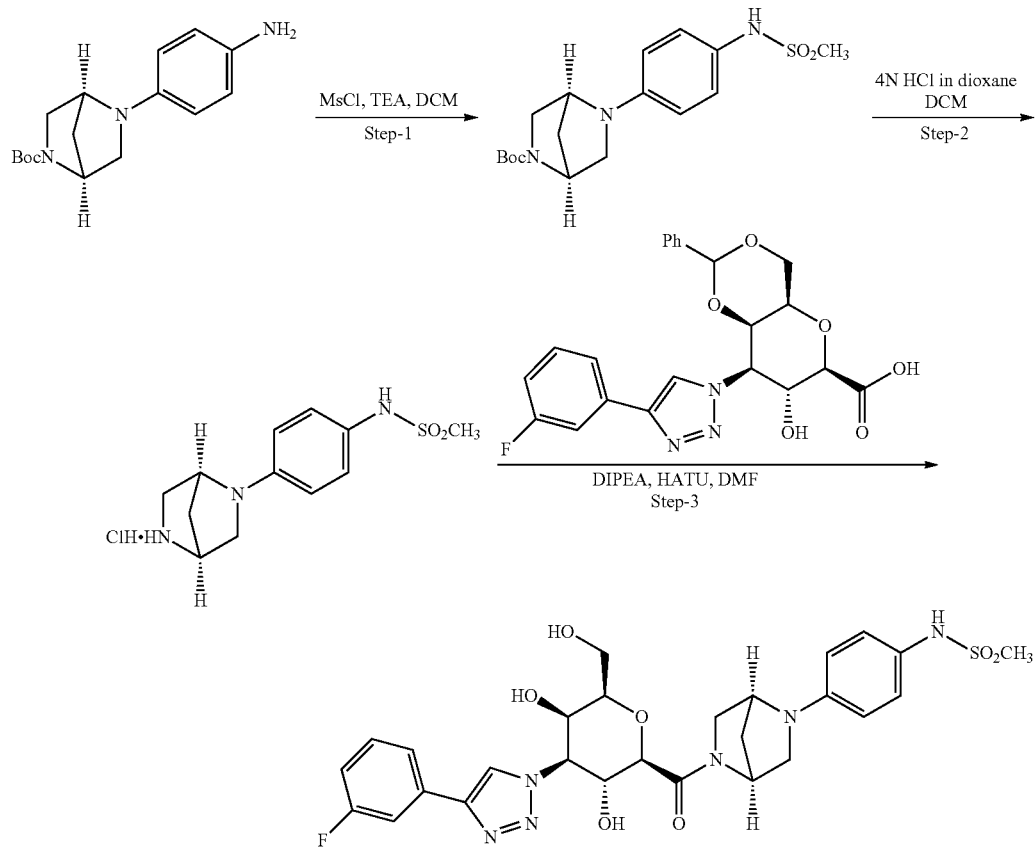

Step-1: Synthesis of (1S,4S)-tert-butyl 5-(4-(methylsulfonamido)phenyl)-2,5-diazabicyclo [2.2.1]heptane-2-carboxylate: To a stirred solution of (1S,4S)-tert-butyl 5-(4-aminophenyl)-2,5-diazabicyclo[2.2.1]heptane-2-carboxylate (120 mg, 0.42 mmol) and triethylamine (0.07 mL, 0.5 mmol) in DCM (10 mL) was added Ms-Cl (0.03 mL, 0.42 mmol) at 0° C. The reaction mixture was allowed to reach room temperature and stirred for 2 h. The reaction mixture was extracted with DCM (20 mL), washed with water (10 mL), brine (10 mL), dried (Na$_2$SO$_4$) and concentrated under reduced pressure to give crude residue. The crude residue was purified by flash chromatography (0-50% EtOAc in n-hexane) to afford (1S,4S)-tert-butyl 5-(4-(methylsulfonamido)phenyl)-2,5-diazabicyclo [2.2.1]heptane-2-carboxylate as a brown solid (68 mg, 43% yield). LC/MS [M+H]$^+$=368.2, (Method F: $t_R$=1.788 min). $^1$H NMR (400 MHz, DMSO-d$_6$) δ ppm 9.05 (s, 1H), 7.06-7.03 (d, J=8.8 Hz, 2H), 6.62-6.55 (d, J=9.2 Hz, 2H), 4.48-4.37 (m, 2H), 3.57-3.48 (m, 1H), 3.29-3.15 (m, 2H), 2.94 (m, 1H), 2.84 (s, 3H), 1.91 (m, 2H), 1.39, 1.33 (s, 9H) (Rotameric mixture).

Step-2: Synthesis of N-(4-((1S, 4S)-2, 5-diazabicyclo [2.2.1] heptan-2-yl) phenyl) methane sulfonamide hydrochloride: Prepared in a similar fashion as described in Example 20, Step-4 using afford (1S,4S)-tert-butyl 5-(4-(methylsulfonamido)phenyl)-2,5-diazabicyclo [2.2.1]heptane-2-carboxylate (65 mg, 0.18 mmol) to afford N-(4-((1S, 7.10 (d, J=9.0 Hz, 2H), 6.66-6.61 (m, 2H), 4.59-4.41 (m, 2H), 3.27-3.09 (m, 4H), 2.85 (s, 3H), 2.12 (d, J=10.5 Hz, 1H), 1.92 (d, J=10.5 Hz, 1H).

Step-3. Synthesis of N-(4-((1S,4S)-5-((4aR,6R,7R,8R, 8aR)-8-(4-(3-fluorophenyl)-1H-1,2,3-triazol-1-yl)-7-hydroxy-2-phenylhexahydropyrano[3,2-d][1,3]dioxine-6-carbonyl)-2,5-diazabicyclo [2.2.1]heptan-2-yl)phenyl)methane sulfonamide: To a stirred solution of N-(4-((1S,4S)-2,5-diazabicyclo[2.2.1]heptan-2-yl)phenyl)methanesulfonamide hydrochloride (37.9 mg, 0.125 mmol) in DMF (3.0 mL) was added DIPEA (0.2 mL, 1.133 mmol) and stirred for 10 minutes. Then (2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carboxylic acid (50 mg, 0.113 mmol) and propylphosphonic anhydride (50% solution in EtOAc) (0.44 mL, 0.680 mmol) were added sequentially and stirred for 2 h at room temperature. The reaction mixture was quenched with ice cold water and extracted with 10% MeOH in DCM (4×20 mL). The combined organic extracts were washed with brine, dried over sodium sulphate and concentrated under reduced pressure to give crude residue. The crude residue was purified by flash chromatography (0-5% MeOH in DCM) to afford N-(4-((1S, 4S)-5-((2S,4aR,6R,7R,8R,8aR)-8-(4-(3-fluorophenyl)-1H-1,2,3-triazol-1-yl)-7-hydroxy-2-phenylhexahydropyrano[3, 2-d][1,3]dioxine-6-carbonyl)-2,5-diazabicyclo[2.2.1]

heptan-2-yl)phenyl)methane sulfonamide (63 mg, 71% yield). LC-MS, [M−H]+=691.2, (Method F: $t_R$=1.862 min).

Step-4. Synthesis of N-(4-((1S,4S)-5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)-2,5-diazabicyclo[2.2.1]heptan-2-yl)phenyl)methanesulfonamide: N-(4-((1S,4S)-5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carbonyl)-2,5-diazabicyclo[2.2.1]heptan-2-yl)phenyl)methanesulfonamide (75 mg, 0.109 mmol) was suspended in aq.70% AcOH (7 mL, 122 mmol) and heated at 70° C. for 16 h. The reaction mixture was cooled to room temperature and solvent was removed under reduced pressure to give crude residue. The crude residue was purified by preparative HPLC [Method C] to afford Example 24 (25 mg, 38% yield) as an off-white solid. LC/MS [M+H]+=603.2, $t_R$=1.41 min (Method C). $^1$H NMR (400 MHz, MEOH-$d_4$) δ ppm 8.51, 8.49 (s, 1H), 7.67 (m, 1H), 7.62-7.57 (m, 1H), 7.49-7.41 (m, 1H), 7.18-7.04 (m, 3H), 6.66-6.60 (m, 2H), 5.12, 4.91 (s, 1H), 4.93-4.86 (m, 1H, obscured with moisture peak), 4.66-4.53 (m, 2H), 4.33-4.05 (m, 2H), 3.95-3.63 (m, 4H), 3.59-3.51 (m, 2H), 3.19-3.11 (m, 1H), 2.89-2.82 (m, 3H), 2.21-2.06 (m, 2H) (Mixture of Rotamers). hGal3 IC$_{50}$=0.68 μM.

Example 25: Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((1S,4S)-5-(4-hydroxyphenyl)-2,5-diazabicyclo[2.2.1]heptan-2-yl)methanone Step-1. Synthesis of (1S,4S)-tert-butyl 5-(4-(benzyloxy)phenyl)-2,5-diazabicyclo[2.2.1]heptane-2-carboxylate:
Dried vial was charged with (1S,4S)-tert-butyl 2,5-diazabicyclo[2.2.1]heptane-2-carboxylate (0.5 g, 2.52 mmol), 1-(benzyloxy)-4-bromobenzene (0.995 g, 3.78 mmol), sodium tert-butoxide (0.727 g, 7.57 mmol), BINAP (0.314 g, 0.504 mmol), Toluene (15 mL) and reaction mixture was degassed with nitrogen for 10 min. Then Pd$_2$(dba)$_3$ (0.231 g, 0.252 mmol) was added, vial was sealed and heated at 100° C. for overnight. The reaction mixture was cooled to room temperature, filtered through Celite pad, washed with excess and filtrate was concentrated under reduced pressure to give crude residue. The crude residue was purified by flash chromatography (20-40% EtOAc in n-hexane) to afford (1S,4S)-tert-butyl 5-(4-(benzyloxy)phenyl)-2,5-diazabicyclo[2.2.1]heptane-2-carboxylate (0.42 g, 1.104 mmol, 43.8% yield). LC/MS [M+H]+=381.4, $t_R$=1.58 min (Method E).

Step-2. Synthesis of (1S,4S)-tert-butyl 5-(4-hydroxyphenyl)-2,5-diazabicyclo [2.2.1]heptane-2-carboxylate: To a degassed solution (1S,4S)-tert-butyl 5-(4-(benzyloxy)phenyl)-2,5-diazabicyclo[2.2.1]heptane-2-carboxylate (0.15 g, 0.394 mmol) in EtOAc (5 mL), was added palladium on carbon (0.126 g, 0.118 mmol), palladium hydroxide on carbon (0.083 g, 0.118 mmol) and stirred the mixture at rt under hydrogen pressure (~1 atm) for 12 h. The reaction mixture was filtered through Celite pad, washed with excess EtOAc/MeOH (1:1, 30 mL) and filtrate was concentrated under reduced pressure to give the crude residue. The crude residue was purified by flash chromatography (50%-70% EtOAc in n-hexane) to (((1S,4S)-tert-butyl 5-(4-hydroxy-

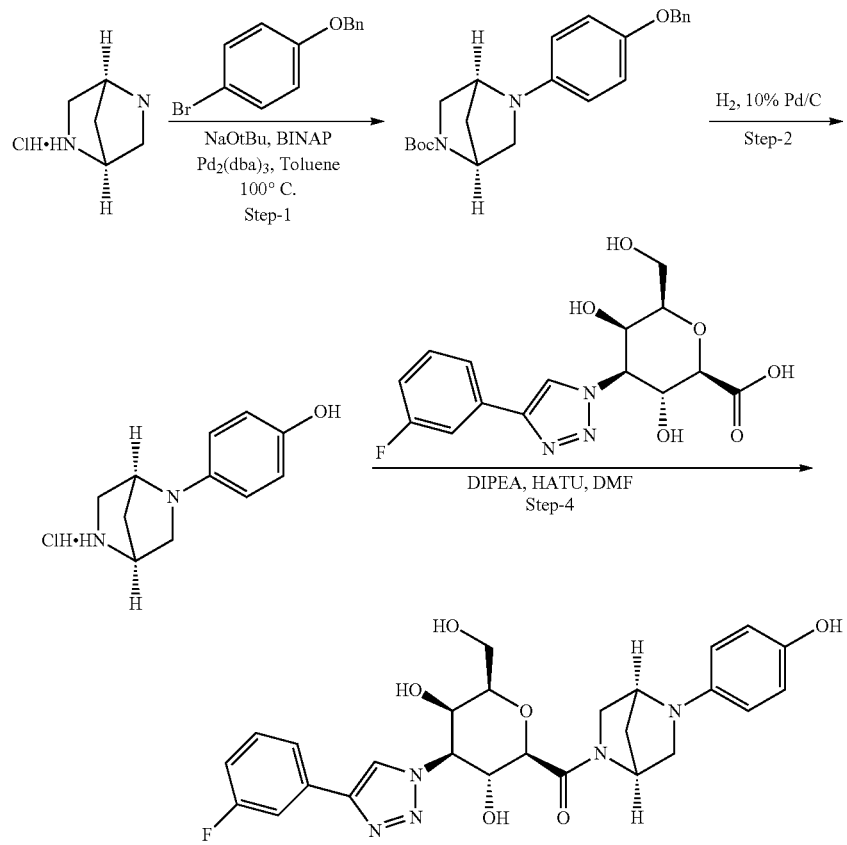

phenyl)-2,5-diazabicyclo[2.2.1]heptane-2-carboxylate (0.06 g, 0.207 mmol, 52.4% yield)) as a pale yellow solid. LC/MS [M+H]$^+$=291.2, $t_R$=2.10 min (Method C).

Step-3. Synthesis of 4-((1S,4S)-2,5-diazabicyclo[2.2.1] heptan-2-yl)phenol hydrochloride: To an ice cooled stirred solution of (1S,4S)-tert-butyl 5-(4-hydroxyphenyl)-2,5-diazabicyclo[2.2.1]heptane-2-carboxylate (0.05 g, 0.172 mmol) in DCM (5 mL), HCl (in dioxane) (0.431 mL, 1.722 mmol) was added. The reaction mixture was allowed to reach room temperature and stirred for 2 h. Solvent was removed under reduced pressure and dried to afford 4-((1S, 4S)-2,5-diazabicyclo[2.2.1]heptan-2-yl)phenol hydrochloride (30 mg, 80% yield). LC/MS [M+H]$^+$=191.1, $t_R$=0.49 min (Method C, ELSD detector).

Step-4. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((1S,4S)-5-(4-hydroxyphenyl)-2,5-diazabicyclo[2.2.1]heptan-2-yl) methanone: To a stirred solution of (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.02 g, 0.057 mmol) in DMF (1.0 mL), 4-((1S,4S)-2,5-diazabicyclo[2.2.1]heptan-2-yl)phenol hydrochloride (0.026 g, 0.113 mmol), DIPEA (0.099 mL, 0.566 mmol) and HATU (0.054 g, 0.142 mmol) were added sequentially at room temperature and stirred overnight. The solvent was removed under reduced pressure and crude residue was purified by prep-HPLC [Method A] to afford Example 25 (3.8 mg, 12%). LC/MS [M+H]$^+$=526.2, $t_R$=0.96 min (Method A). $^1$H NMR (400 MHz, MEOH-d$_4$) δ ppm 8.56-8.40 (m, 1H), 7.74-7.54 (m, 2H), 7.52-7.39 (m, 1H), 7.16-7.00 (m, 1H), 6.79-6.53 (m, 4H), 5.13-4.85 (m, 2H), 4.73-4.45 (m, 2H), 4.36-4.04 (m, 2H), 3.96-3.44 (m, 6H), 3.22-3.07 (m, 1H), 2.29-1.88 (m, 2H). (Mixture of Rotamers). hGal3 IC$_{50}$=0.90 μM.

Example 26: Synthesis of ((1S,4S)-5-(1H-indol-5-yl)-2,5-diazabicyclo[2.2.1]heptan-2-yl)((2R,3R,4S, 5R,6R)-4-(4-(3-fluorophenyl)-1H-1,2,3-triazol-1-yl)-3,5-dihydroxy-6-(hydroxymethyl)tetrahydro-2H-pyran-2-yl)methanone

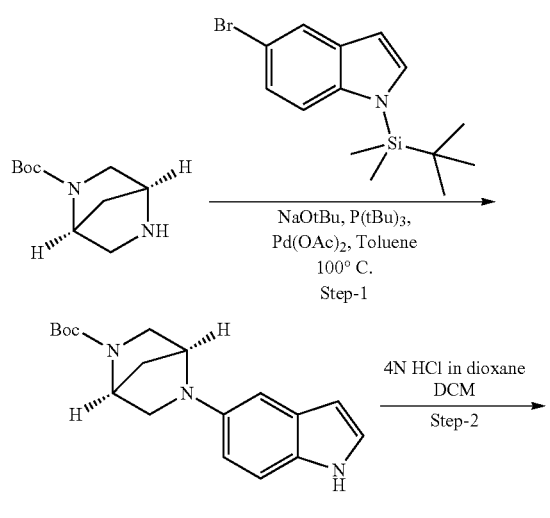

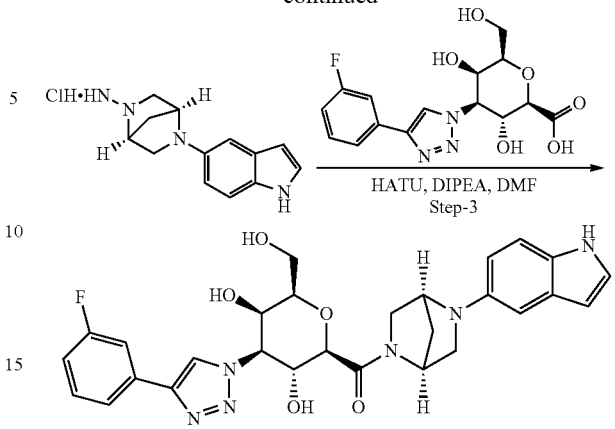

Step-1. Synthesis of (1S,4S)-tert-butyl 5-(1H-indol-5-yl)-2,5-diazabicyclo[2.2.1]heptane-2-carboxylate: To a stirred solution of (1S,4S)-tertbutyl 2,5-diazabicyclo[2.2.1]heptane-2-carboxylate (141 mg, 0.709 mmol) in Toluene (5 mL), was added tri-t-butylphosphine (6.52 mg, 0.032 mmol), sodium tert-butoxide (93 mg, 0.967 mmol) and 5-bromo-1-(tert-butyldimethylsilyl)-1H-indole (200 mg, 0.645 mmol) sequentially. The reaction mixture was degassed with Ar for 10 min and Pd(OAc)$_2$ (7.24 mg, 0.032 mmol) was added and reaction mixture was heated at 110° C. for 14 h. The reaction mixture was cooled to room temperature, filtered through Celite pad, washed with EtOAc (20 mL) and the filtrate was concentrated under reduced pressure to give crude residue. The crude residue was purified by flash chromatography (50-80% EtOAc in pet ether) to afford of (1S,4S)-tert-butyl 5-(1H-indol-5-yl)-2,5-diazabicyclo[2.2.1]heptane-2-carboxylate (50 mg, 0.16 mmol, 25% yield). LC/MS [M+H]$^+$=314.2, (Method E: $t_R$=1.23 min).

Step-2. Synthesis of 4-((1S,4S)-2,5-diazabicyclo[2.2.1] heptan-2-yl)phenol hydrochloride: To an ice cooled stirred solution (1S,4S)-tert-butyl 5-(1H-indol-5-yl)-2,5-diazabicyclo[2.2.1]heptane2-carboxylate (50 mg, 0.160 mmol) in DCM (5 mL), HCl (4M in dioxane) (0.05 mL, 1.595 mmol) was added. The reaction mixture was allowed to reach room temperature and stirred for 2 h. Solvent was removed under reduced pressure and dried to afford 5-((1S,4S)-2,5-diazabicyclo[2.2.1]heptan-2-yl)-1H-indole.HCl (30 mg, 0.141 mmol, 90% yield). LC/MS [M+H]$^+$=214.1, $t_R$=0.57 min (Method D). Step-3: Synthesis of ((1S,4S)-5-(1H-indol-5-yl)-2,5-diazabicyclo[2.2.1]heptan-2-yl)((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl) methanone: To a stirred solution of (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (25 mg, 0.071 mmol) in DMF (1.0 mL), 5-((1S,4S)-2,5-diazabicyclo[2.2.1]heptan-2-yl)-1H-indole (23 mg, 0.106 mmol), DIPEA (0.12 mL, 0.71 mmol) and HATU (0.041 g, 0.106 mmol) were added sequentially at room temperature and stirred for overnight. The solvent was removed under reduced pressure and crude residue was purified by prep-HPLC [Method D] to afford Example 26 (1.9 mg, 3.43 μmol, 5% yield). LC/MS [M+H]$^+$=549.1, $t_R$=1.37 min (Method A). $^1$H NMR (400 MHz, MEOH-d$_4$) δ ppm 8.54-8.42 (m, 1H), 7.70-7.56 (m, 3H), 7.49-7.33 (m, 3H), 7.21-7.07 (m, 2H), 6.91-6.76 (m, 1H), 5.23-4.88 (m, 1H), 4.71-4.53 (m, 2H), 4.36-4.33 (m, 1H), 4.38-4.01 (m, 3H), 3.96-3.66 (m, 4H), 3.60-3.54 (m, 2H), 2.40-2.03 (m, 2H). (Mixture of Rotamers). hGal3 IC$_{50}$=0.30 μM.

Example 27: Synthesis of 2-((2S,3R,4R,5R,6R)-4-(4-(3-fluorophenyl)-1H-1,2,3-triazol-1-yl)-3,5-dihydroxy-6-(hydroxymethyl)tetrahydro-2H-pyran-2-yl)-1-((1S,4S)-5-(4-methoxyphenyl)-2,5-diazabicyclo[2.2.1]heptan-2-yl)ethanone

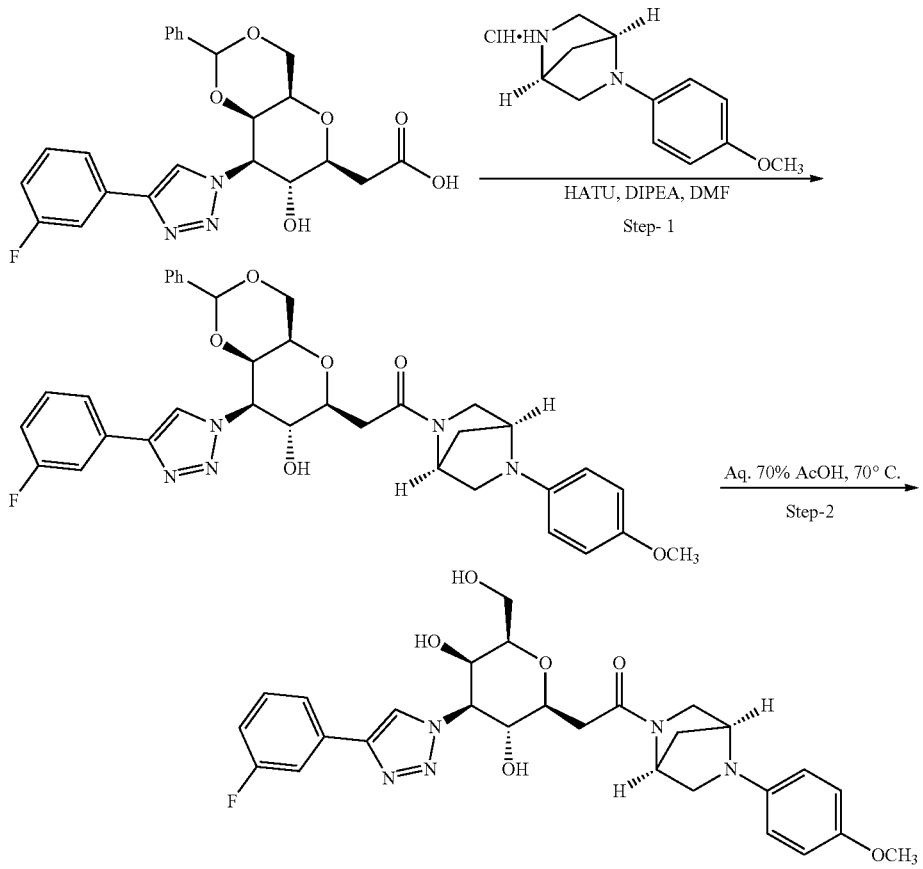

Step-1. Synthesis of 2-((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1-((1S,4S)-5-(4-methoxyphenyl)-2,5-diazabicyclo[2.2.1]heptan-2-yl)ethanone: Prepared in a similar fashion as described in Example 1 using (1S,4S)-2-(4-methoxyphenyl)-2,5-diazabicyclo[2.2.1]heptane hydrochloride (21.2 mg, 0.09 mmol) and 2-((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)acetic acid (20 mg, 0.044 mmol). The solvent was removed under reduced pressure, diluted with ice water (~20 mL) and extracted with EtOAc (3×10 mL). The combined organic extracts were washed with water (20 mL), brine (20 mL), dried over sodium sulphate and concentrated under reduced pressure to give crude residue. The crude residue was purified by flash chromatography (5-10% MeOH in DCM) to afford 2-((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1-((1S,4S)-5-(4-methoxyphenyl)-2,5-diazabicyclo[2.2.1]heptan-2-yl)ethanone as off white solid (30 mg, 59% yield). LC/MS [M+H]+=641.2, (Method C: $t_R$=2.83 min).

Step-2. Synthesis of 2-((2S,3R,4R,5R,6R)-4-(4-(3-fluorophenyl)-1H-1,2,3-triazol-1-yl)-3,5-dihydroxy-6-(hydroxymethyl)tetrahydro-2H-pyran-2-yl)-1-((1S,4S)-5-(4-methoxyphenyl)-2,5-diazabicyclo[2.2.1]heptan-2-yl)ethanone: 2-((4aR,6S,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1-((1S,4S)-5-(4-methoxyphenyl)-2,5-diazabicyclo[2.2.1]heptan-2-yl)ethanone (25 mg, 0.04 mmol) was suspended in acetic acid (70% aqueous solution) (3 mL, 52.4 mmol) and heated at 70° C. overnight. The reaction mixture was cooled to room temperature, solvent was removed under reduced pressure to give crude residue. The crude residue was purified by preparative HPLC [Method B] to afford Example 27 (3.4 mg, 16% yield) as a brown solid. LC/MS [M+H]+= 554.2, $t_R$=1.499 min (Method A). 1H NMR (400 MHz, MEOH-$d_4$) δ ppm 8.47, 8.43 (two s, 1H), 7.71-7.53 (m, 2H), 7.51-7.39 (m, 1H), 7.15-7.02 (m, 1H), 6.83 (d, J=8.8 Hz, 2H), 6.60 (dd, J=9.0, 3.2 Hz, 2H), 4.98-4.67 (m, 2H), 4.57-4.41 (m, 1H), 4.24-4.06 (m, 2H), 3.92-3.49 (m, 9H), 3.47-3.18 (m, 1H), 3.10-2.90 (m, 1H), 2.83-2.66 (m, 1H), 2.57-2.48 (m, 1H), 2.17-1.91 (m, 2H) (Mixture of Rotamers). hGal3 $IC_{50}$=0.35 μM.

Example 28 was prepared in an analogous fashion to Examples 27, substituting (1S,4S)-2-(4-methoxyphenyl)-2,5-diazabicyclo[2.2.1]heptane hydrochloride with the appropriate piperazine fragment in the synthetic sequence.

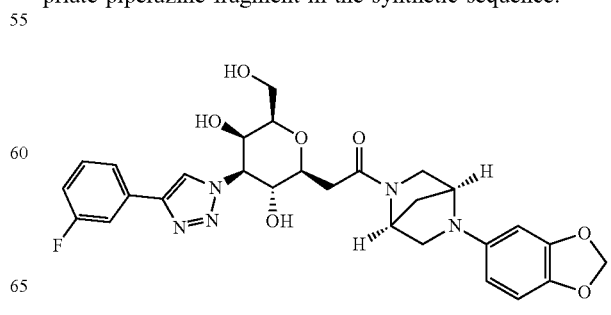

LC/MS [M+H]⁺=568.2, $t_R$=1.49 min (Method A). ¹H NMR (400 MHz, MEOH-$d_4$) δ ppm 8.44 (m, 1H), 7.55-7.71 (m, 2H), 7.40-7.50 (m, 1H), 7.03-7.14 (m, 1H), 6.64-6.72 (m, 1H), 6.27-6.36 (m, 1H), 6.00-6.09 (m, 1H), 5.78-5.85 (m, 2H), 4.69-4.79 (m, 1H), 4.39-4.51 (m, 1H), 4.08-4.24 (m, 2H), 3.76-3.91 (m, 1H), 3.38-3.74 (m, 6H), 2.90-3.25 (m, 1H), 2.48-2.83 (m, 1H), 1.98-2.18 (m, 2H), (2H might be obscured with moisture peak). hGal3 IC₅₀=0.58 μM.

Example 29. Synthesis of (2R,3R,4R,5R,6S)-4-(4-(3-fluorophenyl)-1H-1,2,3-triazol-1-yl)-2-(hydroxymethyl)-6-(((1S,4S)-5-(4-methoxyphenyl)-2,5-diazabicyclo[2.2.1]heptan-2-yl)methyl)tetrahydro-2H-pyran-3,5-diol

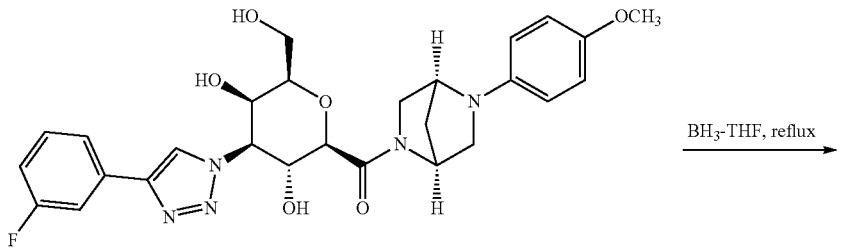

Example 16

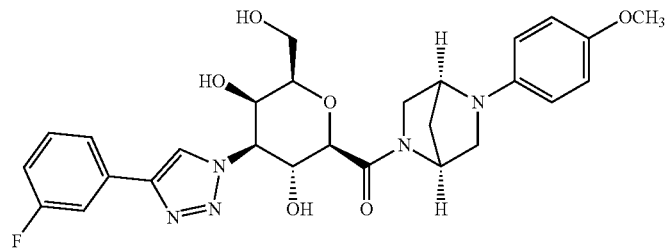

((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((1S,4S)-5-(4-methoxyphenyl)-2,5-diazabicyclo[2.2.1]heptan-2-yl)methanone (30 mg, 0.056 mmol) was suspended in borane tetrahydrofuran complex (5 mL, 0.056 mmol) and refluxed at 70° C. for overnight. The reaction mixture was cooled to 0° C., quenched with MeOH (10 mL) and solvent was removed under reduced pressure to give crude residue. The crude residue was purified by preparative HPLC [Method D] to afford Example 29. LC/MS [M+H]⁺= 526.2, $t_R$=1.430 min (Method A). ¹H NMR (400 MHz, MEOH-$d_4$) δ ppm 8.44 (s, 1H), 7.65 (d, J=8.0 Hz, 1H), 7.62-7.56 (m, 1H), 7.45 (td, J=8.0, 6.0 Hz, 1H), 7.07 (td, J=8.5, 2.0 Hz, 1H), 6.86-6.79 (m, 2H), 6.64-6.57 (m, 2H), 4.79 (dd, J=10.5, 3.0 Hz, 1H), 4.30 (s, 1H), 4.17-4.10 (m, 1H), 4.08 (d, J=3.0 Hz, 1H), 3.94 (br. s., 1H), 3.78-3.74 (m, 2H), 3.72 (s, 3H), 3.69-3.53 (m, 2H), 3.52-3.46 (m, 1H), 3.34 (s, 1H), 3.22-3.12 (m, 2H), 3.06-2.90 (m, 2H), 2.09-2.00 (m, 2H). hGal3 IC₅₀=0.25 μM.

Example 30. Synthesis of (1S, 4S)-5-((2R, 3R, 4S, 5R, 6R)-4-(4-(3-fluorophenyl)-1H-1,2,3-triazol-1-yl)-3,5-dihydroxy-6-(hydroxymethyl)tetrahydro-2H-pyran-2-carbonyl)-N-(4-hydroxyphenyl)-2,5-diazabicyclo[2.2.1]heptane-2-carboxamide

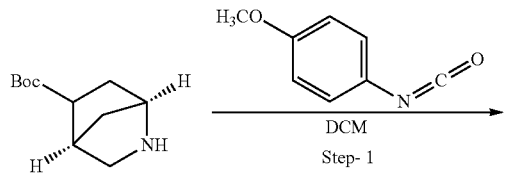

Step-1

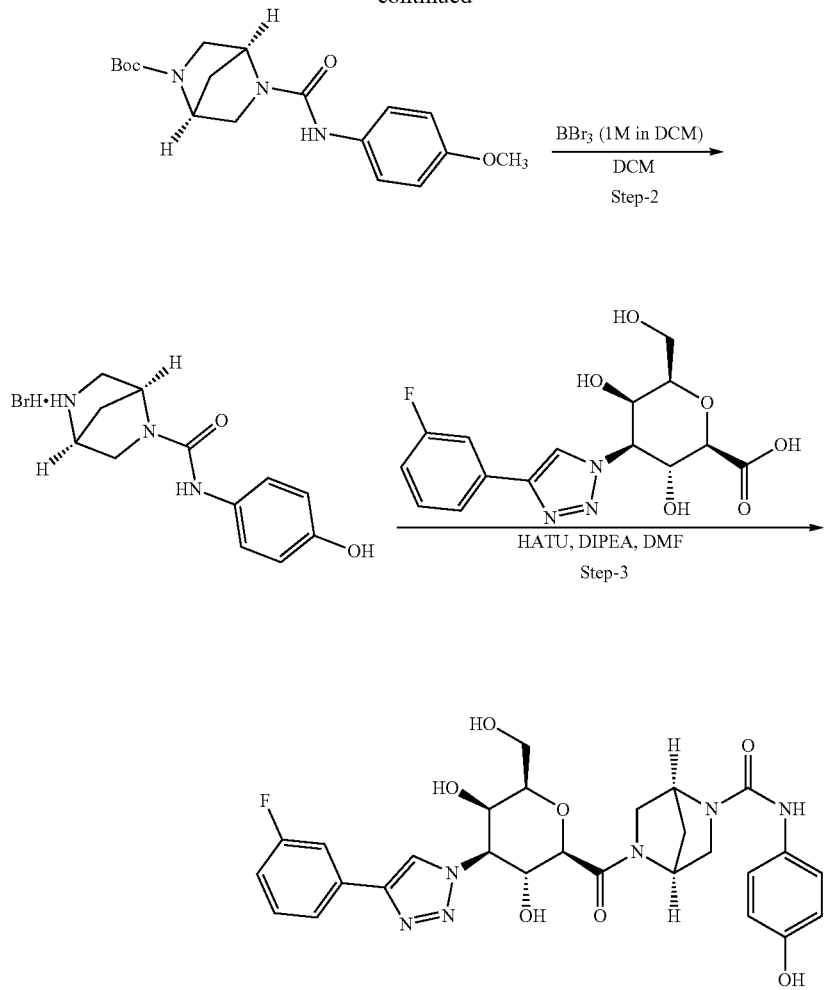

Step-1. Synthesis of (1S, 4S)-tert-butyl 5-((4-methoxyphenyl)carbamoyl)-2,5-diazabicyclo[2.2.1]heptane-2-carboxylate: To a stirred solution of (1S, 4S)-tert-butyl 2,5-diazabicyclo[2.2.1]heptane-2-carboxylate (0.2 g, 1.009 mmol) in DCM (4 mL), 1-isocyanato-4-methoxybenzene (0.133 mL, 1.059 mmol) was added and stirred for 2 h at room temperature. The Reaction mixture was diluted with DCM (20 mL), washed with aq.1N HCl (20 mL), aq/10% NaHCO₃ solution, water, brine, dried over sodium sulphate and solvent was removed under reduced pressure to give crude residue. The crude residue was washed with EtOAc (5 mL), followed by n-hexane (10 mL) and the obtained solid was filtered and dried to afford (1S, 4S)-tert-butyl 5-((4-methoxyphenyl)carbamoyl)-2,5-diazabicyclo[2.2.1]heptane-2-carboxylate (0.2 g, 0.570 mmol, 56.5% yield) as white solid. LC/MS [M+H]$^+$=348.2, (Method F: $t_R$=1.33 min).

Step-2. Synthesis of (1S, 4S)—N-(4-hydroxyphenyl)-2,5-diazabicyclo[2.2.1]heptane-2-carboxamide: The solution of (1S, 4S)-tert-butyl 5-((4-methoxyphenyl)carbamoyl)-2,5-diazabicyclo[2.2.1]heptane-2-carboxylate (0.05 g, 0.144 mmol) in DCM (2 mL) was cooled to –78° C., BBr₃ (1M in DCM) (0.720 mL, 0.720 mmol) was added drop wise under N₂. The reaction mixture was allowed to warm to room temperature and stirred for 16 h. The reaction mixture was cooled to 0° C., quenched with MeOH and the solvent was removed under reduced pressure to give (1S,4S)—N-(4-hydroxyphenyl)-2,5-diazabicyclo[2.2.1]heptane-2-carboxamide. HBr (0.03 g, 0.129 mmol, 89% yield) as a white solid which was as such taken for next step without further purification. LC/MS [M+H]$^+$=234.2, (Method F: $t_R$=1.33 min).

Step-3. Synthesis of (1S,4S)-5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)-N-(4-hydroxyphenyl)-2,5-diazabicyclo[2.2.1]heptane-2-carboxamide: Prepared in a similar fashion as described in Example 1 by using (1S,4S)—N-(4-hydroxyphenyl)-2,5-diazabicyclo[2.2.1]heptane-2-carboxamide, hydrobromide (0.027 g, 0.085 mmol) and (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.02 g, 0.057 mmol). The crude residue was purified by preparative HPLC [Method E] to afford Example 30 (1.7 mg, 2.99 μmol, 5.28% yield) as an off white solid. LC/MS [M+H]$^+$= 569.2, $t_R$=1.06 min (Method A). $^1$H NMR (400 MHz, MEOH-d₄) δ ppm 8.51 (s, 1H), 7.69-7.64 (m, 1H), 7.61 (d, J=9.8 Hz, 1H), 7.49-7.42 (m, 1H), 7.20-7.05 (m, 3H), 6.71 (dd, J=10.5, 8.8 Hz, 2H), 5.17-4.87 (m, 2H), 4.78-4.59 (m, 2H), 4.34-4.11 (m, 2H), 3.96-3.67 (m, 4H), 3.64-3.46 (m, 3H), 2.11-1.96 (m, 2H). (Mixture of rotamers). hGal3 IC$_{50}$=0.50 μM.

Example 31. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((1S,4S)-5-(4-methoxyphenyl)-2,5-diazabicyclo[2.2.1]heptan-2-yl)methanone

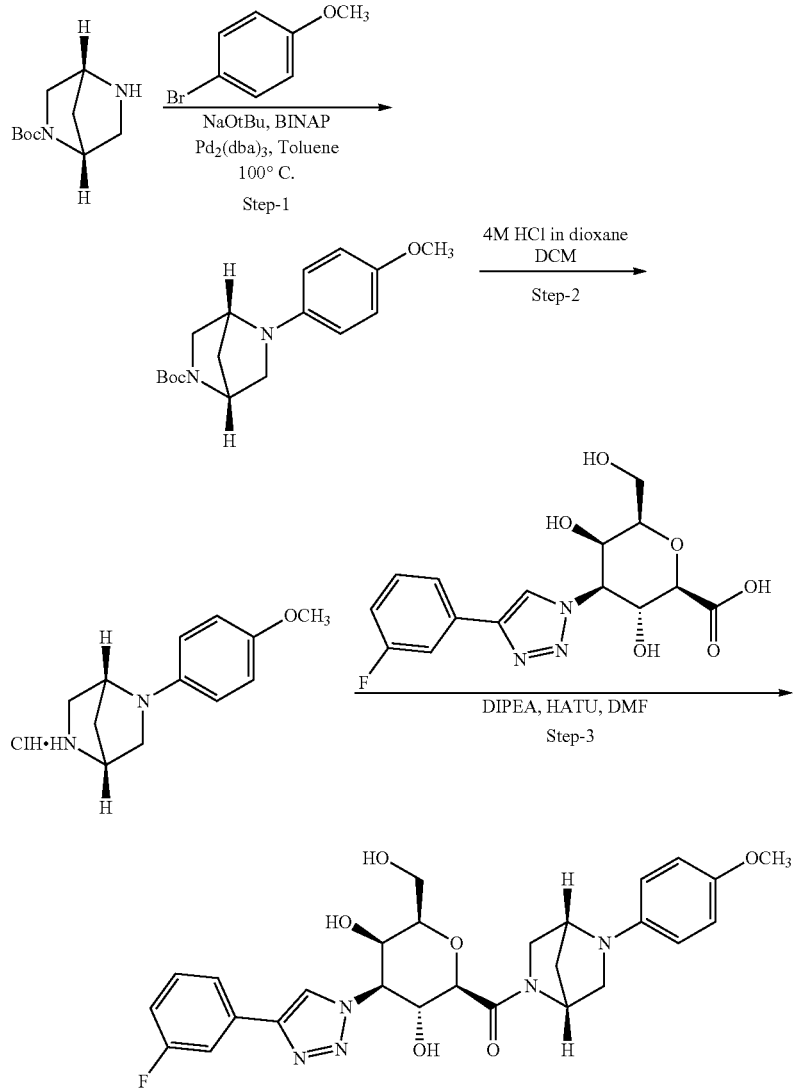

Step-1. Synthesis of (1R,4R)-tert-butyl 5-(4-methoxyphenyl)-2,5-diazabicyclo [2.2.1]heptane-2-carboxylate: Dried vial was charged with (1R,4R)-tert-butyl 2,5-diazabicyclo [2.2.1]heptane-2-carboxylate (0.085 g, 0.428 mmol), 1-bromo-4-methoxybenzene (0.08 g, 0.428 mmol), sodium tertbutoxide (0.06 g, 0.584 mmol), BINAP (0.027 g, 0.043 mmol), toluene (2 mL) and reaction mixture was degassed nitrogen for 10 min. Then $Pd_2(dba)_3$ (0.02 g, 0.021 mmol) was added, vial was sealed and heated at 100° C. for overnight. The reaction mixture was cooled to room temperature, filtered through Celite pad, washed with excess and filtrate was concentrated under reduced pressure to give crude residue. The crude residue was purified by flash chromatography (45-65% EtOAc in n-hexane) to afford (1R,4R)-tert-butyl 5-(4-methoxyphenyl)-2,5-diazabicyclo [2.2.1]heptane-2-carboxylate (0.04 g, 0.093 mmol, 22% yield). LC/MS [M+H]$^+$=305.5, $t_R$=1.40 min (Method E).

Step-2. Synthesis of (1R,4R)-2-(4-methoxyphenyl)-2,5-diazabicyclo[2.2.1]heptane, HCl: To an ice cooled stirred solution of (1R,4R)-tert-butyl 5-(4-methoxyphenyl)-2,5-diazabicyclo[2.2.1]heptane-2-carboxylate (0.04 g, 0.131 mmol) in in DCM (2 mL), 4M HCl in dioxane (0.5 mL, 2.0 mmol) was added. The reaction mixture was allowed to reach room temperature and stirred for 2 h. Solvent was removed under reduced pressure, washed with 10 mL diethylether+1 mL of MeOH and dried to afford (1R,4R)-2-(4-methoxyphenyl)-2,5-diazabicyclo[2.2.1]heptane, HCl (0.03 g, 0.122 mmol, 93% yield) as a brown gummy solid. LC/MS [M+H]$^+$=205.2, $t_R$=0.99 min (Method F).

Step-3. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((1S,4S)-5-(4-methoxyphenyl)-2,5-diazabicyclo[2.2.1]heptan-2-yl) methanone: To a stirred solution of (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.015 g, 0.042 mmol) in DMF (1.0 mL), (1R,4R)-2-(4-methoxyphenyl)-2,5-diazabicyclo[2.2.1]heptane, HCl (0.015 g, 0.064 mmol) DIPEA (0.074 mL, 0.425 mmol) and HATU (0.040 g, 0.106 mmol) were added sequentially at room temperature and stirred for overnight. The solvent was removed under reduced pressure and crude residue was purified by prep-HPLC [Method A] to afford Example 31 (5.5 mg, 9.79 µmol, 23% yield). LC/MS [M+H]$^+$=540.2, $t_R$=1.44 min (Method A). $^1$H NMR (400 MHz, DMSO-d$_6$) δ ppm 8.66-8.60 (m, 1H), 7.78-7.66 (m, 2H), 7.53-7.45 (m, 1H), 7.18-7.11 (m, 1H), 6.84-6.75 (m, 2H), 6.60-6.53 (m, 2H), 5.25-5.01 (m, 2H), 4.88-4.64 (m, 3H), 4.57-4.40 (m, 2H), 4.23 (d, J=9.0 Hz, 1H), 4.08 (q, J=5.4 Hz, 1H), 4.01-3.94 (m, 2H), 3.90 (dd, J=6.0, 3.3 Hz, 1H), 3.83 (t, J=6.2 Hz, 1H), 3.71-3.63 (m, 2H), 3.63-3.45 (m, 1H), 3.41-3.36 (m, 1H), 3.18-3.13 (m, 1H), 2.93 (d, J=8.6 Hz, 1H), 2.06-1.83 (m, 2H) (Rotameric mixture). hGal$_3$ IC$_{50}$=0.22 µM.

Example 32 was prepared in an analogous fashion to Examples 27, substituting 1-bromo-4-methoxybenzene with the appropriate aryl bromide in the synthetic sequence.

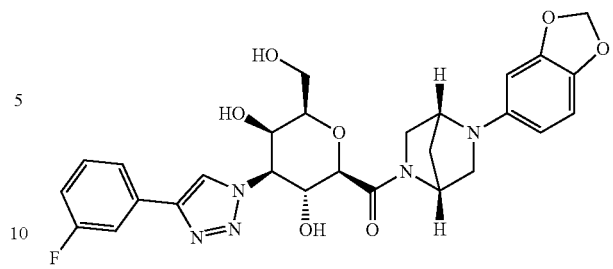

LC/MS [M+H]$^+$=554.2, $t_R$=1.48 min (Method A). $^1$H NMR (400 MHz, MEOH-d$_4$) δ ppm 8.54-8.43 (m, 1H), 7.70-7.55 (m, 2H), 7.49-7.40 (m, 1H), 7.08 (d, J=7.3 Hz, 1H), 6.71-6.61 (m, 1H), 6.35-6.25 (m, 1H), 6.10-5.99 (m, 1H), 5.85-5.75 (m, 2H), 5.01-4.90 (m, 2H), 4.66-4.43 (m, 3H), 4.35 (d, J=9.3 Hz, 1H), 4.16-4.06 (m, 1H), 3.96-3.89 (m, 1H), 3.85-3.47 (m, 3H), 3.23 (d, J=9.3 Hz, 1H), 3.08 (d, J=8.3 Hz, 1H), 2.14-1.93 (m, 2H). hGal3 IC$_{50}$=0.18 µM.

Example 33. Synthesis of ((2R, 3R, 4S, 5R, 6R)-4-(4-(3-fluorophenyl)-1H-1,2,3-triazol-1-yl)-3,5-dihydroxy-6-(hydroxymethyl)tetrahydro-2H-pyran-2-yl)(4-(4-hydroxyphenyl)-1,4-diazepan-1-yl)methanone

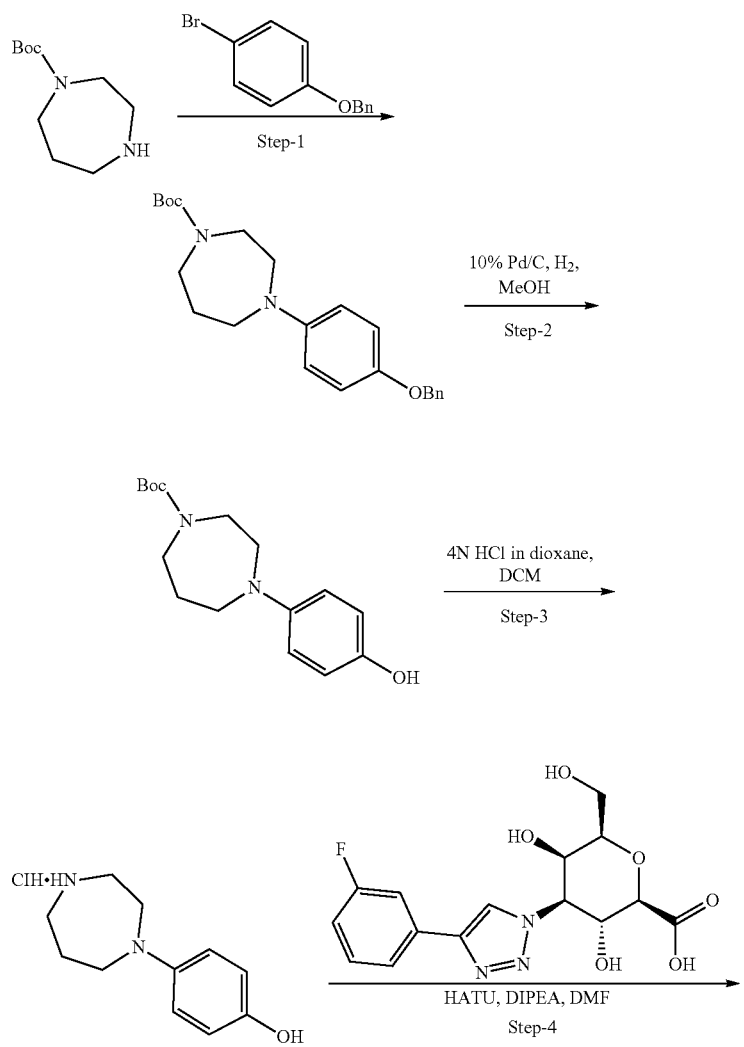

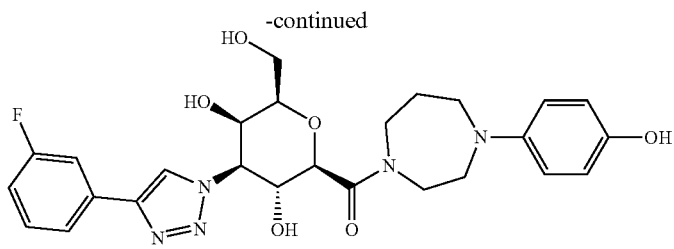

Step-1. Synthesis of tert-butyl 4-(4-(benzyloxy) phenyl)-1,4-diazepane-1-carboxylate: To a stirred solution of 1-(benzyloxy)-4-bromobenzene (0.2 g, 0.760 mmol) in Toluene (5 mL), was added BINAP (0.095 g, 0.152 mmol), sodium tert-butoxide (0.219 g, 2.280 mmol) and tert-butyl 1,4-diazepane-1-carboxylate (0.228 g, 1.140 mmol) sequentially. The reaction mixture was degassed with Ar for 10 min and Pd$_2$(dba)$_3$ (0.070 g, 0.076 mmol) was added and reaction mixture was heated at 80° C. for 14 h. The reaction mixture was cooled to room temperature, filtered through Celite pad, washed with EtOAc and the filtrate was concentrated under reduced pressure to give crude residue. The crude residue was purified by flash chromatography (0-30% EtOAc in pet ether) to afford tert-butyl 4-(4-(benzyloxy) phenyl)-1,4-diazepane-1-carboxylate (0.2 g, 0.523 mmol, 68.8% yield). LC/MS [M+H]$^+$=383.2, (Method C).

Step-2. Synthesis of tert-butyl 4-(4-hydroxyphenyl)-1,4-diazepane-1-carboxylate: To a stirred solution of tert-butyl 4-(4-(benzyloxy) phenyl)-1,4-diazepane-1-carboxylate (0.2 g, 0.523 mmol) in MeOH (4 mL) and EtOAc (1 mL), was added 10% Pd/C (0.11 g, 0.105 mmol) under Nitrogen. The reaction mixture was stirred under H$_2$ atmosphere at ambient temperature for 12 h. The reaction mixture was filtered through Celite pad, washed with excess MeOH (20 mL) and filtrate was concentrated under reduced pressure to afford tert-butyl 4-(4-hydroxyphenyl)-1,4-diazepane-1-carboxylate (120 mg, 0.410 mmol, 78% yield). LC/MS [M+H]$^+$=293.2, (Method C).

Step-3. Synthesis of 4-(1,4-diazepan-1-yl)phenol: To a stirred solution of tert-butyl 4-(4-hydroxyphenyl)-1,4-diazepane-1-carboxylate (120 mg, 0.410 mmol) in DCM (2 mL) was added 4N HCl in dioxane (0.513 mL, 2.052 mmol) at 0° C. for 2 h. The reaction mixture was allowed to warm to room temperature and stirred for 2 h. The solvent was removed under reduced pressure, triturated with n-pentane to afford 4-(1,4-diazepan-1-yl)phenol.HCl (65 mg, 0.338 mmol, 82% yield). LC/MS [M+H]$^+$=193.2, (Method C).

Step-4. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)(4-(4-hydroxyphenyl)-1,4-diazepan-1-yl)methanone: Prepared in a similar fashion as described in Example 1 by using 4-(1,4-diazepan-1-yl)phenol.HCl (22 mg, 0.113 mmol) and (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (20 mg, 0.057 mmol). The crude residue was purified by preparative HPLC [Method A] to afford Example 33 (0.5 mg, 0.900 μmol, 1.6% yield). LC/MS [M+H]$^+$=528.1, (Method B). $^1$H NMR (400 MHz, MEOH-d$_4$) δ ppm 8.51 (s, 1H), 7.68-7.66 (d, J=9.4 Hz, 1H), 7.62-7.60 (m, 1H), 7.48-7.43 (m, 1H), 7.10-7.06 (m, 1H), 6.78 (m, 2H), 6.75 (m 1H), 6.31 (m, 1H), 4.88 (d, J=9.0 Hz, 1H), 4.39 (br. s., 1H), 4.13 (br. s., 1H), 3.92 (d, J=6.6 Hz, 3H), 3.74 (dd, J=11.7, 6.4 Hz, 4H), 3.62-3.51 (m, 3H), 2.03 (m 2H) 0.1.37-1.31 (m 2H). (Mixture of rotamers). hGal3 IC50=0.48 μM.

Example 34a and Example 34b. (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid

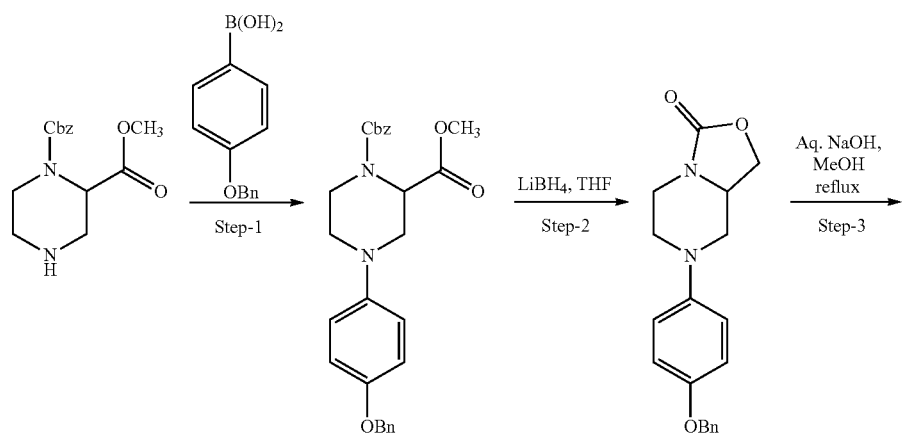

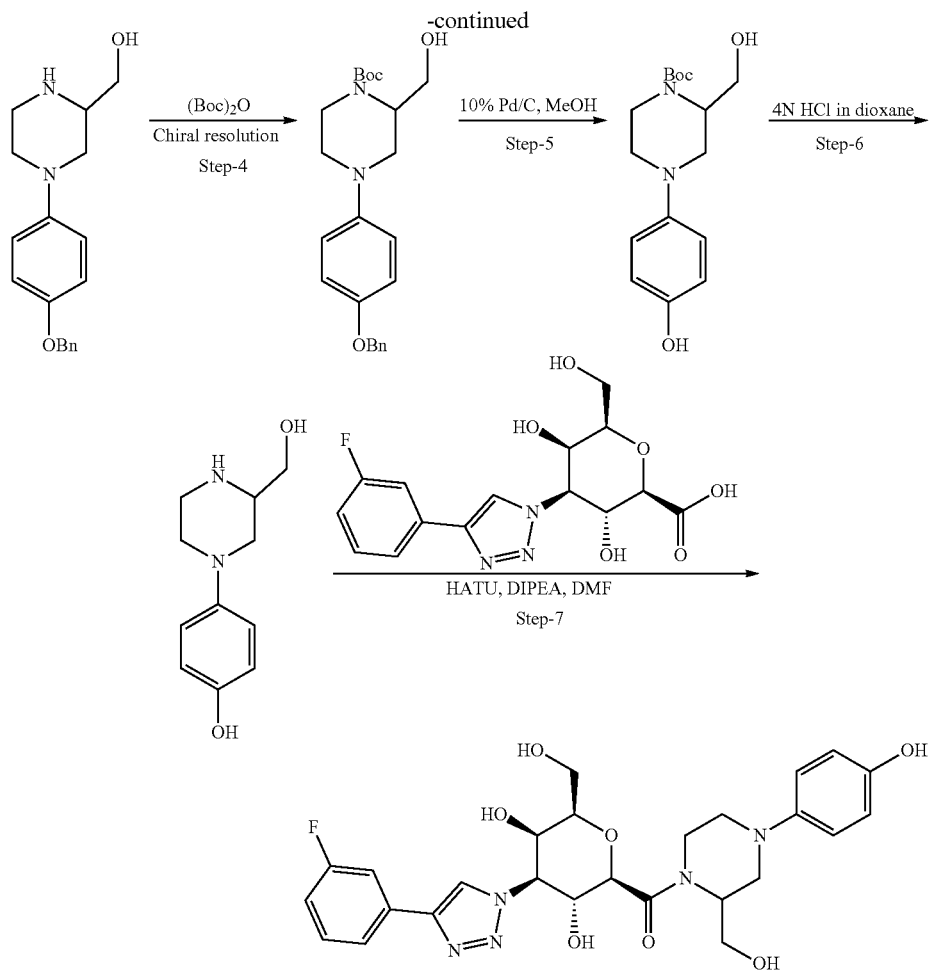

Step-1. Synthesis of 1-benzyl 2-methyl 4-(4-(benzyloxy) phenyl)piperazine-1,2-dicarboxylate: A mixture of 1-benzyl 2-methyl piperazine-1,2-dicarboxylate (2 g, 7.19 mmol), (4-(benzyloxy)phenyl)boronic acid (3.3 g, 14.37 mmol) and copper (II) acetate (1.30 g, 7.19 mmol) in dichloromethane (60 mL) was added pyridine (1.2 mL, 14.37 mmol) and 2 g of 4 Å molecular sieves. The reaction mixture was stirred at room temperature for 48 h under oxygen atmosphere. The resulting suspension was filtered through Celite pad, washed with 50 mL of dichloromethane and filtrate was evaporated under reduced pressure to give the crude residue. The crude residue was purified by flash chromatography (0-10% EtOAc in pet ether) to afford 1-benzyl 2-methyl 4-(4-(benzyloxy)phenyl)piperazine-1,2-dicarboxylate (2.2 g, 8.90 mmol, 40% yield) as off-white solid. LC-MS, [M+H]$^+$= 461.1, (Method F, $t_R$=3.37 min). $^1$H NMR (300 MHz, CDCl$_3$): δ ppm 7.48-7.29 (m, 10H), 6.97-6.84 (m, 4H), 5.27-5.16 (m, 2H), 5.07-5.00 (m, 2H), 4.96-4.77 (m, 1H), 4.16-3.93 (m, 2H), 3.77 (s, 3H), 3.51-3.23 (m, 2H), 2.93-2.65 (m, 2H). (Mixture of rotamers).

Step-2. Synthesis of 7-(4-(benzyloxy)phenyl)tetrahydro-1H-oxazolo[3,4-a]pyrazin-3(5H)-one: To a stirred solution of 1-benzyl 2-methyl 4-(4-(benzyloxy) phenyl)piperazine-1,2-dicarboxylate (500 mg, 1.086 mmol) in THF (10 mL), was added lithium borohydride (2M in THF) (1.6 mL, 3.26 mmol) drop wise at 0° C. under Nitrogen.

Reaction mixture was allowed to warm to rt and stirred for 16 h. Reaction mixture was cooled to 0° C., quenched with sat. aq. NH$_4$Cl solution (15 mL) drop wise and extracted with EtOAc (3×20 mL). The combined organic extracts were washed with water (30 mL), brine solution (2×10 mL), dried over Na$_2$SO$_4$ and solvent was removed under reduced pressure to give crude product which was purified by flash chromatography (25% EtOAc:Hexane) to afford 7-(4-(benzyloxy)phenyl)tetrahydro-1H-oxazolo[3,4-a]pyrazin-3 (5H)-one (0.25 g, 1.086 mmol, 72% yield). LC-MS, [M+H]$^+$=325.2, (Method E, $t_R$=1.23 min). $^1$H NMR (300 MHz, CDCl$_3$): δ ppm 7.47-7.29 (m, 5H), 6.98-6.84 (m, 4H), 5.04 (s, 2H), 4.54-4.40 (m, 1H), 4.09-3.86 (m, 3H), 3.51-3.18 (m, 3H), 2.80-2.55 (m, 2H).

Step-3. Synthesis of (4-(4-(benzyloxy)phenyl)piperazin-2-yl)MeOH: To a stirred solution of 7-(4-(benzyloxy)phenyl)tetrahydro-1H-oxazolo[3,4-a]pyrazin-3(5H)-one (0.8 g, 2.466 mmol) in EtOH (16 mL) was added NaOH (0.691 g, 17.26 mmol) in water (8 mL) and heated at 70° C. for 16 h. The reaction mixture was cooled to room temperature, solvent was removed under reduced pressure to give crude residue which was suspended in 10 mL of water and stirred for 10 min at rt. The obtained solid was filtered and dried to afford (4-(4-(benzyloxy)phenyl)piperazin-2-yl)MeOH (0.66 g, 2.466 mmol, 82% yield) as an off-white solid. LC-MS, [M+H]$^+$=299.2, (Method E, $t_R$=0.95 min).

Step-4. Synthesis of tert-butyl 4-(4-(benzyloxy)phenyl)-2-(hydroxymethyl) piperazine-1-carboxylate: To an ice cooled stirred solution of (4-(4-(benzyloxy)phenyl) piperazin-2-yl)MeOH (0.2 g, 0.670 mmol) in DCM (5 mL) was added di-tert-butyl dicarbonate (0.17 mL, 0.737 mmol) in DCM (2 mL). The reaction mixture was allowed to warm to room temperature and stirred for overnight. Solvent was removed under reduced pressure to give crude residue which was triturated with pet.ether (10 mL) to afford tert-butyl 4-(4-(benzyloxy)phenyl)-2-(hydroxymethyl)piperazine-1-carboxylate (220 mg, 0.552 mmol, 82% yield) as an off-white solid. LC-MS, [M+H]$^+$=399.2, (Method E, $t_R$=1.44 min). The separation of the two enantiomers was accomplished using the following conditions:
Prep SFC Method Info:
Column/dimensions: Lux Amylose-2 (250×21) mm, 5u
% $CO_2$: 65%
% Co solvent: 35% of 0.2% DEA in MeOH
Total Flow: 70.0 g/min
Back Pressure: 100 bar
Temperature: 30° C.
UV: 244 nm
Analytical Chiral SFC Conditions:
Analytical Column: Lux Amylose-2 (250×4.6) mm; 5u
BPR pressure: 100 bars
Temperature: 30° C.
Flow rate: 3 g/min
Mobile Phase: 0.2% DEA in MeOH
Detector Wavelength: UV 200-400 nm
Enantiomer 1: (80 mg, 0.201 mmol, 30% yield); chiral SFC $t_R$=3.07 min; LC-MS, [M+H]$^+$=399.2, (Method C: $t_R$=3.095 min);
Enantiomer 2: (80 mg, 0.201 mmol, 30% yield); chiral SFC $t_R$=5.1 min; LC-MS, [M+H]$^+$=399.2, (Method F: $t_R$=3.09 min).

Step-5. Synthesis of tert-butyl 2-(hydroxymethyl)-4-(4-hydroxyphenyl)piperazine-1-carboxylate: To a solution of tert-butyl 4-(4-(benzyloxy)phenyl)-2-(hydroxymethyl) piperazine-1-carboxylate (80 mg, 0.201 mmol, enantiomer-1) in MeOH (2 mL) was added Pd/C (10% on carbon (10.68 mg, 0.100 mmol) and stirred under $H_2$ atm (1 atm pressure) by using hydrogen bladder for 3 h. Reaction mixture was filtered through Celite pad, washed with excess MeOH (10 mL) and filtrate was evaporated under reduced pressure to afford tert-butyl 2-(hydroxymethyl)-4-(4-hydroxyphenyl) piperazine-1-carboxylate (55 mg, 0.201 mm, 89%) as a brown gummy liquid. LC-MS, [M+H]$^+$=309.2, (Method E: $t_R$=0.93 min).

Step-6. Synthesis of 4-(3-(hydroxymethyl)piperazin-1-yl) phenol: To a stirred solution of tert-butyl 2-(hydroxymethyl)-4-(4-hydroxyphenyl)piperazine-1-carboxylate (50 mg, 0.162 mmol, isomer-1) in DCM (1 mL), was added HCl (4M in dioxane) (0.05 mL, 1.621 mmol) and stirred at RT for 4 h. Solvent was removed under reduced pressure, basified with aq $NaHCO_3$ (10%) and extracted with EtOAc (3×20 mL). The combined organic extracts were dried over $Na_2SO_4$ and solvent was removed under reduced pressure to afford 4-(3-(hydroxymethyl)piperazin-1-yl)phenol (13 mg, 0.062 mmol, 38% yield) as a off-white solid which was as such taken for next step without further purification. LC-MS, [M+H]$^+$=209.2, (Method C: $t_R$=0.38 min).

Step-7. Synthesis of (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid: Prepared in a similar fashion as described in Example 1 using (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (25 mg, 0.071 mmol) and 4-(3-(hydroxymethyl)piperazin-1-yl)phenol (17 mg, 0.085 mmol) to get crude product which was purified by prep-HPLC [Method A] to afford Example 34a ((2R,3R,4S,5R, 6R)-4-(4-(3-fluorophenyl)-1H-1,2,3-triazol-1-yl)-3,5-dihydroxy-6-(hydroxymethyl)tetrahydro-2H-pyran-2-yl)(2-(hydroxymethyl)-4-(4-hydroxyphenyl)piperazin-1-yl) methanone, isomer-1 (1.5 mg, 4% yield). LC-MS, [M+H]$^+$= 544.1, (Method A: $t_R$=1.15). $^1$H NMR (400 MHz, MEOH-$d_4$) δ ppm 8.56-8.51 (m, 1H), 7.73-7.58 (m, 2H), 7.51-7.43 (m, 1H), 7.09 (t, J=8.2 Hz, 1H), 6.93-6.85 (m, 2H), 6.77-6.65 (m, 2H), 4.98-4.91 (m, 1H), 4.79-4.66 (m, 2H), 4.57-4.47 (m, 1H), 4.38-4.27 (m, 1H), 4.21-4.12 (m, 1H), 4.08-3.69 (m, 4H), 3.65-3.36 (m, 3H), 3.16-3.05 (m, 1H), 2.85-2.60 (m, 2H) (Rotameric Mixture); hGal3 $IC_{50}$=1.3 µM.

Example 34b: Prepared in a similar fashion as described for Example 34a, by using enantiomer 2 in Step-4 as the starting material. LC-MS, [M+H]+=544.1, (Method A: $t_R$=1.14 min). $^1$H NMR (400 MHz, DMSO-$d_6$) δ ppm 8.87 (d, J=7.6 Hz, 1H), 8.67 (s, 1H), 7.79-7.66 (m, 2H), 7.54-7.45 (m, 1H), 7.15 (t, J=8.6 Hz, 1H), 6.82 (d, J=8.8 Hz, 2H), 6.72-6.62 (m, 2H), 5.29-5.17 (m, 1H), 4.98-4.78 (m, 3H), 4.72-4.49 (m, 2H), 4.42-4.18 (m, 2H), 4.16-3.93 (m, 3H), 3.85-3.59 (m, 4H), 3.37-3.20 (m, 1H), 3.03-2.90 (m, 1H). hGal3 $IC_{50}$=0.45 µM.

Example 35a and Example 35b. ((2R,3R,4S,5R, 6R)-4-(4-(3-fluorophenyl)-1H-1,2,3-triazol-1-yl)-3, 5-dihydroxy-6-(hydroxymethyl)tetrahydro-2H-pyran-2-yl)(3-(hydroxymethyl)-4-(4-hydroxyphenyl) piperazin-1-yl)methanone

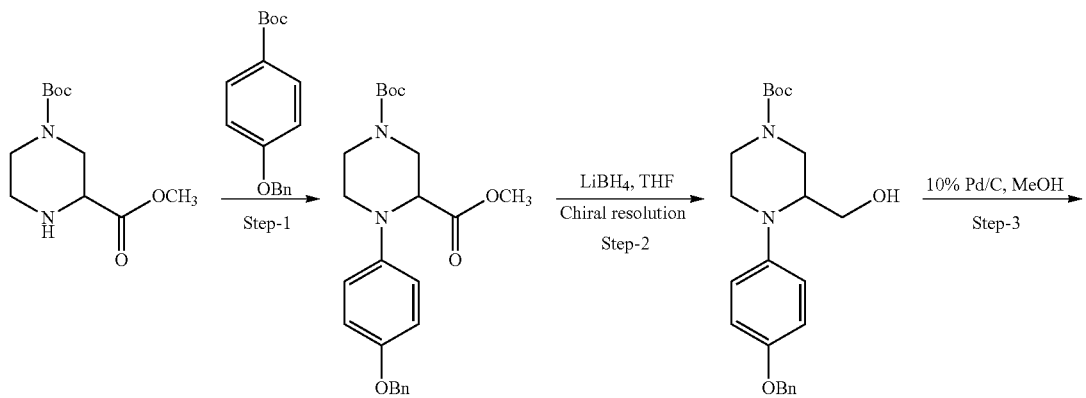

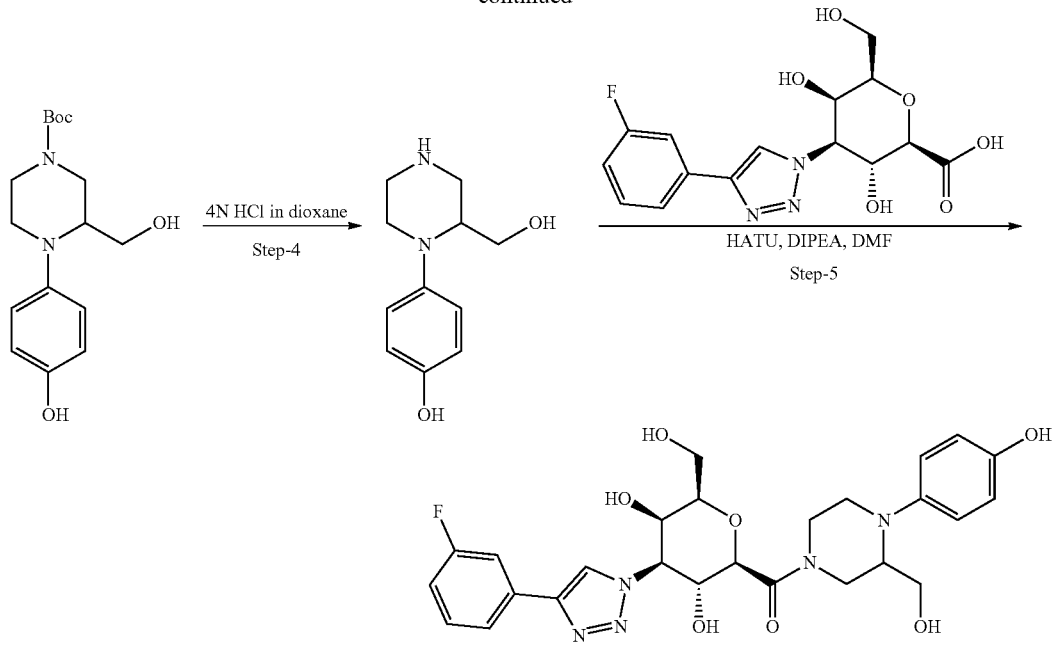

Step-1. Synthesis of 1-tert-butyl 3-methyl 4-(4-(benzyloxy)phenyl)piperazine-1,3-dicarboxylate: A mixture of 1-tert-butyl 3-methyl piperazine-1,3-dicarboxylate (2 g, 8.19 mmol), (4-(benzyloxy)phenyl)boronic acid (3.73 g, 16.37 mmol) and copper (II) acetate (1.5 g, 8.19 mmol) in DCM (60 mL) was added pyridine (1.3 mL, 16.37 mmol) and 2 g of 4 A molecular sieves. The reaction mixture was stirred at rt for 48 h under oxygen atmosphere. The resulting suspension was filtered through Celite pad, washed with DCM (50 mL) and the filtrate was evaporated under reduced pressure to give the crude residue. The crude residue was purified by flash chromatography (0-10% EtOAc in petroleum ether) to afford 1-tert-butyl 3-methyl 4-(4-(benzyloxy)phenyl)piperazine-1,3-dicarboxylate (700 mg, 1.641 mmol, 20% yield). LC-MS, [M+H]$^+$=427.2, (Method C, $t_R$=3.41 min).

Step-2. Synthesis of tert-butyl 4-(4-(benzyloxy)phenyl)-3-(hydroxymethyl) piperazine-1-carboxylate: To a stirred solution of (1-tert-butyl 3-methyl 4-(4-(benzyloxy) phenyl) piperazine-1,3-dicarboxylate (600 mg, 1.41 mmol) in THF (12 mL), was added Li BH$_4$ (2M in THF) (2.1 ml, 4.22 mmol) drop wise at 0° C. under N$_2$. Reaction mixture was allowed to warm to rt and stirred for 16 h. Reaction mixture was cooled to 0° C., quenched with sat. aq. NH$_4$Cl solution (15 mL) drop wise and extracted with EtOAc (3×20 mL). The combined organic extracts were washed with water (30 mL), brine solution (2×10 mL), dried over Na$_2$SO$_4$ and solvent was removed under reduced pressure to give crude product which was purified by flash chromatography (30% EtOAc:Hexane) to afford tert-butyl 4-(4-(benzyloxy)phenyl)-3-(hydroxymethyl)piperazine-1-carboxylate (380 mg, 0.954 mmol, 58% yield)) as racemate. LC-MS, [M+H]$^+$= 399.2, (Method C, $t_R$=3.12 min). The separation of the two enantiomers was accomplished using the following conditions:
Prep SFC Method Info:
Column/dimensions: Lux cellulose-2 (250×21) mm, 5u
% CO$_2$: 60%
% Co solvent: 40% of 0.2% DEA in MeOH
Total Flow: 70.0 g/min
Back Pressure: 100 bar
Temperature: 30° C.
UV: 244 nm
Analytical Chiral SFC Conditions:
Analytical Column: Lux cellulose-2 (250×4.6) mm; 5u
BPR pressure: 100 bars
Temperature: 30° C.
Flow rate: 3 g/min
Mobile Phase: 0.2% DEA in MeOH
Detector Wavelength: UV 200-400 nm
Enantiomer 1: (120 mg, 0.301 mmol, 21% yield); chiral SFC $t_R$=2.87 min; LC-MS, [M+H]$^+$=399.2, (Method G: $t_R$=2.89 min);
Enantiomer 2: (120 mg, 0.301 mmol, 21% yield); chiral SFC $t_R$=4.62 min; LC-MS, [M+H]$^+$=399.2, (Method G: $t_R$=2.89 min);

Step-3. Synthesis of tert-butyl 3-(hydroxymethyl)-4-(4-hydroxyphenyl)piperazine-1-carboxylate: To a solution of tert-butyl 4-(4-(benzyloxy)phenyl)-3-(hydroxymethyl) piperazine-1-carboxylate (80 mg, 0.201 mmol, enantiomer-1) in MeOH (2 mL) was added Pd/C (10% on carbon (11 mg, 0.100 mmol) and stirred under H$_2$ atm (1 atm pressure) by using hydrogen bladder for 3 h. Reaction mixture was filtered through Celite pad, washed with excess MeOH (10 mL) and filtrate was evaporated under reduced pressure to afford tert-butyl 3-(hydroxymethyl)-4-(4-hydroxyphenyl) piperazine-1-carboxylate (55 mg, 0.134 mmol, 67% yield). LC-MS, [M+H]$^+$=309.2, (Method E: $t_R$=0.91 min).

Step-4. Synthesis of 4-(2-(hydroxymethyl)piperazin-1-yl) phenol: To a stirred solution of tert-butyl 3-(hydroxymethyl)-4-(4-hydroxyphenyl)piperazine-1-carboxylate (20 mg, 0.065 mmol) in DCM (1 mL), was added HCl (4M in dioxane) (0.02 mL, 0.65 mmol) and stirred at RT for 4 h. Solvent was removed under reduced pressure, basified with aq NaHCO$_3$ (10%) and extracted with EtOAc (3×20 mL). The combined organic extracts were dried over Na$_2$SO$_4$ and solvent was removed under reduced pressure to afford 4-(2-(hydroxymethyl)piperazin-1-yl)phenol (13 mg, 0.062 mmol, 96% yield) as an off-white solid which was as such taken for next step without further purification. LC-MS, [M+H]+=209.2, (Method C: $t_R$=0.36 min).

Step-5. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)(3-(hydroxyethyl)-4-(4-hydroxyphenyl)piperazin-1-yl)methanone:
Prepared in a similar fashion as described in Example 1 using ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (25 mg, 0.071 mmol) and 4-(2-(hydroxymethyl)piperazin-1-yl)phenol (22 mg, 0.106 mmol) to get crude product which was purified by prep-HPLC [Method A] to afford Example 35a ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)(3-(hydroxymethyl)-4-(4-hydroxyphenyl) piperazin-1-yl) methanone, isomer-1 (21 mg, 0.039 mmol, 55% yield). LC-MS, [M+H]+=544.1, {Method A: $t_R$=1.12}. 1H NMR (400 MHz, MEOH-d4) δ ppm 8.54 (d, J=4.6 Hz, 1H), 7.68 (d, J=7.8 Hz, 1H), 7.62 (d, J=9.8 Hz, 1H), 7.50-7.41 (m, 1H), 7.08 (t, J=8.4 Hz, 1H), 6.96 (d, J=8.8 Hz, 2H), 6.74 (dd, J=8.9, 2.6 Hz, 2H), 5.00-4.92 (m, 1H), 4.81-4.68 (m, 1H), 4.60 (br. s., 1H), 4.41 (t, J=8.2 Hz, 1H), 4.15 (br. s., 1H), 4.03-3.69 (m, 6H), 3.50-3.37 (m, 3H), 3.11 (br. s., 1H), 3.06-2.99 (m, 1H) (Rotameric Mixture); hGal3 IC50=1.1 μM.

Example 35b: Prepared in a similar fashion as described for Example 35a, by using tert-butyl 4-(4-(benzyloxy)phenyl)-3-(hydroxymethyl)piperazine-1-carboxylate, enantiomer 2 as the starting material in Step 3. LC-MS, [M+H]+= 544.1, (Method A: $t_R$=1.12 min). 1H NMR (400 MHz, DMSO-d6) δ ppm 8.94-8.82 (m, 1H), 8.72-8.63 (m, 1H), 7.80-7.67 (m, 2H), 7.54-7.44 (m, 1H), 7.23-7.05 (m, 1H), 6.88-6.77 (m, 2H), 6.90-6.67 (m, 2H), 5.29-5.20 (m, 2H), 5.08-4.82 (m, 2H), 4.72-4.44 (m, 2H), 4.34-4.21 (m, 1H), 4.15-4.11 (m, 1H), 4.10-3.95 (m, 1H), 3.83-3.72 (m, 2H), 3.67-3.47 (m, 5H), 3.24-3.06 (m, 3H), 3.05-2.89 (m, 1H). hGal3 IC50=0.14 μM.

Example 36. ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)(4-(4-hydroxyphenyl)-2-methylpiperazin-1-yl)methanone
(Dia 1)

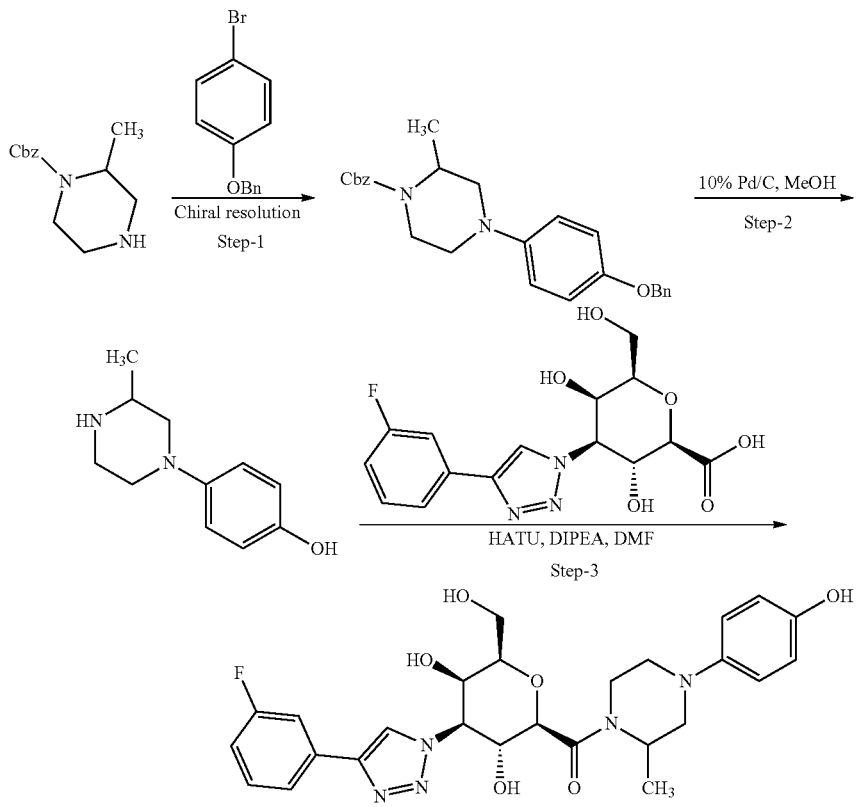

Step-1. Synthesis of benzyl 4-(4-(benzyloxy)phenyl)-2-methylpiperazine-1-carboxylate: Dried vial was charged with benzyl 2-methylpiperazine-1-carboxylate (0.7 g, 2.99 mmol), 1-(benzyloxy)-4-bromobenzene (0.94 g, 3.59 mmol), cesium carbonate (1.36 g, 4.18 mmol), tri-tert-butylphosphonium tetrafluoroborate (0.10 g, 0.36 mmol), toluene (11 mL) and reaction mixture was degassed with nitrogen for 10 min. Then Pd(OAc)2 (0.07 g, 0.299 mmol) was added, vial was sealed and heated at 100° C. overnight. The reaction mixture was cooled to rt, filtered through Celite pad, washed with excess and filtrate was concentrated under reduced pressure to give crude residue. The crude residue was purified by flash chromatography (20-40% EtOAc in n-hexane) to afford benzyl 4-(4-(benzyloxy)phenyl)-2-methylpiperazine-1-carboxylate (1 g, 80%) as racemate. LC/MS [M+H]+=417.4, $t_R$=1.72 min (Method E). 1H NMR (300 MHz, CDCl3): δ ppm 7.46-7.30 (m, 10H), 6.95-6.84 (m, 4H), 5.17 (s, 2H), 5.03 (s, 2H), 4.43 (br. s., 1H), 4.04 (d, J=13.2 Hz, 1H), 3.40-3.27 (m, 2H), 3.23 (d, J=11.7 Hz, 1H), 2.85 (dd, J=11.7, 3.8 Hz, 1H), 2.73-2.61 (m, 1H), 1.36 (d, J=6.8 Hz, 3H). The separation of the two enantiomers was accomplished using the following conditions:
Prep SFC Method Info:
Column/dimensions: Chiralpak AD-H (250×30) mm, 5u
% CO2: 60%
% Co solvent: 40% of 0.2% DEA in MeOH
Total Flow: 120.0 g/min
Back Pressure: 100 bar
Temperature: 30° C.
UV: 244 nm
Analytical Chiral SFC Conditions:
Analytical Column: Chiralpak AD-H (250×4.6) mm; 5u
BPR pressure: 100 bars
Temperature: 30° C.
Flow rate: 4 g/min
Mobile Phase: 0.2% DEA in MeOH
Detector Wavelength: UV 200-400 nm
Enantiomer 1: (300 mg, 0.706 mmol, 24% yield); chiral SFC $t_R$=7.91 min; LC-MS, [M+H]$^+$=417.1, (Method C: $t_R$=4.14 min);
Enantiomer 2: (300 mg, 0.706 mmol, 24% yield); chiral SFC $t_R$=11.1 min; LC-MS, [M+H]$^+$=417.2, (Method C: $t_R$=3.96 min);

Step-2. Synthesis of 4-(3-methylpiperazin-1-yl)phenol: To a degassed solution benzyl 4-(4-(benzyloxy)phenyl)-2-methylpiperazine-1-carboxylate (0.2 g, 0.480 mmol, enantiomer-1) in MeOH (5 mL), was added 10% Pd/C (0.05 g, 0.470 mmol), AcOH (2.5 mL, 43.7 mmol) and stirred the mixture at rt under hydrogen pressure (~1 atm) for 12 h. The reaction mixture was filtered through Celite pad, washed with excess MeOH (20 mL) and filtrate was concentrated under reduced pressure to give the crude residue. The crude residue was basified with aq.10% NaHCO$_3$ solution and extracted with DCM (4×40 mL). The combined organic extracts were dried over sodium sulphate and concentrated under reduced pressure to afford 4-(3-methylpiperazin-1-yl)phenol (0.05 g, 0.229 mmol, 48% yield) as a brown semi solid. LC/MS [M+H]$^+$=193.2, $t_R$=0.60 min (Method F).

Step-3. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)(4-(4-hydroxyphenyl)-2-methylpiperazin-1-yl)methanone: Prepared in a similar fashion as described in Example 1 by using (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.02 g, 0.057 mmol) and 4-(3-methylpiperazin-1-yl)phenol, isomer-1 (0.027 g, 0.142 mmol) to get crude product which was purified by prep-HPLC [Method A] to afford Example 36 ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)(4-(4-hydroxyphenyl)-2-methylpiperazin-1-yl)methanone (3.2 mg, 5.94 μmol, 11% yield). LC-MS, [M+H]$^+$=528.1, (Method A: $t_R$=1.10). $^1$H NMR (400 MHz, CD$_3$OD): δ ppm 8.52 (s, 1H), 7.68 (d, J=8.1 Hz, 1H), 7.62 (d, J=9.5 Hz, 1H), 7.51-7.41 (m, 1H), 7.08 (t, J=8.4 Hz, 1H), 6.86 (dd, J=8.3, 6.1 Hz, 2H), 6.75-6.68 (m, 2H), 4.98-4.89 (m, 1H), 4.58-4.46 (m, 1H), 4.33 (d, J=8.8 Hz, 1H), 4.17-4.09 (m, 2H), 3.94-3.87 (m, 2H), 3.82-3.69 (m, 4H), 3.64-3.54 (m, 1H), 3.41-3.39 (m, 1H), 2.87-2.72 (m, 1H), 1.57-1.36 (m, 3H). (rotameric mixture) hGal3 IC$_{50}$=0.34 μM.

Example 37. ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((2R,5S)-4-(4-hydroxyphenyl)-2,5-dimethylpiperazin-1-yl)methanone

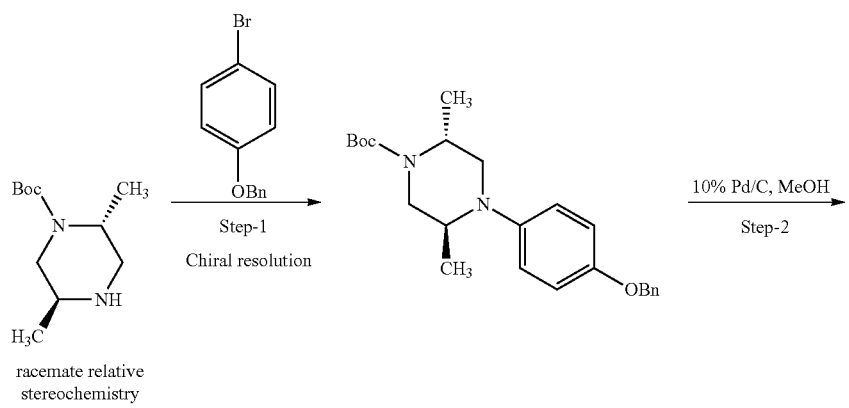

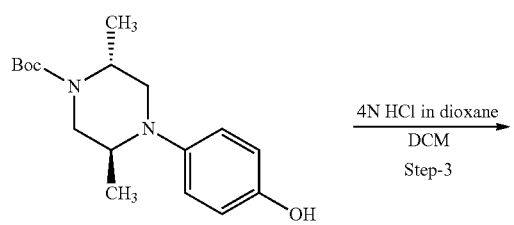

-continued

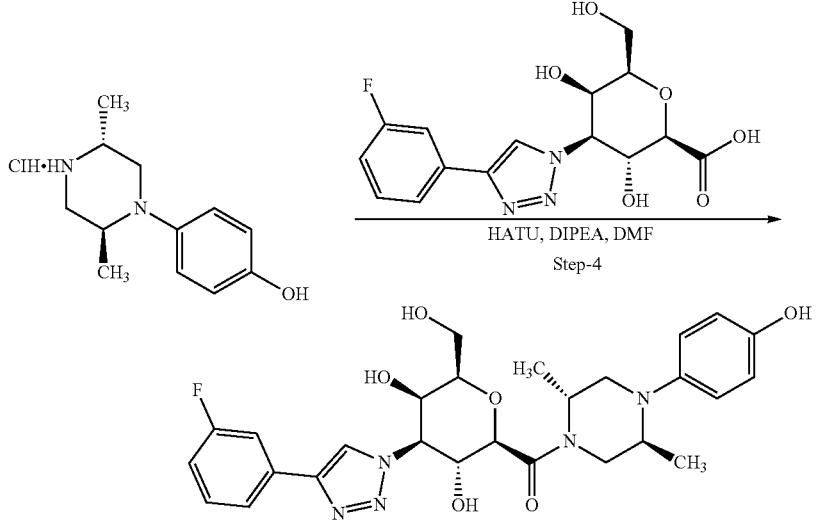

HATU, DIPEA, DMF
Step-4

Step-1. Synthesis of (2R, 5S)-tert-butyl 4-(4-(benzyloxy)phenyl)-2,5-dimethyl piperazine-1-carboxylate: Dried vial was charged with trans-tert-butyl 2,5-dimethyl piperazine-1-carboxylate (0.5 g, 2.333 mmol), 1-(benzyloxy)-4-bromobenzene (0.921 g, 3.50 mmol), potassium tert-butoxide (0.39 g, 3.50 mmol), tri-tert-butylphosphine (0.024 g, 0.117 mmol), toluene (5 mL) and reaction mixture was degassed with nitrogen for 10 min. Then Pd$_2$(dba)$_3$ (0.107 g, 0.117 mmol) was added, vial was sealed and heated at 110° C. for overnight. The reaction mixture was cooled to room temperature, filtered through Celite pad, washed with excess and filtrate was concentrated under reduced pressure to give crude residue. The crude residue was purified by flash chromatography (10-30% EtOAc in n-hexane) to afford (2R,5S)-tert-butyl 4-(4-(benzyloxy)phenyl)-2,5-dimethyl piperazine-1-carboxylate (300 mg) as racemate. LC/MS [M+H]$^+$=397.2, t$_R$=4.15 min (Method C). $^1$H NMR (300 MHz, CDCl$_3$): δ ppm 7.46-7.30 (m, 10H), 6.95-6.84 (m, 4H), 5.17 (s, 2H), 5.03 (s, 2H), 4.43 (br. s., 1H), 4.04 (d, J=13.2 Hz, 1H), 3.40-3.27 (m, 2H), 3.23 (d, J=11.7 Hz, 1H), 2.85 (dd, J=11.7, 3.8 Hz, 1H), 2.73-2.61 (m, 1H), 1.36 (d, J=6.8 Hz, 3H). The separation of the two enantiomers was accomplished using the following conditions:

Prep SFC Method Info:
Column/dimensions: Chiralcel OJ-H (250×30) mm, 5u
% CO2: 60%
% Co solvent: 40% of 0.2% DEA in MeOH
Total Flow: 110.0 g/min
Back Pressure: 100 bar
Temperature: 30° C.
UV: 250 nm
Analytical Chiral SFC Conditions:
Analytical Column: Chiralcel OJ-H (250×30) mm, 5u
BPR pressure: 100 bars
Temperature: 30° C.
Flow rate: 3 g/min
Mobile Phase: 0.2% DEA in MeOH
Detector Wavelength: UV 200-400 nm
Enantiomer 1: (0.13 g, 0.328 mmol, 14% yield); chiral SFC t$_R$=2.97 min; LC-MS, [M+H]$^+$=397.4, (Method C: t$_R$=4.02 min);
Enantiomer 2: (0.13 g, 0.328 mmol, 14% yield); chiral SFC t$_R$=3.61 min; LC-MS, [M+H]$^+$=397.2, (Method C: t$_R$=4.16 min);

Step-2. Synthesis of (2R,5S)-tert-butyl 4-(4-hydroxyphenyl)-2,5-dimethyl piperazine-1-carboxylate (relative stereochemistry, homochiral): To a degassed solution (2R, 5S)-tert-butyl 4-(4-(benzyloxy)phenyl)-2,5-dimethylpiperazine-1-carboxylate (0.09 g, 0.227 mmol, enantiomer-1) in MeOH (5 mL), was added 10% Pd/C (0.024 g, 0.023 mmol)) and stirred the mixture at rt under hydrogen pressure (~1 atm) for 12 h. The reaction mixture was filtered through Celite pad, washed with excess MeOH (20 mL) and filtrate was concentrated under reduced pressure to give 2R,5S)-tert-butyl 4-(4-hydroxyphenyl)-2,5-dimethylpiperazine-1-carboxylate (0.04 g, 0.131 mmol, 57% yield) as a pale pink solid which was as such taken for next step without further purification. LC/MS [M+H]$^+$=307.2, t$_R$=1.90 min (Method F). $^1$H NMR (300 MHz, CDCl$_3$): δ ppm 6.77 (s, 4H), 4.39 (br. s., 1H), 3.80-3.75 (m, 2H), 3.45 (d, J=13.5 Hz, 1H), 3.25-3.24 (m, 1H), 2.89 (d, J=11.4 Hz, 1H), 1.49 (s, 9H), 1.27 (d, J=6.8 Hz, 3H), 0.95 (d, J=6.8 Hz, 3H).

Step-3. Synthesis of 4-((2S, 5R)-2,5-dimethylpiperazin-1-yl)phenol, HCl (relative stereochemistry, homochiral): To an ice cooled stirred solution (2R,5S)-tert-butyl 4-(4-hydroxyphenyl)-2,5-dimethylpiperazine-1-carboxylate (0.04 g, 0.131 mmol) in DCM (1 mL), HCl (4M in dioxane) (0.5 mL, 2.000 mmol) was added. The reaction mixture was allowed to reach room temperature and stirred for 2 h. Solvent was removed under reduced pressure and dried to afford 4-((2S,5R)-2, 5-dimethylpiperazin-1-yl)phenol, HCl (0.03 g, 0.124 mmol, 95% yield) as a white solid. LC/MS [M+H]$^+$=207.2, t$_R$=0.65 min (Method F).

Step-4. Prepared in a similar fashion as described in Example 1 by using (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.02 g, 0.057 mmol) and 4-((2S,5R)-2,5-dimethylpiperazin-1-yl)phenol, HCl (0.03 g, 0.124 mmol, isomer-1) to get crude product which was purified by prep-HPLC [Method A] to afford Example 37a ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((2R,5S)-4-(4-hydroxyphenyl)-2,5-dimethylpiperazin-1-yl)methanone, Isomer 1 (1 mg, 1.846 μmol, 3% yield). LC-MS, [M+H]$^+$=542.1, (Method A: t$_R$=1.36). $^1$H NMR (400 MHz, CD$_3$OD): δ ppm 8.53 (s, 1H), 7.70-7.59 (m, 2H), 7.50-7.42 (m, 1H), 7.11-7.05 (m, 1H), 6.84-6.67 (m, 4H), 4.99-4.89 (m, 1H), 4.78-4.64 (m, 1H), 4.61-4.53 (m, 1H), 4.38-4.31 (m, 1H), 4.17-4.15 (m, 1H), 3.99-3.70 (m, 6H), 3.50-3.39 (m, 1H), 2.99 (d, J=12.2 Hz, 1H), 1.51-1.27 (m, 3H), 1.03-0.85 (m, 3H). hGal3 $IC_{50}$=0.35 µM.

Example 37b: Prepared in a similar fashion as described for Example 37a, by using (2R, 5S)-tert-butyl 4-(4-(benzyloxy)phenyl)-2,5-dimethylpiperazine-1-carboxylate enantiomer 2 as the starting material in Step 2. LC-MS, [M+H]+= 542.1, {Method A: $t_R$=1.36 min}. $^1$H NMR (400 MHz, METHANOL-d4) δ ppm 8.53 (s, 1H), 7.68 (d, J=7.8 Hz, 1H), 7.62 (d, J=10.8 Hz, 1H), 7.50-7.42 (m, 1H), 7.12-7.04 (m, 1H), 6.81 (d, J=6.8 Hz, 2H), 6.71 (d, J=9.0 Hz, 2H), 4.91 (d, J=12.0 Hz, 1H), 4.55 (br. s., 1H), 4.38-4.24 (m, 2H), 4.15 (d, J=3.9 Hz, 1H), 3.90 (d, J=15.9 Hz, 3H), 3.83-3.67 (m, 3H), 3.47-3.35 (m, 1H), 3.03-2.94 (m, 1H), 1.50-1.34 (m, 3H), 1.02-0.85 (m, 3H). hGal3 $IC_{50}$=0.31 µM.

Example 38. ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((3aR,6aS)-5-(p-tolyl)hexahydropyrrolo[3,4-c]pyrrol-2(1H)-yl)methanone to rt, filtered through Celite pad, washed with EtOAc (20 mL) and the filtrate was concentrated under reduced pressure to give crude residue. The crude residue was purified by flash chromatography (20-25%% EtOAc in pet ether) to afford of (3aR,6aS)-tert-butyl 5-(p-tolyl)hexahydropyrrolo[3,4-c]pyrrole-2(1H)-carboxylate (110 mg, 0.36 mmol, 30% yield). LC/MS [M+H]$^+$=303.2, (Method F: $t_R$=2.46 min).

Step-2. Synthesis of (3aR,6aS)-2-(p-tolyl)octahydropyrrolo[3,4-c]pyrrole hydrochloride: To a stirred solution (3aR,6aS)-tert-butyl 5-(p-tolyl)hexahydro pyrrolo[3,4-c]pyrrole-2(1H)-carboxylate (105 mg, 0.347 mmol) in DCM (5 mL), HCl (4M in dioxane) (2 mL, 8.00 mmol) was added. The reaction mixture was allowed to reach room temperature and stirred for 2 h. The reaction mass concentrated under reduced pressure and the crude residue was triturated with n-Pentane and dried under reduced pressure to afford (3aR,6aS)-2-(p-tolyl)octahydropyrrolo[3,4-c]pyrrole hydrochloride. LC/MS [M+H]$^+$=203.2, $t_R$=2.17 min (Method F).

Step-3. Synthesis of ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((3aR,6aS)-5-(p-tolyl)hexahydropyrrolo[3,4-c]pyrrol-2(1H)-yl)methanone:

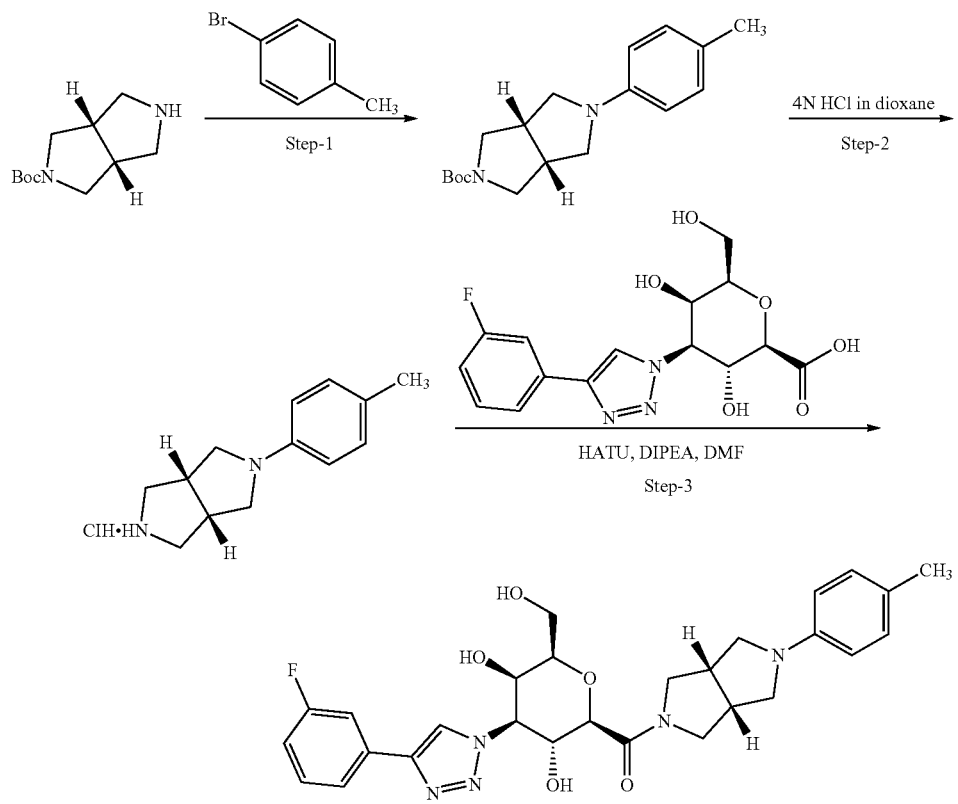

Step-1. Synthesis of (3aR,6aS)-tert-butyl 5-(p-tolyl)hexahydropyrrolo[3,4-c]pyrrole-2(1H)-carboxylate: To a stirred solution of cis-2-boc-hexahydropyrrolo[3,4-c]pyrrole (250 mg, 1.178 mmol) in toluene (5 mL), was added BINAP (147 mg, 0.236 mmol), sodium tert-butoxide (340 mg, 3.53 mmol) and 1-bromo-4-methylbenzene (242 mg, 1.413 mmol) sequentially. The reaction mixture was degassed with Ar for 10 min and tris(dibenzylideneacetone)dipalladium(0) (108 mg, 0.118 mmol) was added and reaction mixture was heated at 80° C. for 14 h. The reaction mixture was cooled Prepared in a similar fashion as described in Example 1 by using (2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carboxylic acid (0.02 g, 0.057 mmol) and (3aR,6aS)-2-(p-tolyl)octahydropyrrolo[3,4-c]pyrrole hydrochloride (0.02 g, 0.84 mmol) to get crude product which was purified by prep-HPLC [Method A] to afford Example 38 ((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)((3aR,6aS)-5-(p-tolyl)hexahydropyrrolo[3,4-c]pyrrol-2(1H)-yl)methanone (1.8 mg, 6% yield). LC-MS, [M+H]$^+$=538.1, (Method B: $t_R$=1.61). $^1$H NMR (400 MHz, CD$_3$OD): δ ppm 8.52, 8.50* (s, 1H), 7.65-7.73 (m, 1H), 7.55-7.65 (m, 1H), 7.49-7.42 (m, 1H), 7.05-7.15 (m, 1H), 7.02-6.96 (m, 2H), 6.45-6.61 (m, 2H), 4.90-4.96 (m, 1H), 4.66-4.63 (m, 1H), 4.31 (dd, J=9.3, 3.8 Hz, 1H), 4.03-4.17 (m, 2H), 3.67-3.94 (m, 6H), 3.45-3.57 (m, 3H), 3.05-3.30 (m, 3H), 2.23, 2.21* (s, 3H). hGal3 IC$_{50}$=0.40 μM.

Example 39a and Example 39b. (2R,3R,4R,5R,6S)-4-(4-(3-fluorophenyl)-1H-1,2,3-triazol-1-yl)-2-(hydroxymethyl)-6-((2-(hydroxymethyl)-4-(4-hydroxyphenyl)piperazin-1-yl)methyl)tetrahydro-2H-pyran-3,5-diol

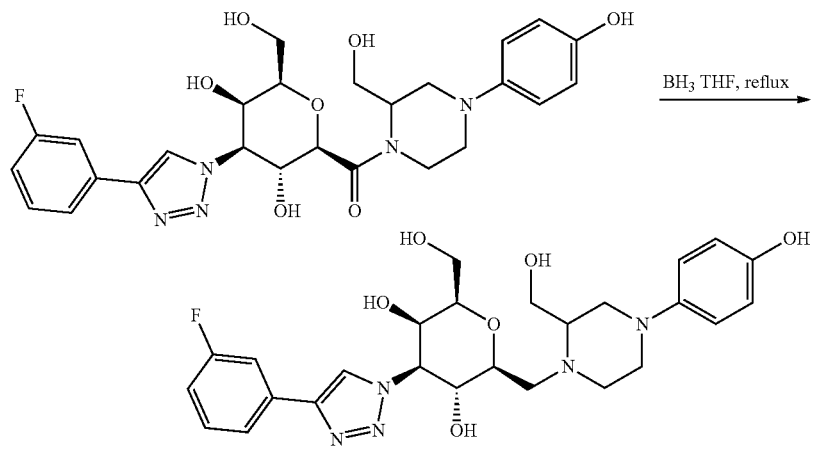

((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)(2-(hydroxymethyl)-4-(4-hydroxyphenyl)piperazin-1-yl)methanone, example 34a (10 mg, 0.018 mmol) was suspended in borane tetrahydrofuran complex (5.5 mL, 5.52 mmol, 1M in THF) and refluxed at 70° C. overnight. The reaction mixture was cooled to 0° C., quenched with MeOH (10 mL) and solvent was removed under reduced pressure to give crude residue. The crude residue was purified by preparative HPLC [Method A] to afford Example 39a (2R,3R,4R,5R,6S)-4-(4-(3-fluorophenyl)-1H-1,2,3-triazol-1-yl)-2-(hydroxymethyl)-6-((2-(hydroxymethyl)-4-(4-hydroxyphenyl)piperazin-1-yl)methyl)tetrahydro-2H-pyran-3,5-diol, Isomer 1 (0.4 mg, 0.755 μmol, 4% yield). LC/MS [M+H]$^+$=530.2, $t_R$=1.10 min (Method A). $^1$H NMR (400 MHz, METHANOL-d$_4$) δ ppm 8.47 (s, 1H), 7.58-7.69 (m, 2H), 7.46 (td, J=8.01, 5.99 Hz, 1H), 7.08 (td, J=8.62, 2.32 Hz, 1H), 6.86-6.92 (m, 2H), 6.69-6.75 (m, 2H), 4.81 (d, J=2.93 Hz, 1H), 4.20-4.28 (m, 1H), 4.12 (d, J=2.93 Hz, 1H), 3.62-3.85 (m, 5H), 3.34-3.39 (m, 2H), 3.10-3.26 (m, 3H), 2.67-2.98 (m, 5H). hGal3 IC$_{50}$=0.31 μM.

Example 39b: Prepared in a similar fashion as described for Example 39a, by using Example 34b as the starting material. LC-MS, [M+H]$^+$=530.2, (Method A: $t_R$=1.13 min). $^1$H NMR (400 MHz, MeOH-d$_4$) δ ppm 8.47 (s, 1H), 7.58-7.69 (m, 2H), 7.46 (td, J=8.01, 5.99 Hz, 1H), 7.08 (td, J=8.62, 2.32 Hz, 1H), 6.86-6.92 (m, 2H), 6.69-6.75 (m, 2H), 4.81 (d, J=2.9 Hz, 1H), 4.20-4.28 (m, 1H), 4.12 (d, J=2.9 Hz, 1H), 3.62-3.85 (m, 5H), 3.34-3.39 (m, 2H), 3.10-3.26, (m, 3H), 2.67-2.98 (m, 5H). hGal3 IC$_{50}$=0.39 μM.

Example 40a and Example 40b. (2R,3R,4R,5R,6S)-4-(4-(3-fluorophenyl)-1H-1,2,3-triazol-1-yl)-2-(hydroxymethyl)-6-((3-(hydroxymethyl)-4-(4-hydroxyphenyl)piperazin-1-yl)methyl)tetrahydro-2H-pyran-3,5-diol

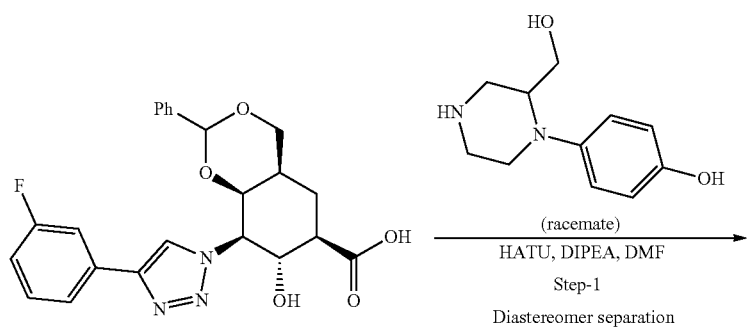

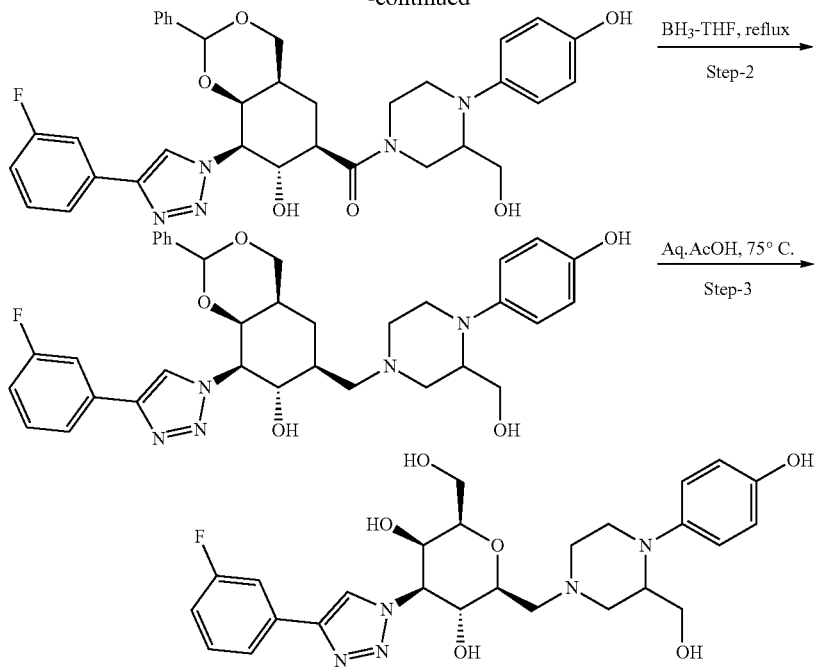

Step-1. Synthesis of ((4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)(3-(hydroxymethyl)-4-(4-hydroxyphenyl)piperazin-1-yl)methanone: To a stirred solution of (4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carboxylic acid (75 mg, 0.170 mmol) and 4-(2-(hydroxymethyl)piperazin-1-yl)phenol (53.1 mg, 0.255 mmol) in DMF (0.6 mL) was added DIPEA (0.297 mL, 1.699 mmol) and HATU (129 mg, 0.340 mmol) at room temperature and stirred for 16 h. The reaction mixture was quenched with ice cold water (20 mL) and stirred for 10 min. The obtained solid was filtered, washed with excess water and dried to afford diastereomeric mixture of ((4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)(3-(hydroxymethyl)-4-(4-hydroxyphenyl)piperazin-1-yl)methanone (80 mg, 0.127 mmol, 74.5% yield) as an off white solid. LC/MS [M+H]$^+$=632.3, $t_R$=1.00 min (Method D). The separation of the two diastereomers was accomplished using the following conditions:
Preparative SFC Conditions
Column/dimensions: Chiralpak AS-H (250×21) mm, 5u
% CO2: 60%
% Co solvent: 40% (0.2% DEA IN METHANOL)
Total Flow: 60.0 g/min
Back Pressure: 100 bar
Temperature: 30° C.
UV: 245 nm
Analytical Chiral SFC Conditions:
Column/dimensions: Chiralpak AS-H (250×4.6) mm, 5u
% CO2: 70%
% Co solvent: 30% (0.2% DEA IN METHANOL)
Total Flow: 3.0 g/min
Back Pressure: 100 bar
Temperature: 30° C.
UV: 245 nm Diastereomer 1: (20 mg, 0.032 mmol, 19% yield); chiral SFC $t_R$=3.53 min; LC-MS, [M+H]$^+$=632.2, (Method C: $t_R$=1.60 min);
Diastereomer 2: (20 mg, 0.032 mmol, 19% yield); chiral SFC $t_R$=6.37 min; LC-MS, [M+H]$^+$=632.2, (Method C: $t_R$=2.20 min);

Step-2. Synthesis of (4aR,6S,7R,8R,8aR)-8-(4-(3-fluorophenyl)-1H-1,2,3-triazol-1-yl)-6-((3-(hydroxymethyl)-4-(4-hydroxyphenyl)piperazin-1-yl)methyl)-2-phenyl hexahydropyrano[3,2-d][1,3]dioxin-7-ol: A mixture of ((4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)(3-(hydroxymethyl)-4-(4-hydroxyphenyl)piperazin-1-yl)methanone (20 mg, 0.032 mmol, diastereomer-1) and borane tetrahydrofuran complex (9.5 mL, 9.50 mmol, 1M in THF) was refluxed at 75° C. for 16 h. The reaction mixture was cooled to 0° C., quenched with MeOH (10 mL) and solvent was removed under reduced pressure to give (4aR,6S,7R,8R,8aR)-8-(4-(3-fluorophenyl)-1H-1,2,3-triazol-1-yl)-6-((3-(hydroxymethyl)-4-(4-hydroxyphenyl)piperazin-1-yl)methyl)-2-phenylhexahydro pyrano[3,2-d][1,3]dioxin-7-ol (quantitative, crude) which was taken as such for next step without further purification. LC/MS [M+H]$^+$=618.2, $t_R$=0.99 min (Method D).

Step-3. A mixture of (4aR,6S,7R,8R,8aR)-8-(4-(3-fluorophenyl)-1H-1,2,3-triazol-1-yl)-6-((3-(hydroxymethyl)-4-(4-hydroxyphenyl)piperazin-1-yl)methyl)-2-phenyl hexahydropyrano[3,2-d][1,3]dioxin-7-ol (20 mg, 0.032 mmol) and acetic acid (70% in water) (10 mL) was heated at 75° C. for 16 h. The reaction mixture was cooled to rt and solvent was removed under reduced pressure to give crude residue. The crude residue was purified by preparative HPLC [Method A] to afford Example 40a (2R,3R,4R,5R,6S)-4-(4-(3-fluorophenyl)-1H-1,2,3-triazol-1-yl)-2-(hydroxymethyl)-6-((3-(hydroxymethyl)-4-(4-hydroxyphenyl)piperazin-1-yl) methyl)tetrahydro-2H-pyran-3,5-diol, Isomer 1 (2.4 mg, 4.44 µmol, 14% yield) as a pure product. LC/MS [M+H]$^+$= 530.3, $t_R$=1.09 min (Method C). $^1$H NMR (400 MHz, MEOH-d4) δ ppm 8.48 (s, 1H), 7.71-7.56 (m, 2H), 7.50-7.35 (m, 1H), 7.08 (td, J=8.6, 2.2 Hz, 1H), 6.97 (d, J=8.8 Hz, 2H), 6.74 (d, J=8.8 Hz, 2H), 4.27 (t, J=9.8 Hz, 1H), 4.13 (d, J=2.7 Hz, 1H), 3.88-3.62 (m, 4H), 3.60-3.37 (m, 3H), 3.20-2.81 (m, 8H), (1H might be obscured with solvent moisture peak). hGal3 IC$_{50}$=0.94 µM.

Example 40b: Prepared in a similar fashion as described for Example 40a, by using ((4aR,6R,7R,8R,8aR)-8-(4-(3-fluorophenyl)-1H-1,2,3-triazol-1-yl)-7-hydroxy-2-phenyl-hexahydropyrano[3,2-d][1,3]dioxin-6-yl)(3-(hydroxymethyl)-4-(4-hydroxyphenyl)piperazin-1-yl)methanone Isomer-2 as the starting material in Step 2. LC-MS, [M+H]$^+$=530.2, (Method A: t$_R$=1.09 min). $^1$H NMR (400 MHz, MeOH-d4) δ ppm 8.49 (s, 1H), 7.71-7.58 (m, 2H), 7.52-7.38 (m, 1H), 7.15-6.95 (m, 3H), 6.76 (d, J=8.8 Hz, 2H), 4.56 (s, 1H), 4.31-4.09 (m, 2H), 3.87-3.66 (m, 4H), 3.55-3.37 (m, 2H), 3.25-2.87 (m, 8H), (1H might be obscured with solvent peak) hGal3 IC$_{50}$=1.6 µM.

Example-41. Synthesis of N-(6-((1S,4S)-5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl)-2,5-diazabicyclo[2.2.1]heptan-2-yl)pyridin-3-yl)methanesulfonamide Step-1. Synthesis (1S,4S)-tert-butyl 5-(5-nitropyridin-2-yl)-2,5-diazabicyclo[2.2.1]heptane-2-carboxylate: To a stirred solution 2-bromo-5-nitropyridine (0.6 g, 2.96 mmol) in DMSO (10 mL), potassium carbonate (0.82 g, 5.91 mmol), (1S,4S)-tert-butyl 2,5-diazabicyclo[2.2.1]heptane-2-carboxylate (0.88 g, 4.43 mmol), and TBAI (0.11 g, 0.296 mmol) were added sequentially at rt. Then the reaction mixture was heated at 70° C. for 12 h. The reaction mixture was cooled to room temperature, filtered through Celite pad and washed with EtOAc (30 mL). Then the filtrate was washed with water, brine solution, dried over Na$_2$SO$_4$ and concentrated under reduced pressure to give crude compound. The crude residue was purified by flash chromatography (0-50% EtOAc in pet ether) to afford (1S,4S)-tert-butyl 5-(5-nitropyridin-2-yl)-2,5-diazabicyclo[2.2.1]heptane-2-carboxylate (0.8 g, 2.497 mmol, 84% yield). LC/MS [M+H]$^+$=321.1, t$_R$=2.56 min (Method F).

Step-2. Synthesis of (1S,4S)-tert-butyl 5-(5-aminopyridin-2-yl)-2,5-diazabicyclo[2.2.1]heptane-2-carboxylate: To a degassed stirred solution (1S,4S)-tert-butyl 5-(5-nitropyridin-2-yl)-2,5-diazabicyclo[2.2.1]heptane-2-carboxylate (0.2 g, 0.624 mmol) in MeOH (4 mL) was added 10% Pd/C (0.332 g, 0.312 mmol) under N$_2$. Then the reaction mixture

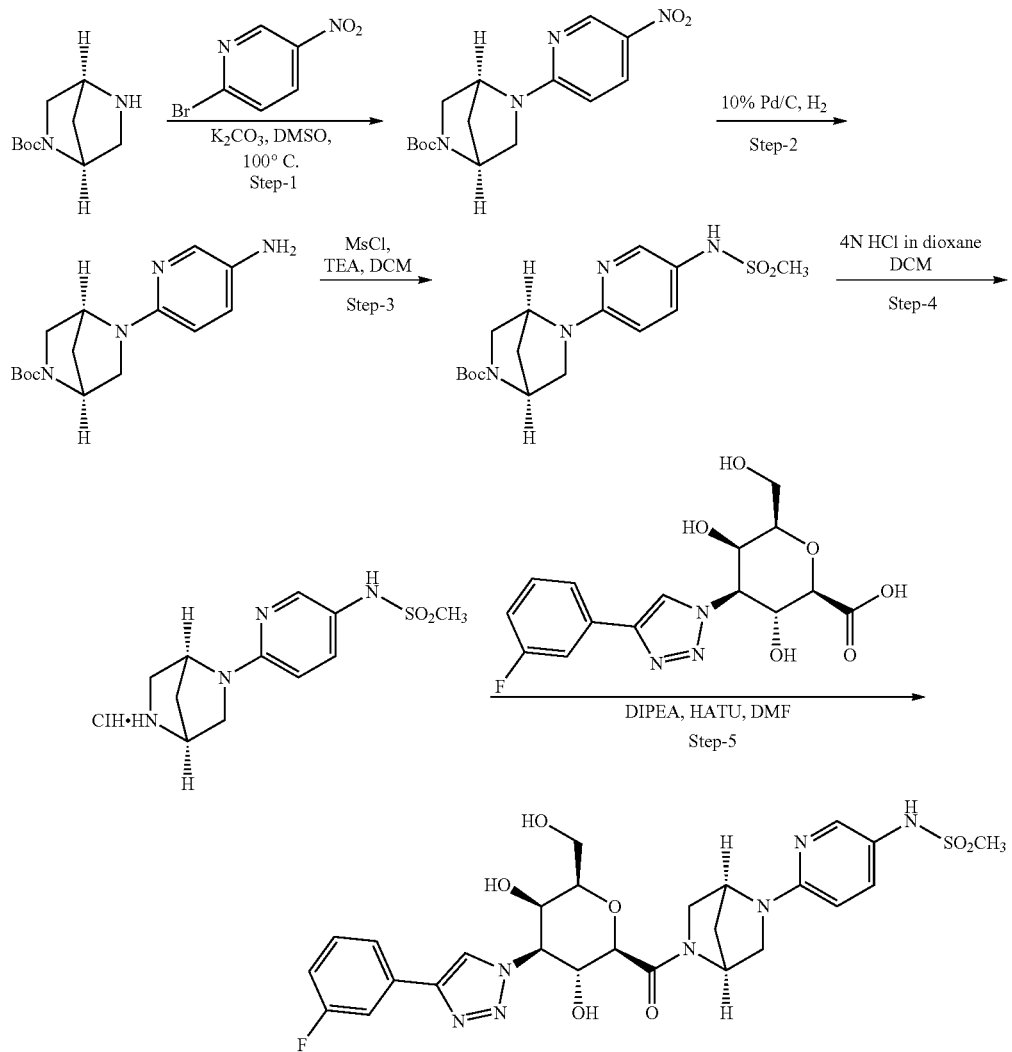

was stirred under H$_2$ atm at ambient temperature for 12 h. The reaction mixture was filtered through Celite pad, washed with MeOH (20 mL) and filtrate was evaporated under reduced pressure to afford (1 S,4S)-tert-butyl 5-(5-aminopyridin-2-yl)-2,5-diazabicyclo[2.2.1]heptane-2-carboxylate (0.17 g, 0.585 mmol, 94% yield) as a color less liquid which was as such taken for next step without further purification. LC/MS [M+H]$^+$=291.3, (Method F: t$_R$=1.36 min).

Step-3. Synthesis of (1S,4S)-tert-butyl 5-(5-(methylsulfonamido)pyridin-2-yl)-2,5-diazabicyclo[2.2.1]heptane-2-carboxylate: To an ice cooled stirred solution of (1S,4S)-tert-butyl 5-(5-aminopyridin-2-yl)-2,5-diazabicyclo[2.2.1]heptane-2-carboxylate (160 mg, 0.551 mmol) in DCM (3 mL), were added DIPEA (0.19 mL, 1.10 mmol) and Mesyl-Cl (0.04 mL, 0.551 mmol) were added sequentially under Nitrogen. The reaction mixture was allowed to warm to rt and stirred for 2 h. The reaction mixture was extracted with DCM (2×30 mL), washed with water, brine, dried over Na$_2$SO$_4$ and solvent was removed under reduced pressure to give (1S,4S)-tert-butyl 5-(5-(methylsulfonamido) pyridin-2-yl)-2,5-diazabicyclo[2.2.1]heptane-2-carboxylate (150 mg, 0.407 mmol, 74% yield) which was as such taken for next step without further purification. LC/MS [M+H]$^+$=369.1, (Method E: t$_R$=0.99 min.

Step-4. Synthesis of N-(6-((1S,4S)-2,5-diazabicyclo [2.2.1]heptan-2-yl)pyridin-3-yl)methanesulfonamide: To a stirred solution of (1S,4S)-tertbutyl-5-(5-(methylsulfonamido)pyridin-2-yl)-2,5-diazabicyclo[2.2.1]heptane-2-carboxylate (0.1 g, 0.271 mmol) in DCM (4 mL), was added 4N HCl in dioxane (0.35 mL, 1.36 mmol) at 0° C. The reaction mixture was allowed to reach room temperature and stirred for 2 h. Then the solvent as removed under reduced pressure, triturated with Et$_2$O (2×5 mL) to give N-(6-((1S,4S)-2,5-diazabicyclo[2.2.1]heptan-2-yl)pyridin-3-yl)methane sulfonamide (60 mg, 0.224 mmol, 82% yield) as an off-white solid which was as such taken for next step without further purification. LC/MS [M+H]$^+$=269.2, (Method E: t$_R$=0.39 min).

Step-5. Synthesis of N-(6-(4-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-carbonyl) piperazin-1-yl)pyridin-3-yl)methanesulfonamide: Prepared in a similar fashion as described in Example 24 by using (2R,3R,4S,5R, 6R)-4-(4-(3-fluorophenyl)-1H-1,2,3-triazol-1-yl)-3,5-dihydroxy-6-(hydroxymethyl)tetrahydro-2H-pyran-2-carboxylic acid (20 mg, 0.057 mmol) and N-(6-((1S,4S)-2,5-diazabicyclo[2.2.1]heptan-2-yl)pyridin-3-yl)methanesulfonamide (30.4 mg, 0.113 mmol). The crude product was purified by preparative HPLC [Method A] to yield Example 41 (5.1 mg, 8.36 µmol, 15% yield). LC-MS, [M+H]$^+$=604.2, (Method A, t$_R$=1.07 min). $^1$H NMR (400 MHz, MEOH-d$_4$) δ ppm=8.40, 8.38* (s, 1H), 7.90-7.86 (m, 1H), 7.57-7.48 (m, 2H), 7.44-7.32 (m, 2H), 6.99-6.95 (m, 1H), 6.49-6.45 (m, 1H), 5.07-4.73 (m, 2H), 4.69-4.53 (m, 1H), 4.23-4.00 (m, 2H), 3.75-3.38 (m, 8H), 2.81, 2.78*(s, 3H), 2.05-1.93 (m, 2H), (*rotameric mixture). hGal3 IC$_{50}$=0.72 µM.

Example 42 was prepared in an analogous fashion to Example 41, substituting 2-bromo-5-nitropyridine with 5-bromo-2-nitropyridine in the synthetic sequence.

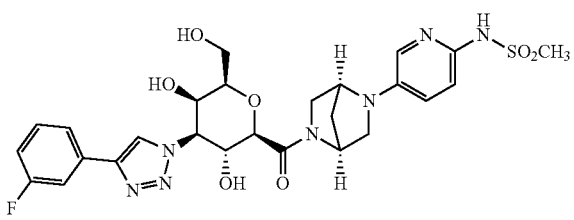 [SMILES: CS(=O)(=O)Nc1ccc(N2C[C@@H]3C[C@H]2CN3C(=O)[C@@H]2O[C@H](CO)[C@H](O)[C@H](n3cc(-c4cccc(F)c4)nn3)[C@H]2O)cn1]

LC/MS [M+H]$^+$=604.2, t$_R$=1.14 min (Method B). $^1$H NMR (400 MHz, MEOH-d$_4$) δ ppm 8.50, 8.47* (s, 1H), 7.75-7.58 (m, 3H), 7.46-7.42 (m, 1H), 7.20-7.10 (m, 1H), 7.09-7.04 (m, 2H), 5.15-4.83 (m, 2H), 4.65-4.60 (m, 2H), 4.32-4.08 (m, 2H), 3.90-3.40 (m, 7H), 3.13, 3.10* (s, 3H), 2.17-1.90 (m, 2H). hGal3 IC$_{50}$=0.42 µM.

We claim:
1. A compound of Formula (I):

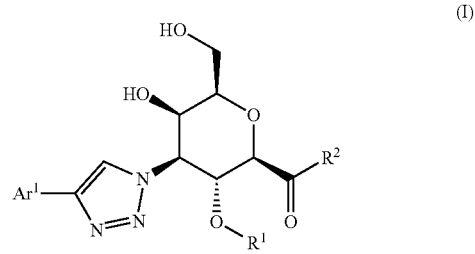

or a pharmaceutically acceptable salt thereof, wherein:
Ar$^1$ is independently phenyl or naphthyl; and wherein each ring moiety is substituted with 1 to 5 substituents selected from cyano, halogen, C$_{1-4}$ alkyl, C$_{1-4}$ alkoxy, C$_{1-4}$ haloalkyl, and C$_{1-4}$ haloalkoxy;
R$^1$ is independently selected from H, C$_{1-4}$ alkyl, and C$_{1-4}$ haloalkyl;
R$^2$ is independently selected from:

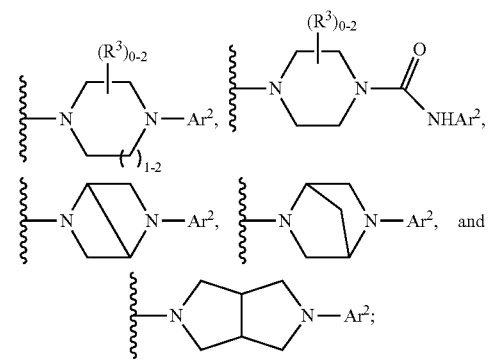

R$^3$ is independently selected from: —CH$_2$OH, halogen, C$_{1-4}$ alkyl, C$_{1-4}$ alkoxy, C$_{1-4}$ haloalkyl, and C$_{1-4}$ haloalkoxy;
Ar$^2$ is independently selected from phenyl,

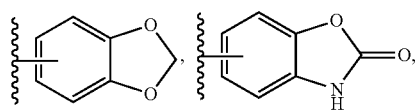

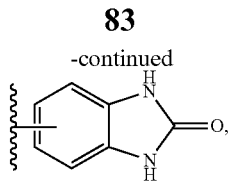

and heteroaryl including from 5 to 10 ring atoms, wherein from 1 to 4 ring atoms are each independently selected from N, N(R⁴), O, and S; and wherein each ring moiety is substituted with 0 to 4 substituents selected from OH, cyano, halogen, $C_{1-4}$ alkyl, $C_{1-4}$ haloalkyl, $C_{1-4}$ alkoxy, $C_{1-4}$ haloalkoxy, N($C_{1-4}$ alkyl)$_2$, —SO$_2$($C_{1-4}$ alkyl), —NHCO$_2$($C_{1-4}$ alkyl), —NHSO$_2$ ($C_{1-4}$ alkyl), —OPh, —OBn, $C_{3-6}$ cycloalkyl, and phenyl substituted with 0 to 1 substituent selected from cyano, halogen, $C_{1-4}$ alkyl, $C_{1-4}$ haloalkyl, $C_{1-4}$ alkoxy, $C_{1-4}$ haloalkoxy, —NH$_2$, —NH($C_{1-4}$ alkyl), and —N($C_{1-4}$ alkyl)$_2$; and R⁴ is independently H or $C_{1-4}$ alkyl.

2. A compound according to claim 1, wherein the compound is of Formula (Ia):

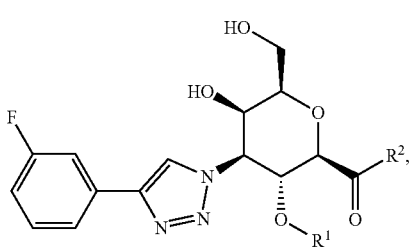

(Ia)

or a pharmaceutically acceptable salt thereof.

3. The compound of claim 2, wherein:
R¹ is independently H or $C_{1-4}$ alkyl;
R² is independently selected from:

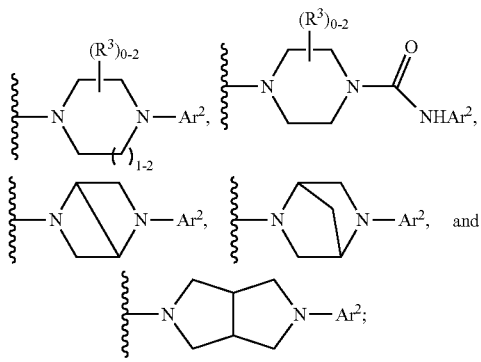

R³ is independently -CH$_2$OH or $C_{1-4}$ alkyl;
Ar² is independently selected from phenyl

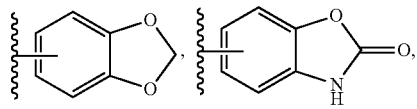

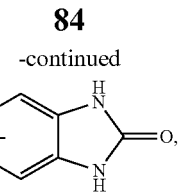

and heteroaryl including from 5 to 10 ring atoms, wherein from 1 to 4 ring atoms are each independently selected from N, N(R⁴), O, and S; and wherein each ring moiety is substituted with 0 to 4 substituents selected from OH, cyano, halogen, $C_{1-4}$ alkyl, $C_{1-4}$ haloalkyl, $C_{1-4}$ alkoxy, $C_{1-4}$ haloalkoxy, N($C_{1-4}$ alkyl)$_2$, —SO$_2$ ($C_{1-4}$ alkyl), —NHCO$_2$ ($C_{1-4}$ alkyl), and —NHSO$_2$($C_{1-4}$ alkyl); and R⁴ is independently H or $C_{1-4}$ alkyl.

4. A compound of claim 3, wherein:
R² is independently selected from:

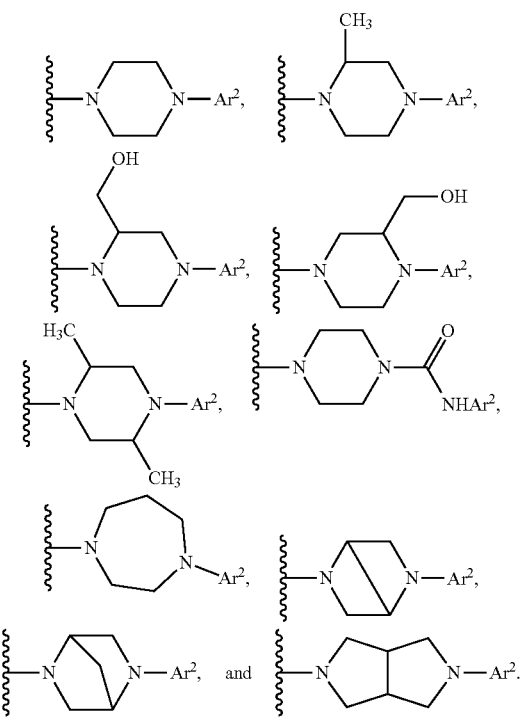

5. A compound of claim 4, wherein:
Ar² is independently selected from:

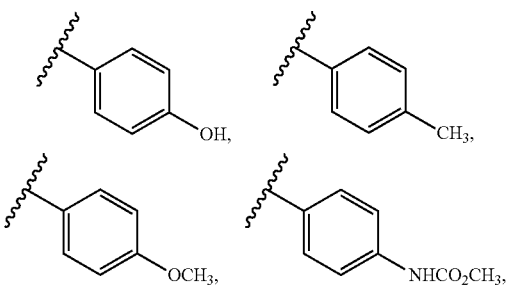

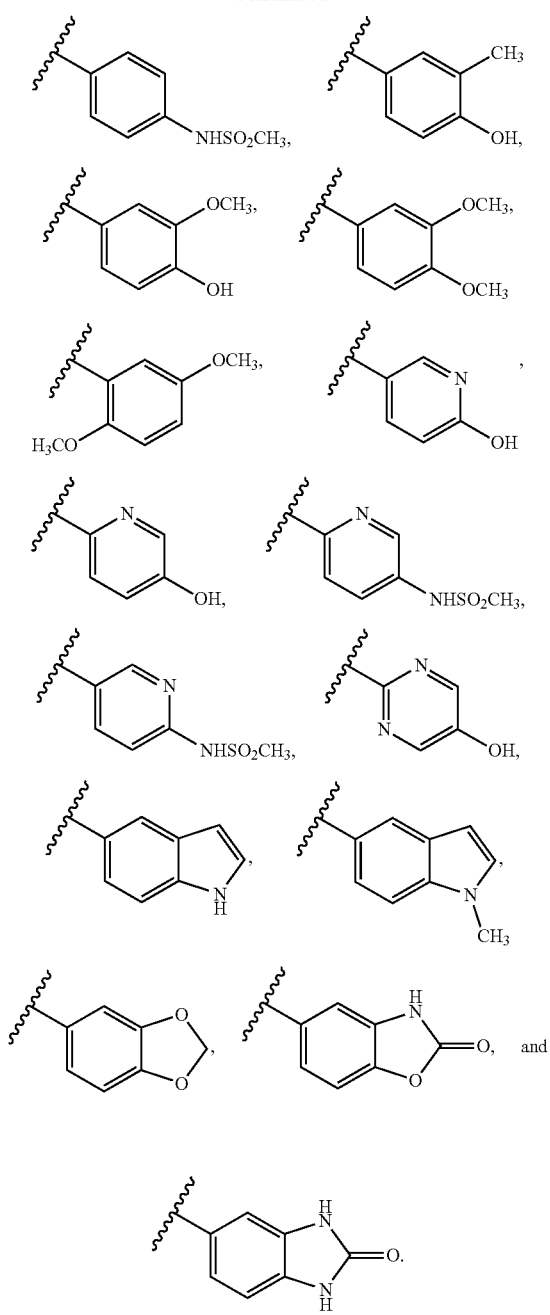
6. A compound of claim 5, wherein:
R¹ is independently H or CH₃.
7. A compound selected from:
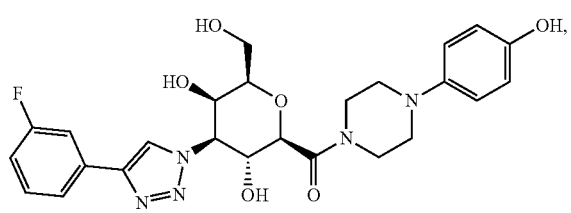
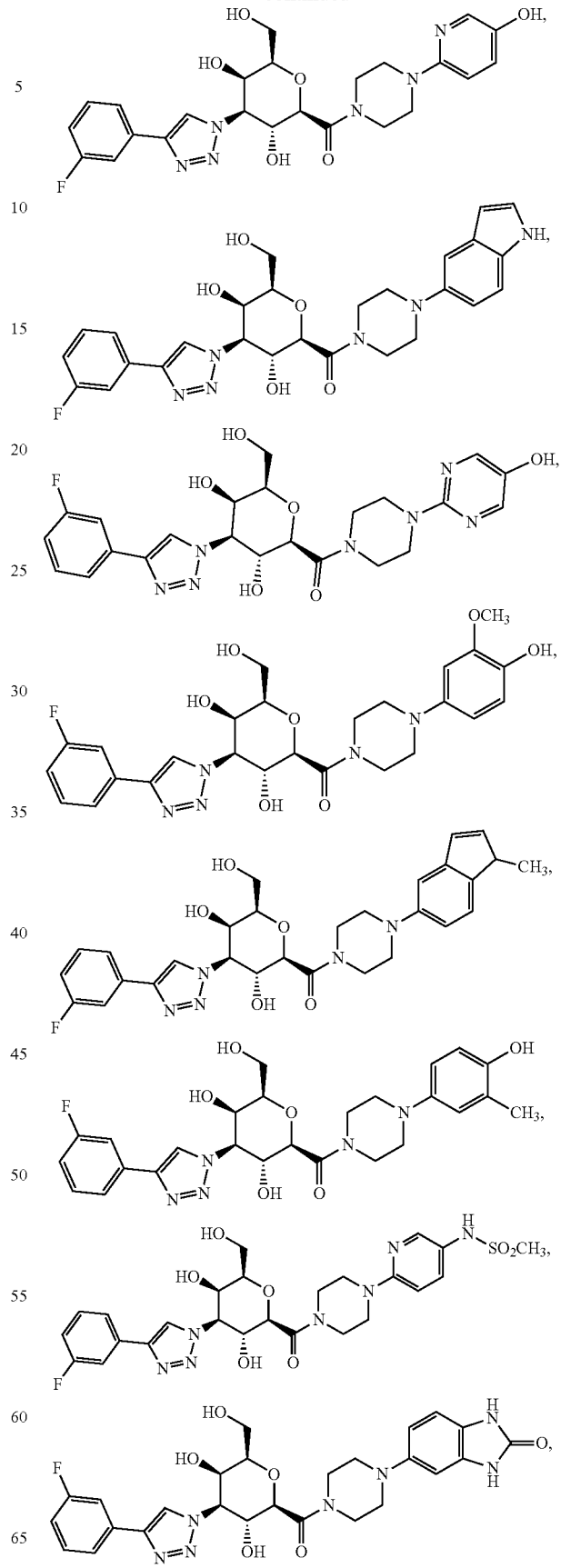

87
-continued
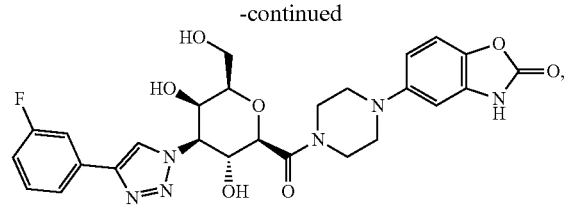
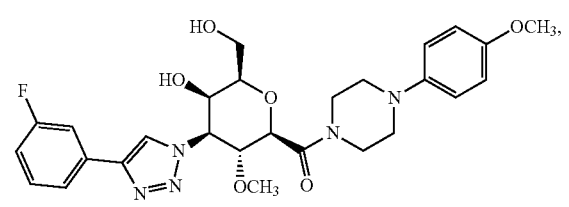
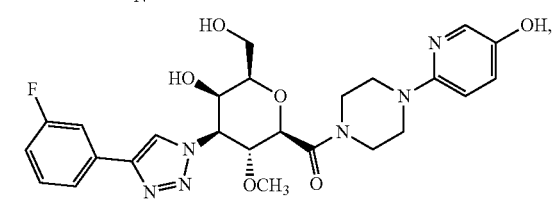
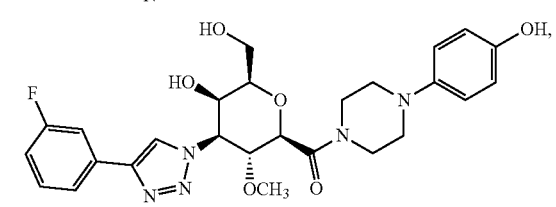
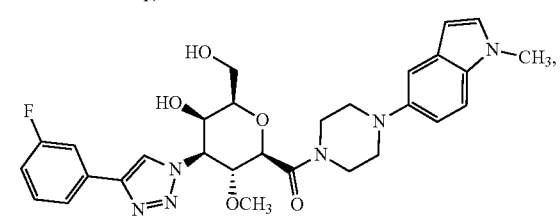
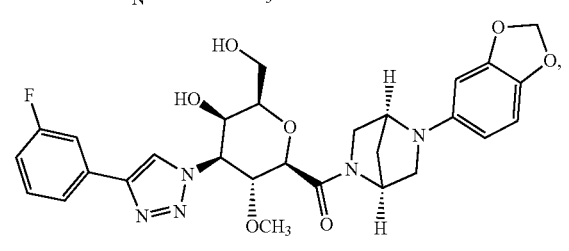
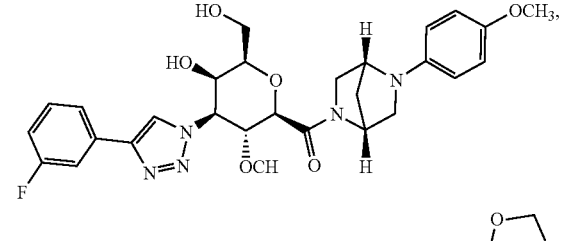
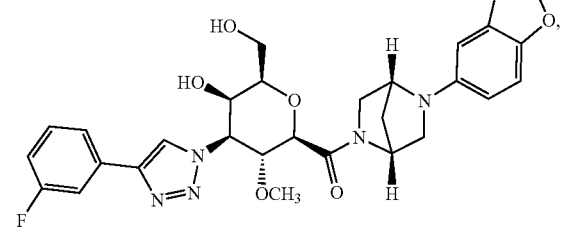
88
-continued
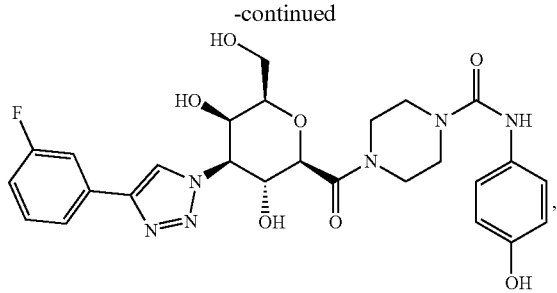
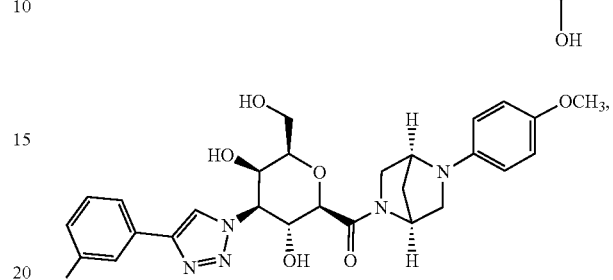
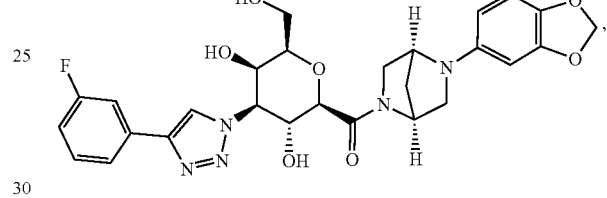
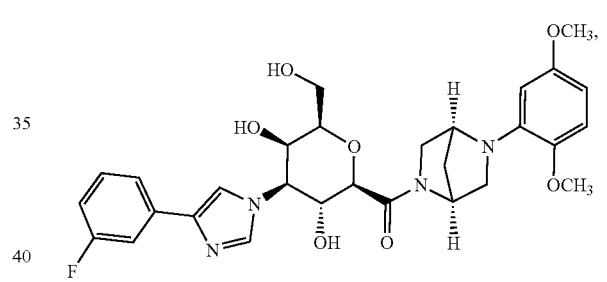
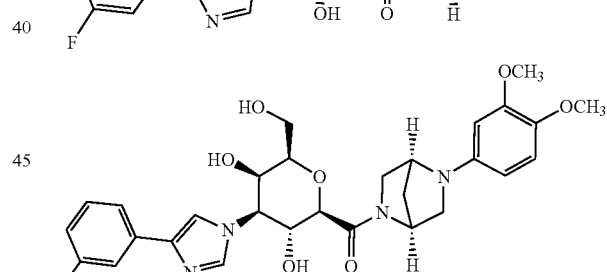
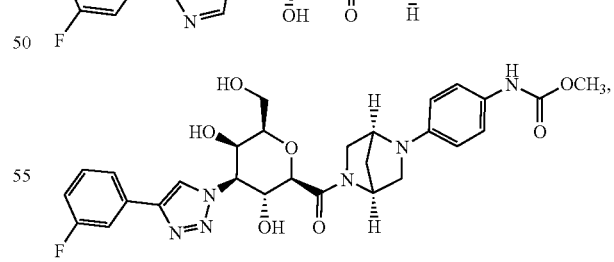
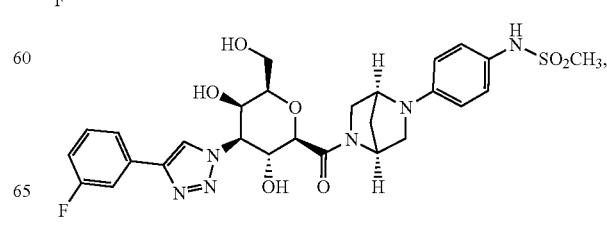

-continued
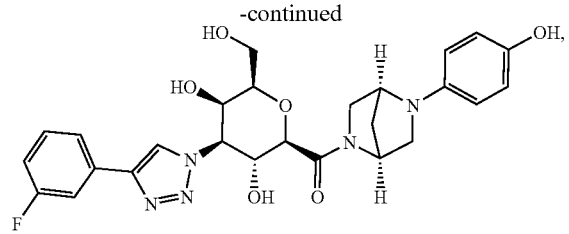
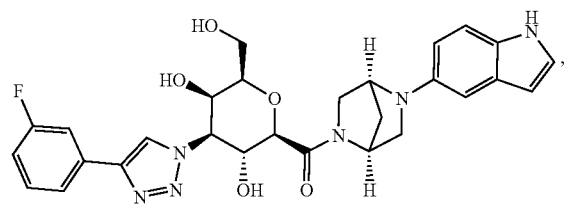
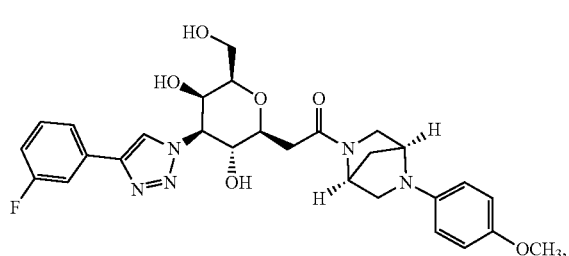
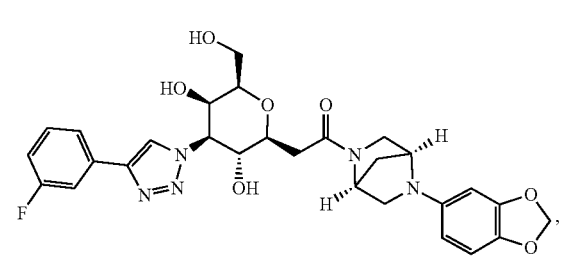
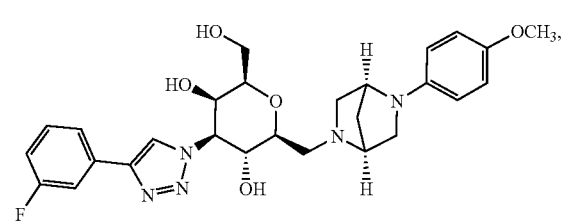
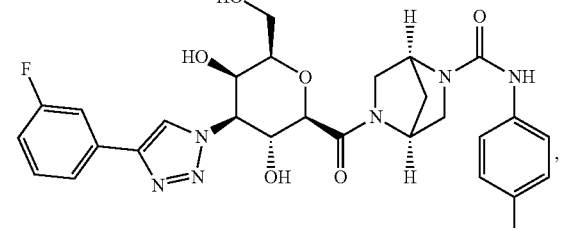
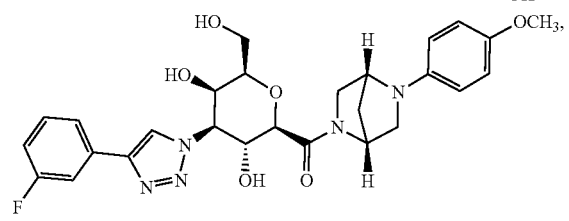
-continued
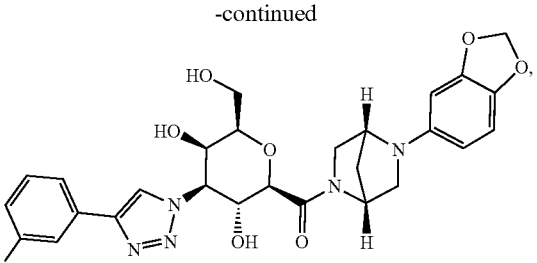
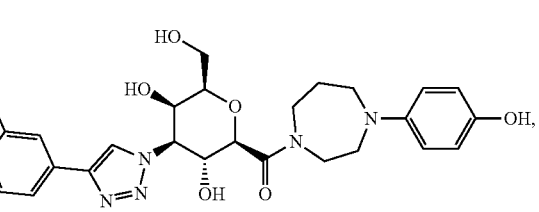
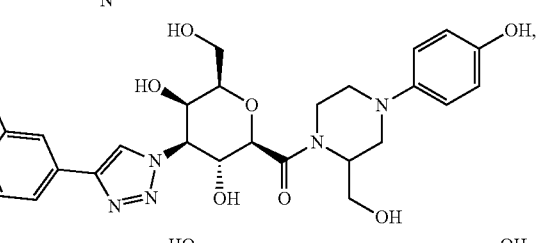
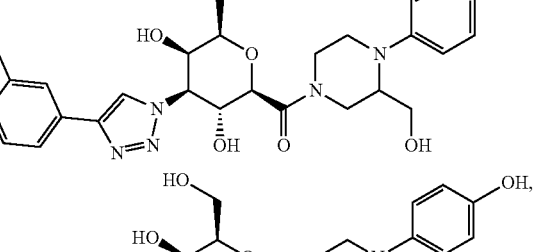
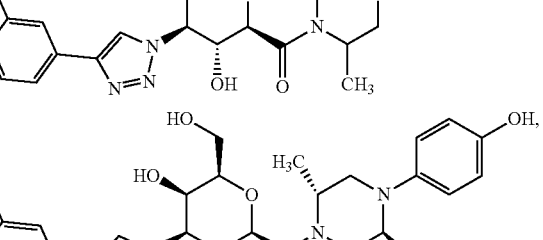
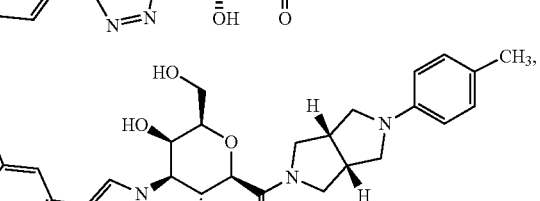
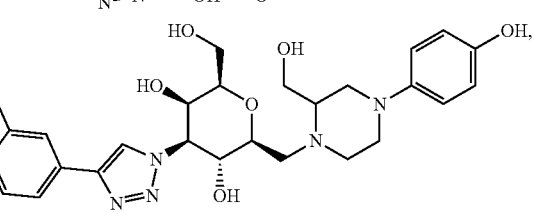

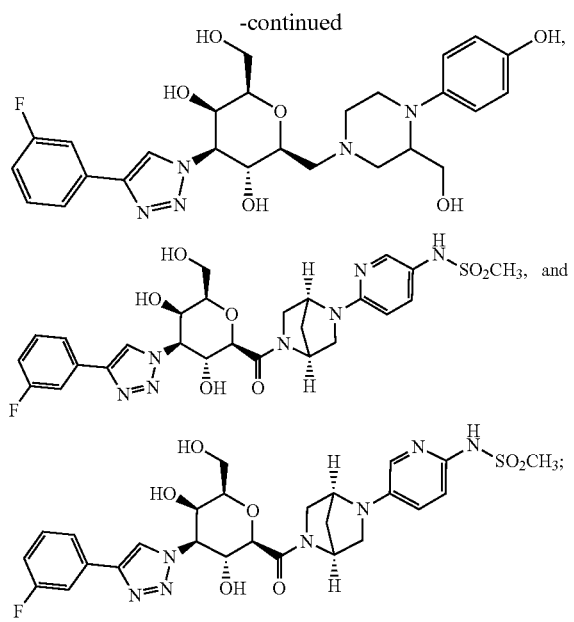

or a pharmaceutically acceptable salt thereof.

8. A composition comprising a therapeutically effective amount of a compound of claim 1, or a pharmaceutically acceptable salt thereof, and a pharmaceutically acceptable carrier.

9. A method for treating fibrosis of organs selected from liver, kidney, lung, heart and skin, liver diseases and conditions selected from acute hepatitis, chronic hepatitis, liver fibrosis, liver cirrhosis, portal hypertension, regenerative failure, non-alcoholic steatohepatitis, liver hypofunction, and hepatic blood flow disorder, cell proliferative diseases, cancers, and conditions selected from solid tumor, solid tumor metastasis, vascular fibroma, myeloma, multiple myeloma, Kaposi's sarcoma, leukemia, chronic lymphocytic leukemia and invasive metastasis of cancer cell, inflammatory diseases and conditions selected from psoriasis, nephropathy, and pneumonia, gastrointestinal tract diseases and conditions selected from irritable bowel syndrome, inflammatory bowel disease, and abnormal pancreatic secretion), renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes, lower urinary tract diseases and conditions selected from obstruction of lower urinary tract, inflammatory diseases and conditions of lower urinary tract selected from dysuria and frequent urination, pancreatic diseases and conditions, abnormal angiogenesis-associated diseases and conditions of arterial obstruction, scleroderma, brain-associated diseases and conditions selected from cerebral infarction and cerebral hemorrhage, neuropathic pain and peripheral neuropathy, ocular diseases and conditions selected from age-related macular degeneration, diabetic retinopathy, proliferative vitreoretinopathy, cicatricial pemphigoid, and glaucoma filtration surgery scarring, comprising administering a therapeutically effective amount of a compound or a pharmaceutically acceptable salt thereof of claim 1, to a patient.

10. A method for treating renal fibrosis, pulmonary fibrosis, hepatic fibrosis, arterial fibrosis, or systemic sclerosis, comprising administering a therapeutically effective amount of a compound or a pharmaceutically acceptable salt thereof of claim 1, to a patient.

11. A composition comprising a therapeutically effective amount of a compound of claim 2, or a pharmaceutically acceptable salt thereof, and a pharmaceutically acceptable carrier.

12. A method for treating fibrosis of organs selected from liver, kidney, lung, heart and skin), liver diseases and conditions selected from acute hepatitis, chronic hepatitis, liver fibrosis, liver cirrhosis, portal hypertension, regenerative failure, non-alcoholic steatohepatitis, liver hypofunction, and hepatic blood flow disorder, cell proliferative diseases, cancers, and conditions selected from solid tumor, solid tumor metastasis, vascular fibroma, myeloma, multiple myeloma, Kaposi's sarcoma, leukemia, chronic lymphocytic leukemia and invasive metastasis of cancer cell, inflammatory diseases and conditions selected from psoriasis, nephropathy, and pneumonia, gastrointestinal tract diseases and conditions selected from irritable bowel syndrome, inflammatory bowel disease, and abnormal pancreatic secretion, renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes, lower urinary tract diseases and conditions selected from obstruction of lower urinary tract, inflammatory diseases and conditions of lower urinary tract selected from dysuria and frequent urination, pancreatic diseases and conditions, abnormal angiogenesis-associated diseases and conditions of arterial obstruction, scleroderma, brain-associated diseases and conditions selected from cerebral infarction and cerebral hemorrhage, neuropathic pain and peripheral neuropathy, ocular diseases and conditions selected from age-related macular degeneration, diabetic retinopathy, proliferative vitreoretinopathy, cicatricial pemphigoid, and glaucoma filtration surgery scarring, comprising administering a therapeutically effective amount of a compound or a pharmaceutically acceptable salt thereof of claim 2, to a patient.

13. A method for treating renal fibrosis, pulmonary fibrosis, hepatic fibrosis, arterial fibrosis, or systemic sclerosis, comprising administering a therapeutically effective amount of a compound or a pharmaceutically acceptable salt thereof of claim 2, to a patient.

14. A composition comprising a therapeutically effective amount of a compound of claim 5, or a pharmaceutically acceptable salt thereof, and a pharmaceutically acceptable carrier.

15. A method for treating fibrosis of organs selected from liver, kidney, lung, heart and skin), liver diseases and conditions selected from acute hepatitis, chronic hepatitis, liver fibrosis, liver cirrhosis, portal hypertension, regenerative failure, non-alcoholic steatohepatitis, liver hypofunction, and hepatic blood flow disorder, cell proliferative diseases, cancers, and conditions selected from solid tumor, solid tumor metastasis, vascular fibroma, myeloma, multiple myeloma, Kaposi's sarcoma, leukemia, chronic lymphocytic leukemia and invasive metastasis of cancer cell, inflammatory diseases and conditions selected from psoriasis, nephropathy, and pneumonia, gastrointestinal tract diseases and conditions selected from irritable bowel syndrome, inflammatory bowel disease, and abnormal pancreatic secretion, renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes, lower urinary tract diseases and conditions selected from obstruction of lower urinary tract, inflammatory diseases and conditions of lower urinary tract selected from dysuria and frequent urination, pancreatic diseases and conditions, abnormal angiogenesis-associated diseases and conditions of arterial obstruction, scleroderma, brain-associated diseases and conditions selected from cerebral infarction and cerebral hemorrhage, neuropathic pain and peripheral neuropathy, ocular diseases and conditions selected from age-related macular degeneration, diabetic retinopathy, proliferative vitreoretinopathy, cicatricial pemphigoid, and glaucoma filtration surgery scarring, comprising administering a therapeutically effective amount of a compound or a pharmaceutically acceptable salt thereof of claim 5, to a patient.

16. A method for treating renal fibrosis, pulmonary fibrosis, hepatic fibrosis, arterial fibrosis, or systemic sclerosis, comprising administering a therapeutically effective amount of a compound or a pharmaceutically acceptable salt thereof of claim 5, to a patient.

17. A composition comprising a therapeutically effective amount of a compound of claim 7, or a pharmaceutically acceptable salt thereof, and a pharmaceutically acceptable carrier.

18. A method for treating fibrosis of organs selected from liver, kidney, lung, heart and skin), liver diseases and conditions selected from acute hepatitis, chronic hepatitis, liver fibrosis, liver cirrhosis, portal hypertension, regenerative failure, non-alcoholic steatohepatitis, liver hypofunction, and hepatic blood flow disorder, cell proliferative diseases, cancers, and conditions selected from solid tumor, solid tumor metastasis, vascular fibroma, myeloma, multiple myeloma, Kaposi's sarcoma, leukemia, chronic lymphocytic leukemia and invasive metastasis of cancer cell, inflammatory diseases and conditions selected from psoriasis, nephropathy, and pneumonia, gastrointestinal tract diseases and conditions selected from irritable bowel syndrome, inflammatory bowel disease, and abnormal pancreatic secretion, renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes, lower urinary tract diseases and conditions selected from obstruction of lower urinary tract, inflammatory diseases and conditions of lower urinary tract selected from dysuria and frequent urination, pancreatic diseases and conditions, abnormal angiogenesis-associated diseases and conditions of arterial obstruction, scleroderma, brain-associated diseases and conditions selected from cerebral infarction and cerebral hemorrhage, neuropathic pain and peripheral neuropathy, ocular diseases and conditions selected from age-related macular degeneration, diabetic retinopathy, proliferative vitreoretinopathy, cicatricial pemphigoid, and glaucoma filtration surgery scarring, comprising administering a therapeutically effective amount of a compound or a pharmaceutically acceptable salt thereof of claim 7, to a patient.

19. A method for treating renal fibrosis, pulmonary fibrosis, hepatic fibrosis, arterial fibrosis, or systemic sclerosis, comprising administering a therapeutically effective amount of a compound or a pharmaceutically acceptable salt thereof of claim 7, to a patient.

\* \* \* \* \*

UNITED STATES PATENT AND TRADEMARK OFFICE
CERTIFICATE OF CORRECTION

PATENT NO. : 12,286,424 B2
APPLICATION NO. : 17/998261
DATED : April 29, 2025
INVENTOR(S) : Prasada Jalagam et al.

Page 1 of 1

It is certified that error appears in the above-identified patent and that said Letters Patent is hereby corrected as shown below:

In the Claims

Column 86

Claim 7, Line 37-43, delete " 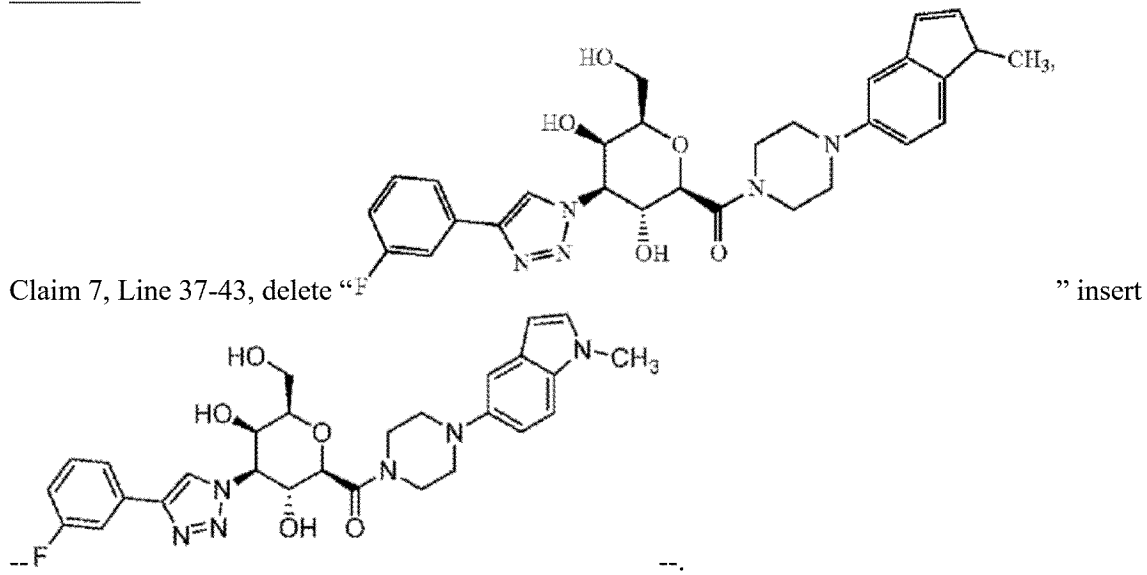 " insert -- 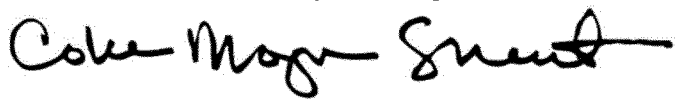 --.

Signed and Sealed this
Nineteenth Day of August, 2025

Coke Morgan Stewart
*Acting Director of the United States Patent and Trademark Office*